(12) United States Patent
van Walsem et al.

(10) Patent No.: US 8,304,209 B2
(45) Date of Patent: Nov. 6, 2012

(54) SOLAR BIOFACTORY, PHOTOBIOREACTORS, PASSIVE THERMAL REGULATION SYSTEMS AND METHODS FOR PRODUCING PRODUCTS

(75) Inventors: Johan van Walsem, Acton, MA (US); Frederick Morgan, Canton, MA (US); Stuart A. Jacobson, Lexington, MA (US); Rainer Ponzel, Charlestown, MA (US); James R. McIntire, Castro Valley, CA (US); Scott A. Michonski, Cambridge, MA (US); Andrew Posner, Cambridge, MA (US)

(73) Assignee: Joule Unlimited Technologies, Inc., Bedford, MA (US)

( * ) Notice: Subject to any disclaimer, the term of this patent is extended or adjusted under 35 U.S.C. 154(b) by 0 days.

(21) Appl. No.: 13/061,116

(22) PCT Filed: Dec. 11, 2009

(86) PCT No.: PCT/US2009/006516
§ 371 (c)(1),
(2), (4) Date: Feb. 25, 2011

(87) PCT Pub. No.: WO2010/068288
PCT Pub. Date: Jun. 17, 2010

(65) Prior Publication Data
US 2011/0151507 A1    Jun. 23, 2011

Related U.S. Application Data

(60) Provisional application No. 61/201,548, filed on Dec. 11, 2008, provisional application No. 61/216,949, filed on May 21, 2009.

(51) Int. Cl.
*C12P 1/00* (2006.01)
(52) U.S. Cl. ...................................... 435/41; 435/292.1
(58) Field of Classification Search .................. None
See application file for complete search history.

(56) References Cited

U.S. PATENT DOCUMENTS

| | | |
|---|---|---|
| 4,198,953 A | 4/1980 | Power |
| 4,868,123 A | 9/1989 | Berson et al. |
| 4,952,511 A | 8/1990 | Radmer |
| 4,970,166 A | 11/1990 | Mori |
| 5,104,803 A | 4/1992 | Delente |
| 5,151,347 A | 9/1992 | Delente et al. |
| 5,162,051 A | 11/1992 | Hoeksema |
| 5,614,378 A | 3/1997 | Yang et al. |
| 5,846,816 A | 12/1998 | Forth |
| 5,958,761 A | 9/1999 | Yogev et al. |
| 5,981,271 A | 11/1999 | Doucha et al. |
| 6,083,740 A | 7/2000 | Kodo et al. |
| 6,174,720 B1 | 1/2001 | Oxley et al. |
| 6,492,149 B1 | 12/2002 | Muller-Feuga |
| 6,492,799 B1 | 12/2002 | Rajala et al. |
| 6,509,188 B1 | 1/2003 | Trösch et al. |
| 6,602,703 B2 | 8/2003 | Dutil |
| 6,603,069 B1 | 8/2003 | Muhs et al. |
| 6,699,696 B2 | 3/2004 | Woods et al. |
| 7,374,928 B2 | 5/2008 | Trösch |
| 7,682,821 B2 * | 3/2010 | Woods et al. ............... 435/292.1 |
| 2004/0048364 A1 | 3/2004 | Trosch |
| 2005/0239182 A1 | 10/2005 | Berzin |
| 2005/0260553 A1 * | 11/2005 | Berzin ............................. 435/3 |
| 2006/0033222 A1 | 2/2006 | Godfrey et al. |
| 2007/0048848 A1 | 3/2007 | Sears |
| 2007/0048859 A1 | 3/2007 | Sears |
| 2007/0289206 A1 | 12/2007 | Kertz |
| 2008/0018964 A1 | 1/2008 | Li et al. |
| 2008/0086939 A1 | 4/2008 | Dunlop et al. |
| 2008/0153080 A1 | 6/2008 | Woods et al. |
| 2008/0160591 A1 | 7/2008 | Willson et al. |
| 2008/0160593 A1 | 7/2008 | Oyler |
| 2008/0178739 A1 | 7/2008 | Lewnard et al. |
| 2008/0219010 A1 | 9/2008 | Oyama |
| 2008/0220515 A1 | 9/2008 | McCall |
| 2008/0274494 A1 | 11/2008 | Kertz |
| 2008/0286851 A1 | 11/2008 | Whitton |
| 2008/0293132 A1 | 11/2008 | Goldman et al. |
| 2009/0081743 A1 | 3/2009 | Hazelbeck et al. |
| 2009/0113790 A1 | 5/2009 | Erd |
| 2009/0203067 A1 * | 8/2009 | Eckerle et al. .................. 435/41 |
| 2010/0028976 A1 | 2/2010 | Hu et al. |

FOREIGN PATENT DOCUMENTS

| | | |
|---|---|---|
| EP | 0 786 825 A1 | 7/1997 |
| EP | 1 995 304 A1 | 11/2008 |
| GB | 2 182 076 A | 5/1987 |
| JP | 10 304872 A | 11/2008 |
| KR | 2001 079 126 A | 8/2001 |
| KR | 2002 079 126 A | 10/2002 |
| WO | WO 91/08314 A1 | 6/1991 |

(Continued)

OTHER PUBLICATIONS

Sierra et al., Chemical Engineering Journal, 2008, Vo. 138, p. 136-147.*
Castenholz, R.W., Bacteriological Reviews, 1969, p. 476-504.*
International Preliminary Report on Patentability and Written Opinion, PCT/US2009/006516, mailing date Jun. 23, 2011.
Patent Cooperation Treaty, International Search Report and Written Opinion dated Aug. 9, 2010, PCT/US2009/006516.
Pulz, O., "Photobioreactors: production systems for phototrophic microorganisms," *Appl. Microbial. Biotechnol.*, 57: 287-293 (Jan. 2001).

(Continued)

*Primary Examiner* — Kade Ariani
(74) *Attorney, Agent, or Firm* — Chang B. Hong, Esq.

(57) ABSTRACT

The invention described herein relates to photobioreactors, methods, assembly and use of such apparatus for culturing light-capturing organisms in a cost-effective manner. Various embodiments provide for a passive thermal regulation system employing selected microorganisms in a photobioreactor apparatus and methods for biological production of various fuel and chemical products from these organisms. Additional embodiments provide a solar biofactory system capable of culturing light capturing organisms to an areal productivity of 3.3 g/m2/hr. Further embodiments are directed to a photobioreactor capable of culturing light capturing organisms to an $OD_{730}$ of about 14 g/L DCW. Such embodiments incorporate passive thermal regulation and systems.

10 Claims, 23 Drawing Sheets

FOREIGN PATENT DOCUMENTS

| WO | WO 96/21723 A1 | 7/1996 |
|---|---|---|
| WO | WO 99/15620 A1 | 4/1999 |
| WO | WO 01/92579 | 12/2001 |
| WO | WO 03/094598 A1 | 11/2003 |
| WO | WO 2005/006838 A2 | 1/2005 |
| WO | WO 2005/101525 A2 | 10/2005 |
| WO | WO 2005/104819 A1 | 11/2005 |
| WO | WO 2006/020802 A2 | 2/2006 |
| WO | WO 2007/011343 | 1/2007 |
| WO | WO 2007/025145 A2 | 3/2007 |
| WO | WO 2007/070452 A1 | 6/2007 |
| WO | WO 2007/098150 A2 | 8/2007 |
| WO | WO 2007/147028 A2 | 12/2007 |
| WO | WO 2008/008262 A2 | 1/2008 |
| WO | WO 2008/010737 A1 | 1/2008 |
| WO | WO 2008/055190 A2 | 5/2008 |
| WO | WO 2008/076998 A1 | 6/2008 |
| WO | WO 2008/083352 A1 | 7/2008 |
| WO | WO 2008/143775 A2 | 11/2008 |
| WO | WO 2008/151376 A1 | 12/2008 |
| WO | WO 2009/002772 A2 | 12/2008 |
| WO | WO 2010/012028 A1 | 2/2010 |

OTHER PUBLICATIONS

Hu, Quiang, et al., "Optimal Tilt Angles of Enclosed Reactors for Growing Photoautotrophic Microorganisms Outdoors" *Journal of Fermentation and Bioengineering*, vol. 85, No. 2, 230-236, 1998.

Chisti, Yusuf, "Pneumatically agitated bioreactors in industrial and environmental bioprocessing: Hydrodynamics, hydraulics, and transport phenomena", ASME Reprint No. AMR 233, *Appl. Mech. Rev.*, vol. 51, No. 1, pp. 33-112, Jan. 1998.

Hu, Quiang, et al., "A Flat Inclined Modular Photobioreactor for Outdoor Mass Cultivation of Photoautotrophs", *Biotechnology and Bioengineering*, vol. 51, pp. 51-60, 1996.

Janssen, Marcel, et al., "Enclosed Outdoor Photobioreactors: Light Regime, Photosynthetic Efficiency, Scale-Up, and Future Prospects", *Biotechnology and Bioengineering*, vol. 81, No. 2, pp. 193-210, Jan. 20, 2003.

Sheehan, John, et al., "A Look Back at the U.S. Department of Energy's Aquatic Species Program: Biodiesel from Algae," NERL/TP-580-24190, (1998).

Reed, T. B. and Gaur, S., *A Survey of Biomass Gasification*, NREL, Table of Contents, (2001).

Samson, R. & Leduy, A., "Multistage continuous cultivation of bluegreen alga *Spirulina maxima* in the flat tank photobioreactors with recycle." *Can. J. Chem. Eng.* 63: 105-112, (1985).

Ramos de Ortega, A. and Roux, J. C., "Production of *Chlorella* biomass in different types of flat bioreactors in temperate zones", *Biomass* 10: 141-156; (1986).

Tredici, M. R. And Materassi, R., "From open ponds to vertical alveolar panels: the Italian experience in the development of reactors for the mass cultivation of photoautotrophic microorganisms", *J. Appl. Phycol.* 4: 221-31, (1992).

Tredici, M. R., et al., "A vertical alveolar panel (VAP) for outdoor mass cultivation of microalgae and Cyanobacteria", *Bioresource Technol.* 38: 153-159, (1991).

Qiang, H. and Richmond, A., "Productivity and photosynthetic efficiency of *Spirulina platensis* as affected by light intensity, algal density and rate of mixing in a flat plate photobioreactor," *J. Appl. Phycol.* 8: 139-145, (1996).

Qiang, H., et al., "Combined effects of light intensity, light-path and culture density on output rate of *Spirulina platensis* (Cyanobacteria)," *European Journal of Phycology* 33: 165-171, (1998).

Molina, Grima E., et al., "Photobioreactors: light regime, mass transfer, and scale-up", *J. of Biotechnology*, 70:231-247, (1999).

Rogers, L. J. and Gallon, J. R., *Biochemistry of the Algae and Cyanobacteria*, Clarendon Press Oxford, Table of Contents, (1988).

Burlew, John S., *Algal Culture: From Laboratory to Pilot Plant*, Carnegie Institution of Washington, Publication 600. Washington, D.C., Table of Contents, (1961).

Round, F. E., *The Biology of the Algae*, St Martin's Press, New York, Table of Contents, (1965).

McDonald, S.A., et al., "Solution-processed PbS quantum dot infrared photodetectors and photovoltaics", Nat Mater, 4(2): 138-42, (2005).

Liu, M.O., "Thermal and fluorescent properties of optical brighteners and their whitening effect for pelletizxation of cycloolefi copolymers," Mat Letters, 60(17-18) 2132-213. (2006).

Walach, Marek R., "The growth and adhesion to glass of algal (*Chlorella*) cells: the effects of iron and other mineral nutrients," *Appl Microbiol Biotechnol.* (Nov. 24, 2004).

Pirt, J., "The thermodynamic efficiency (quantum demand) and dynamics of photosynthetic growth", New Phytol., 102:3-37, (1986).

Gitelson, A., et al., "Photic volume in photobioreactors supporting ultrahigh population densities of the photoautotroph Spirulina platensis," *Applied and Environmental Microbiology* 62:1570-1573, (1996).

Golden, S.S., et al., "Genetic engineering of the Cyanobacteria chromosome," *Methods Enzymol*, 153:215-231, (1987).

Golden, S. S. And L. A. Sherman, "Optimal Conditions for Genetic Transformation of the Cyanobacterium *Anacystis nidulans* R2," *J. Bacteriology*, 158:36 (1984).

Brock, Thomas D., *Biotechnology: A Textbook of Industrial Microbiology*, Second Edition, Sinauer Associates, Inc., Sunderland, Mass., Table of Contents, (1989).

Deshpande, Mukund V., "Ethanol Production from Cellulose by Coupled Saccharification/Fermentation using *Saccharomyces cerevisiae* and Cellulase Complex from *Sclerotium rolfsii* UV-8 Mutane," *Appl. Biochem. Biotechnol*, 36:227, (1992).

Ausbel, et al., *Capillary Electrophoresis: Theory and Practice*, P. Grossman and J. Colburn, eds., Academic Press Table of Contents, (1992).

Ladisch, M., *Bioseparations Engineering: Principles, Practice, and Economics*, John Wiley & Sons, Table of Contents, (2001).

Liebler, *Introduction to Proteomics*, Humana Press, Table of Contents, (2002).

Knothe, G. R., et al., "Biodiesel: The use of vegetable oils and their derivatives as alternative diesel fuels," *Am. Chem. Soc. Symp. Series* 666: 172-208, (1997).

Komers, K., et al., "Determination of the neutralization number for biodiesel fuel production," *Fett/Lipid* 99(2): 52-54, 1997.

Bailer, J., and de Huebe, K., "Determination of saponifiable glycerol in bio-diesel." Fresenius *J. Anal. Chem.*, 340(3): 186, (1991).

"Passive Solar Heating and Cooling" [online] Arizona Solar Center http://www.azsolarcenter.com/technology/pas-3.html, 2012.

Frigaard, N. U., et al., "Gene inactivation in the cyanobacterium *Synechococcus* sp. PCC 7002 and the green sulfur bacterium *Chlorobium tepidum* using in vitro-made DNA constructs and natural transformation," *Methods Mol Biol* 274:325-340, (2004).

Pirt, S. J., "Biotechnology Report—Maximum Photosynthetic Efficiency: A Problem to be Resolved," *Biotechnol Bioeng*, 25: 1915-1922, 1983.

Pirt, S.J., "The maintenance of energy of bacteria in growing cutures," *Proc Roy Soc*, 163: 224-231, 1965.

\* cited by examiner

| | Net Heat Absorbed Nighttime (kJ m$^{-2}$) | Net Heat Absorbed Daytime (kJ m$^{-2}$) | Net Heat Absorbed Entire Day (kJ m$^{-2}$) | Net Heat Absorbed Entire Day (W m$^{-2}$) |
|---|---|---|---|---|
| Jun Thermophile | -7203 | +1263 | -5904 | -68 |
| Sep Thermophile | -9834 | +229 | -9605 | -111 |
| Dec Thermophile | -22,253 | -9997 | -32,250 | -373 |
| Mar Thermophile | -16,232 | -6665 | -22,897 | -265 |
| Jun Mesophile | 587 | 13,681 | 14,269 | 165 |
| Sep Mesophile | -1261 | 12,778 | 11,517 | 133 |
| Dec Mesophile | -9304 | 2034 | -7270 | -84 |
| Mar Mesophile | -5692 | 7019 | 1327 | 15 |

FIG. 13

SOLAR BIOFACTORY, PHOTOBIOREACTORS, PASSIVE THERMAL REGULATION SYSTEMS AND METHODS FOR PRODUCING PRODUCTS

RELATED APPLICATION

This application is the U.S. National Stage of International Application No. PCT/US2009/006516, filed Dec. 11, 2009, which designates the U.S., published in English, and claims the benefit of U.S. Provisional Application No. 61/201,548, filed on Dec. 11, 2008 and U.S. Provisional Application No. 61/216,949 filed on May 21, 2009. The entire teachings of the above applications are incorporated herein by reference.

FIELD OF INVENTION

The disclosure herein generally relates to solar biofactories, photobioreactor apparatus, photobioreactors, systems and methods for culturing light capturing organisms using the same for the biological production of carbon-based products of interest.

BACKGROUND

Burning of fossil fuels is thought to have resulted in elevated atmospheric carbon dioxide ($CO_2$) concentrations. The levels of carbon dioxide are expected to double in as little as 60 years based on changes in land use and continued burning of fossil fuels. The increase in carbon dioxide concentrations as well as other greenhouse gases is thought to keep heat within the atmosphere, leading to higher global temperatures. Sequestration—the long term capture and storage of carbon dioxide—has been long thought of as a way to mitigate this problem. Given however, that light and carbon dioxide make up most of what is consumed, direct conversion of ambient carbon dioxide to valuable products, such as fuels, chemicals, drugs, and their precursors, represents an alternative and improved means to reduce the effects of carbon dioxide while maintaining the core industrial and commercial products our modern society demands.

Plants and other light capturing organisms are the main method by which carbon dioxide is removed from the atmosphere. Through photosynthesis, organisms use solar energy while capturing carbon dioxide, important metabolic precursors can be made that can be converted to biomass in amounts exceeding 90% (Sheehan John, Dunahay Terri, Benemann John R., Roessler Paul, "A Look Back at the U.S. Department of Energy's Aquatic Species Program: Biodiesel from Algae," 1998, NERL/TP-580-24190). Previous approaches have sought to increase production of algal biomass and potentially use that biomass as a fuel. (Reed T. B. and Gaur S. "A Survey of Biomass Gasification" NREL, 2001). It has been additionally demonstrated that addition of a small subset of genes can enable light capturing organisms to produce ethanol. Specifically, the expression of alcohol dehydrogenase II and pyruvate decarboxylase from *Z. mobilis* in a Cyanobacterium has been achieved resulting in low levels of ethanol production (U.S. Pat. No. 6,699,696). Nonetheless, the ability to produce algae as well as to produce products from light capturing organisms has been well below the efficiency needed to have a commercially viable and therefore meaningful impact on ambient or waste carbon dioxide (U.S. Pat. No. 6,699,696; Sheehan John, Dunahay Terri, Benemann John R., Roessler Paul, "A Look Back at the U.S. Department of Energy's Aquatic Species Program: Biodiesel from Algae," 1998, NERL/TP-580-24190)

One of the primary limitations of using algae as a method of carbon dioxide sequestration or conversion to products has been the development of efficient and cost-effective growth systems. Aquatic organisms, such as algae, oysters, and lobsters, have been primarily cultured in open systems. This approach allows for the organisms to take advantage of the semi-natural environment while keeping operational expenditures potentially lower. Open algal ponds up to 4 $km^2$ have been researched, which, while requiring low capital expenditures, ultimately have low productivity as these systems are also subject to a number of problems. Intrinsic to being an open system, the cultured organisms are exposed to a number of exogenous organisms which may be symbiotic, competitive, or pathogenic. Symbiotic organisms can change the culture organisms merely by exposing them to a different set of conditions. Opportunistic species may compete with the desired organism for space, nutrients, etc. Additionally, pathogenic invaders may feed on or kill the desired organism. In addition to these complicating factors, open systems are difficult to insulate from environmental changes including temperature, turbidity, pH, salinity, and exposure to the sun. These difficulties point to the need to develop a closed, controllable system for the growth of algae and similar organisms.

Not surprisingly, a number of closed photobioreactors have been developed. Typically, these are cylindrical or tubular (i.e., U.S. Pat. No. 5,958,761, US Patent application No. 2007/0048859). These bioreactors often require mixing devices, increasing cost, and are prone to accumulating oxygen ($O_2$), which inhibits algal growth.

As discussed in WO 2007/011343, many conventional photobioreactors comprise cylindrical algal photobioreactors that can be categorized as either "bubble columns" or "air lift reactors." Vertical photobioreactors, which operate as "bubble columns" are large diameter columns with algal suspensions wherein gas is bubbled in from the bottom. Using bubbling as a means of mixing in large-diameter columns is thought to be inefficient, providing for lower net productivity as certain elements of the culture remain photo-poor and as large bubbles of gas do not deliver necessary precursors. An alternative vertical reactor is the air-lift bioreactor, where two concentric tubular containers are used with air bubbled in the bottom of the inner tube, which is opaque. The pressure causes upward flow in the inner tube and downward in the outer portion, which is of translucent make. These reactors have better mass transfer coefficients and algal productivity than other reactors, though controlling the flow remains a difficulty. Efficient mixing and gas distribution are key issues in developing closed bioreactors and to date, such efficient bioreactors do not exist.

Tubular bioreactors, when oriented horizontally, typically require additional energy to provide mixing (e.g., pumps), thus adding significant capital and operational expense. In this orientation, the $O_2$ produced by photosynthesis can readily become trapped in the system, thus causing a significant reduction in algal proliferation. Other known photobioreactors are oriented vertically and agitated pneumatically. Many such photobioreactors operate as "bubble columns."

All closed bioreactors also require light, either from the sun or artificially derived (U.S. Pat. No. 6,083,740). Solar penetration is typically enabled through translucent tubing, which, with thinner diameter, enables more thorough saturation of the algae. Some known photobioreactor designs rely on artificial lighting, e.g. fluorescent lamps, (such as described by Kodo et al. in U.S. Pat. No. 6,083,740), and can otherwise be provided by any light source existing today.

Photobioreactors that do not utilize solar energy but instead rely solely on artificial light sources can require enormous energy input, increasing cost, and rendering these systems, as stand-alone approaches, impractical. Using natural solar light requires a low cost means to allow for proper penetration of the culture while maintaining the culture at a temperature that is appropriate.

In addition, because of geometric design constraints, during large-scale, outdoor algal production, both types of cylindrical photobioreactors can suffer from low productivity, due to factors related to light reflection and auto-shading effects (in which one column is shading the other). Shading issues make for inefficiencies on vertical bioreactor design, leading to low land use.

Several flat-plate photobioreactor designs have been disclosed for culturing microalgae: Samson R & Leduy A (1985) Multistage continuous cultivation of blue-green alga *Spirulina maxima* in the flat tank photobioreactors with recycle. *Can. J. Chem. Eng.* 63: 105-112; Ramos de Ortega and Roux J. C. (1986) Production of *Chlorella* biomass in different types of flat bioreactors in temperate zones. *Biomass* 10: 141-156; Tredici M. R. and Materassi R. (1992) From open ponds to vertical alveolar panels: the Italian experience in the development of reactors for the mass cultivation of photoautotrophic microorganisms. *J. Appl. Phycol.* 4: 221-31. Tredici M. R., Carlozzi P., Zittelli G. C. and Materassi R. (1991) A vertical alveolar panel (VAP) for outdoor mass cultivation of microalgae and Cyanobacteria. *Bioresource Technol.* 38: 153-159; Hu Q. and Richmond A. (1996) Productivity and photosynthetic efficiency of *Spirulina platensis* as affected by light intensity, algal density and rate of mixing in a flat plate photobioreactor. *J. Appl. Phycol.* 8: 139-145; Hu Q, Yair Z. and Richmond A. (1998) Combined effects of light intensity, light-path and culture density on output rate of *Spirulina platensis* (Cyanobacteria). European Journal of Phycology 33: 165-171; Hu et al. WO 2007/098150, however, to date, no design or system has been successfully scaled up for efficient growth of organisms in commercial scale.

Many different photobioreactor configurations have been described in the literature including flat panels, bubble columns, tubular reactors and a variety of annular designs aimed at improving the surface area to volume ratio to maximize conversion of sunlight and $CO_2$ to biomass or other products such as algal oil. These reactors have distinct advantages compared to open raceway with respect to controlling temperature, pH, nutrient and limiting contamination (see Pulz, O. "Photobioreactors: Production systems for phototrophic microorganisms", Appl. Microbiol. Biotechnol (2001) 57:287-293). Key limitations to their adoption have been the cost vs. benefit as it relates to the product being produced. Whereas valuable products such as carotenoids have been produced in photobioreactors the production of biomass for fuels could not be economically justified to date.

The art as it relates to enclosed photobioreactors achieve temperature control in a variety of ways including external and internal heat exchangers, spraying of cooling water directly on the surface, use of cooled or heater sparge gas as well as submerging the reactor directly in large pond of water that is separately temperature controlled (see Molina Grima, E. et al "Photobioreactors: light regime, mass transfer, and scale-up", J. of Biotechnology (1999) 70:231-247; Hu, Q. et al "A flat inclined photobioreactor for outdoor mass cultivation of photoautotrophs" Biotechnology and Bioengineering (1996) 51:51-60 and Hu, Q. WO 2007/098150 A2 "Photobioreactor and uses therefor"). Currently, a cost-effective thermal regulation system that can be implemented in large scale does not exist.

What is needed, therefore, is an integrated photobioreactor system that is scalable, low cost, and efficient for culturing light-capturing organisms.

SUMMARY

In various embodiments, a solar biofactory is described which can comprise photobioreactors that enable sufficient productivity for organisms growing within to have commercial viability. Disclosed are apparatuses, method of using the apparatuses, methods for growing light capturing organisms with the apparatuses and systems for growing light capturing organisms using light, water and carbon dioxide. Such photobioreactor apparatus, systems and methods are optimized for light capture while remaining low in cost, scalable, and achieve efficient growth of organisms. The methods also provide for employing and operating a solar biofactory, light capturing organisms suitable for culturing in a photobioreactor apparatus and methods for culturing the organisms. In various embodiments, such organisms grown in the photobioreactor apparatus of the solar biofactory are used in the production of biomass and chemical intermediates as well as biologically produced end products such as fuels, chemicals and pharmaceutical agents.

Furthermore, the photobioreactor can be adapted to maximize production of various desired end products in a defined area while minimizing land use. Accordingly, in additional embodiments, the invention provides a photobioreactor capable of culturing light capturing organism to an areal productivity of at least about 3.3 g/m$^2$/hr. In further embodiments, the invention provides a photobioreactor capable of producing 0.45 g/m$^2$/hr of EtOH or various other fuels and chemicals. In more preferred embodiments, the invention provides a photobioreactor capable of producing various fuels and chemicals at a desired areal productivity that minimizes land use and maximizes product output for commercial scale, e.g., 20 g/m$^2$/day or 1-1.5 g/m$^2$/hr.

To address the need for thermal regulation, what is provided are systems, methods and photobioreactor, photobioreactor assemblies and apparatus designed to passively regulate heat accumulation and dissipation in an economical and efficient manner. In various aspects, provided herein is a photobioreactor comprising: a reactor, wherein at least part of a surface of the reactor is at least translucent; and a passive thermal regulation system adapted to comprise a means to at least reduce requirements of at least one of cooling, heating or a combination thereof for the photobioreactor. In various embodiments, the passive thermal regulation system regulates the temperature of the photobioreactor between about 52 to about 65° C. (preferably between 56 and 60° C.) for a thermophile and about 37° C. for a mesophile.

Additional embodiments provide passive thermal regulation systems that manage incident solar radiation. In certain aspects, the photobioreactor comprises a surface coating means. In part, the surface coating reflects heat. The photobioreactor further comprises a ground surface coating or means to create diffuse reflection of light. The coating or means selectively traps IR as heat.

Still other embodiments include a rotatable mechanism to allow heat preservation or minimize heat loss.

Alternative embodiments equip the photobioreactor with a real time adaptive control system to adjust the inclination of a photobioreactor assembly.

In another embodiment, the photobioreactor is designed such that heat accumulation is minimized over time. Light not used to drive biological processes will contribute to heating the photobioreactor as can various inputs. The photobioreactor is designed through one or more systems including blocking infrared light, enablement of evaporative cooling, control of recycle rate, and the use of heat exchanges, to mitigate accumulation of heat over time.

In other embodiments is provided a photobioreactor assembly comprising: a reactor structure; a greenhouse structure configured to provide a greenhouse environment for the reactor structure, the reactor structure and the greenhouse structure spaced relative to each other to provide temperature control of the photobioreactor.

During the production cycle, the photobioreactor further comprises at least one microorganism selected from a thermophile, a mesophile or a combination thereof. Optimized conditions can be maintained to produce various products of interest during the various times of the year. Depending on geographical location, a thermophile can be employed in warmer temperatures (e.g., the summer). Similarly, a mesophile can be employed in cooler climates (e.g., the winter). Alternatively, thermophiles can be used in the winter while the mesophiles can be used in the summer though not optimal. The photobioreactor can provide optimal conditions for the microorganisms to produce products such as fuels and chemicals. The photobioreactor regulates temperature to optimize productivity. The photobioreactor is capable of separating products continuously. The photobioreactor is also capable of producing robust productivity and yield of product. Various aspects of the photobioreactor allow for at least reduced biomass concentration by direct production of fuels and chemicals from light capturing organisms. Preferably, separation of biomass from products of interest is obviated.

In certain aspects, the invention also provides a method for producing fuels or chemicals comprising:
(a) employing a photobioreactor wherein at least part of a surface of the photobioreactor is at least translucent; and a passive thermal regulation system adapted to comprise a means to reduce requirements of at least one of cooling, heating or a combination thereof for the photobioreactor;
(b) introducing into the photobioreactor at least one organism selected from a mesophile, a thermophile or a combination thereof;
(c) culturing the organism in the photobioreactor whereby the organisms utilize light and $CO_2$ to produce the fuels or chemicals; and
(d) removing the fuels or chemicals from the photobioreactor.

The method further includes employing an assembly comprising a real time adaptive control system to optimize productivity, and preferably, maintain optimum productivity.

Also provided is a method to produce carbon-based products of interest comprising:
(a) culturing light-harvesting organism in media comprising increased N, P and/or Fe concentration;
(b) mixing and circulating the cultured media in a photobioreactor comprising at least one panel having multiple channels wherein the organism is cultured;
whereby the organism is cultured to a density of 6-10 g/L DCW to produce the products.

Disclosed herein are various organisms, e.g., engineered organisms, phototrophs, autotrophs, heterotrophs and hyper-light capturing organisms that can be employed in the photobioreactor. In various embodiments, organisms are adapted to photosynthesize in the liquid medium under conditions suitable for producing products of interest, e.g., biomass and chemical intermediates as well as biologically produced end products such as fuels, chemicals and pharmaceutical agents.

BRIEF DESCRIPTION OF THE FIGURES

FIG. 13 is a table of heat load on a photobioreactor using fixed temperature mesophile or thermophile (net positive indicates external cooling and net negative indicates external heating).

ABBREVIATIONS AND TERMS

Figure 1:
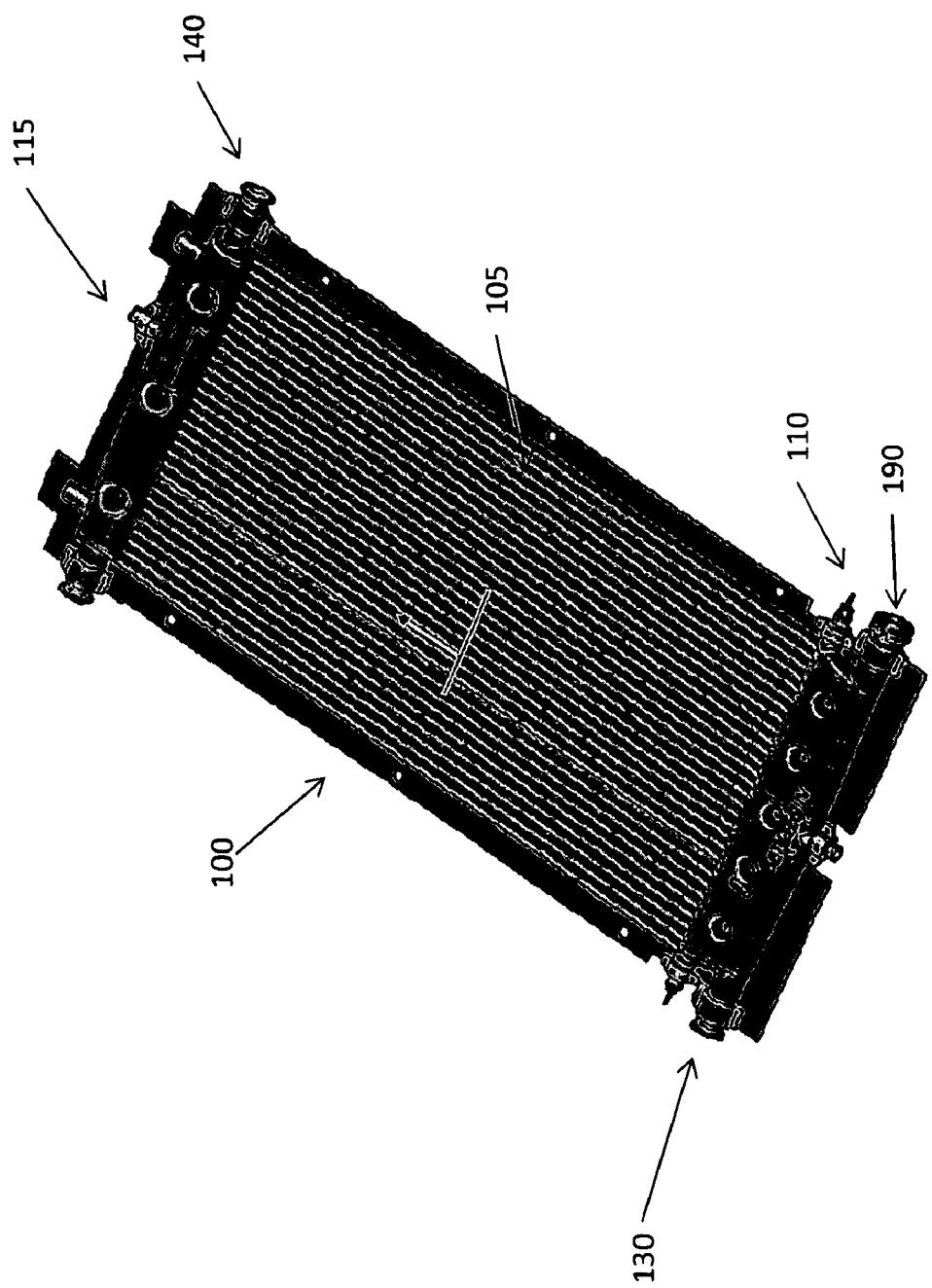
FIG. 1 depicts a thermoformed photobioreactor in a flat-panel design.

The following explanations of terms and methods are provided to better describe the present disclosure and to guide those of ordinary skill in the art in the practice of the present disclosure. As used herein, "comprising" means "including"

and the singular forms "a" or "an" or "the" include plural references unless the context clearly dictates otherwise. For example, reference to "comprising a cell" includes one or a plurality of such cells. The term "or" refers to a single element of stated alternative elements or a combination of two or more elements, unless the context clearly indicates otherwise.

Unless explained otherwise, all technical and scientific terms used herein have the same meaning as commonly understood to one of ordinary skill in the art to which this disclosure belongs. Although methods and materials similar or equivalent to those described herein can be used in the practice or testing of the present disclosure, suitable methods and materials are described below. The materials, methods, and examples are illustrative only and not intended to be limiting. Other features of the disclosure are apparent from the following detailed description and the claims.

A "biofuel" as used herein is any fuel that derives from a biological source.

"Products", "products of interest" or "carbon-based products of interest" refer to producing biological sugars, hydrocarbon products, fuels, biofuels, solid forms of carbon, or pharmaceutical agents as a result of culturing light harvesting organisms in the presence of $CO_2$ and light under conditions sufficient to produce the carbon products. Biomass is also within the scope of the term. Products can be further collected, processed or separated. These products can be secreted. Within the scope of the term includes alcohols such as ethanol, propanol, isopropanol, butanol, fatty alcohols, fatty acid esters, ethyl esters, wax esters; hydrocarbons and alkanes such as propane, octane, diesel, Jet Propellant 8 (JP8); polymers such as terephthalate, 1,3-propanediol, 1,4-butanediol, polyols, Polyhydroxyalkanoates (PHA), poly-beta-hydroxybutyrate (PHB), acrylate, adipic acid, ε-caprolactone, isoprene, caprolactam, rubber; commodity chemicals such as lactate, docosahexaenoic acid (DHA), 3-hydroxypropionate, γ-valerolactone, lysine, serine, aspartate, aspartic acid, sorbitol, ascorbate, ascorbic acid, isopentenol, lanosterol, omega-3 DHA, lycopene, itaconate, 1,3-butadiene, ethylene, propylene, succinate, citrate, citric acid, glutamate, malate, 3-hydroxypropionic acid (HPA), lactic acid, THF, gamma butyrolactone, pyrrolidones, hydroxybutyrate, glutamic acid, levulinic acid, acrylic acid, malonic acid; specialty chemicals such as carotenoids, isoprenoids, itaconic acid; pharmaceuticals and pharmaceutical intermediates such as 7-aminodeacetoxycephalosporanic acid (7-ADCA)/cephalosporin, erythromycin, polyketides, statins, paclitaxel, docetaxel, terpenes, peptides, steroids, omega fatty acids and other such suitable products of interest. Such products are useful in the context of biofuels, industrial and specialty chemicals, as intermediates used to make additional products, such as nutritional supplements, neutraceuticals, polymers, paraffin replacements, personal care products and pharmaceuticals.

Autotroph: Autotrophs (or autotrophic organisms) are organisms that produce complex organic compounds from simple inorganic molecules and an external source of energy, such as light (photoautotroph) or chemical reactions of inorganic compounds.

Phototroph: Phototrophs (photoautotrophs) are organisms that carry out photosynthesis such as, eukaryotic plants, algae, protists and prokaryotic cyanobacteria, green-sulfur bacteria, green non-sulfur bacteria, purple sulfur bacteria, and purple non-sulfur bacteria. Phototrophs also include engineered organisms to carry out photosynthesis and hyper-light capturing organisms.

Heterotroph: Heterotrophs (or heterotrophic organisms) are organisms that, unlike autotrophs, cannot derive energy directly from light or from inorganic chemicals, and so must feed on organic carbon substrates. They obtain chemical energy by breaking down the organic molecules they consume. Heterotrophs include animals, fungi, and numerous types of bacteria.

Light capturing organism: Light capturing organisms (or light capturing organisms) are organisms that use light alone or in combination with other energy sources, to drive the activities of a cell. This includes photoautotrophs, phototrophs, heterotrophs engineered to have the ability to use light to power some or all of their activities, and engineered phototrophs/photoautotrophs.

Organism: The term is used here to encompass autotrophs, phototrophs, heterotrophs, engineered light capturing organisms and at the cellular level, e.g., unicellular and multicellular.

Hydrocarbon: generally refers to a chemical compound that consists of the elements carbon (C), optionally oxygen (O), and hydrogen (H). There are essentially three types of hydrocarbons, e.g., aromatic hydrocarbons, saturated hydrocarbons and unsaturated hydrocarbons. The term also includes fuels, biofuels, plastics, waxes, solvents and oils.

Biosynthetic pathway: Also referred to as "metabolic pathway," refers to a set of anabolic or catabolic biochemical reactions for converting (transmuting) one chemical species into another. For example, a hydrocarbon biosynthetic pathway refers to the set of biochemical reactions that convert inputs and/or metabolites to hydrocarbon product-like intermediates and then to hydrocarbons or hydrocarbon products. Anabolic pathways involve constructing a larger molecule from smaller molecules, a process requiring energy. Catabolic pathways involve breaking down of larger molecules, often releasing energy.

Cellulose: Cellulose [$(C_6H_{10}O_5)_n$] is a long-chain polymer polysaccharide carbohydrate, of beta-glucose. It forms the primary structural component of plants and is not digestible by humans. Cellulose is a common material in plant cell wall. It occurs naturally in almost pure form only in cotton fiber; in combination with lignin and any hemicellulose, it is found in all plant material.

Surfactants: Surfactants are substances capable of reducing the surface tension of a liquid in which they are dissolved. They are typically composed of a water-soluble head and a hydrocarbon chain or tail. The water soluble group is hydrophilic and can be either ionic or nonionic, and the hydrocarbon chain is hydrophobic.

Photobioreactor: A photobioreactor apparatus, bioreactor or reactor is used interchangeably to describe an apparatus, device or system that supports a biologically active environment. For instance, a bioreactor can be a vessel wherein a chemical process involving photosynthesis in organisms is carried out or biochemically active substances are derived from such organisms. Such bioreactors can support activities for either aerobic or anaerobic organisms. These bioreactors are commonly cylindrical, ranging in size from liters to cubic meters, and are often made of stainless steel. Bioreactors that are adapted to allow use of light energy in the cultivation or organisms are typically referred to as photobioreactors and commonly employ transparent materials such as glass or plastic to allow light to enter the interior of the bioreactor. On the basis of mode of operation, a bioreactor may be classified as batch, fed batch or continuous (e.g. continuous stirred-tank reactor model). An example of a bioreactor is the chemostat. Organisms growing in photobioreactors may be suspended or immobilized. Various inventive embodiments are directed to photobioreactor apparatus designs and to methods and systems utilizing photobioreactor apparatus in a solar biofactory as is described throughout. Certain photobioreactor apparatus for use herein comprise an enclosed bioreactor system, as contrasted with an open bioreactor, such as a pond or other open body of water, open tanks, open channels, etc.

Light: The term "light" generally refers to sunlight but can be solar or from artificial sources including incandescent lights, LEDs, fiber optics, metal halide, neon, halogen and fluorescent lights and solar light such as near-infrared and wavelength generally between about 400-700 nm.

PAR: The term "PAR" is short for photosynthetically active radiation and is measured in $\mu E/m^2/s$.

"Corrugated panel" "sheet", "reactor" or "chamber" refers to the physical container where the culture is produced and circulated and can be made using plastic materials such as polypropylene, polyethylene, polyacrylate and polycarbonate sheets. The sheet can be partitioned longitudinally and can form channels. The corrugation can be in various geometric configurations such as rectangular, trapezoidal, triangular, circular etc. The panel can be transparent or at least translucent.

Channel: A channel generally refers to the area between each partition of a corrugated-panel or a flat-sheet photobioreactor where organisms circulate conducting photosynthesis. While channel shape and size can vary an exemplary dimension of a channel is 10 mm×10 mm×1 m. A channel may also comprise an aperature that allow air or $CO_2$ to mix with the media.

Media: The term "liquid medium", "liquid media" or "media" generally refers to the composition used for culturing organisms contained within the photobioreactor apparatus typically comprising for example in the case of algae and/or other light capturing organisms, water or a saline solution (e.g. sea water or brackish water) and sufficient nutrients to facilitate viability and growth of such organisms. As discussed below, it is often advantageous to utilize a liquid medium comprising brackish water, sea water, or other non-potable water obtained from a locality in which the photobioreactor apparatus will be operated and from which the organism contained therein was derived or is adapted to. Media also includes a nitrogen source, which can include, but is not limited to nitrate salts, urea, ammonia and ammonium salts, uric acid, and amino acids. Particular liquid medium compositions, nutrients, etc. required or suitable for use in maintaining a growing light capturing organism culture, e.g., fermentation media, are well known in the art. Potentially, a wide variety of liquid media, any medium in which an organism, when cultured, is capable of producing can be utilized in various forms for various embodiments, as would be understood by those of ordinary skill in the art. Such a medium can also include appropriate salts, minerals, metals, and other nutrients. It should be recognized, however, that a variety of fermentation conditions are suitable and can be selected by those skilled in the art. Potentially appropriate liquid medium components and nutrients are, for example, discussed in detail in: Rogers, L J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Washington, D.C., 1961 (hereinafter "Burlew 1961"); and Round, F. E. The Biology of the Algae. St Martin's Press, New York, 1965; each incorporated herein by reference).

Sparger: A sparger or a gas sparger refers to any suitable mechanism or device that can introduce for instance a plurality of small air bubbles into a liquid or liquid medium.

"Light capturing organism" refers to all organisms, natural or engineered, capable of photosynthesis such as photoautotrophic organisms (i.e., plants, algae, and photosynthetic bacteria).

"Gas aperture" refers to the point on the where gas such as $CO_2$ and air introduced for example by sparging.

"Liquid manifold" refers to a part of the photobioreactor where liquid is either introduced ("liquid introduction manifold") or where the liquid is returned ("liquid return manifold").

"Passive" refers to temperature control achieved through the use of no amount of, or a relatively small amount of, power input using air such as ambient air. In some embodiments, power input may be used for blowing air and operating a temperature control system. In an embodiment, the power input may be obtained from a pV solar panel or other power source preferably located near the reactor.

Throughout this specification and claims, the word "comprise" or variations such as "comprises" or "comprising", will be understood to imply the inclusion of a stated integer or group of integers but not the exclusion of any other integer or group of integers.

DETAILED DESCRIPTION OF THE EMBODIMENTS

Photobioreactor Apparatus & Light Capture

In certain aspects, the invention provides an efficient, low-cost, high surface area light capturing apparatus that is scalable and easily implemented in open space such as the exemplary photobioreactor apparatus as shown in FIG. 1. Such photobioreactor apparatus is adapted to capture light through a panel 100. Since different types of light capturing organisms can require different light exposure conditions for optimal growth and proliferation, additional modifications can be made to the construction of a photobioreactor apparatus to capture light according to the various embodiments.

In certain embodiments, the photobioreactor apparatus is used with natural sunlight, however, in alternative embodiments, an artificial light source providing light at wavelengths that is able to drive photosynthesis may be utilized instead of or in addition to natural sunlight. For example, a photobioreactor apparatus is configured to utilize sunlight during the daylight hours and artificial light in the nighttime, so as to increase the total amount of time during the course of the day in which the photobioreactor apparatus can convert light, $CO_2$ and water to products through use of photosynthetic organisms.

The effect of light on productivity is determined for each photobioreactor design. In preferred embodiments, the photobioreactor panel 100 is generally placed under a desired light intensity for optimal growth conditions using selected light capturing organisms. In various embodiments, the light intensity is between 20 and 5000 $\mu E/m^2/s$. In other embodiments, light intensities of less than 2000 $\mu E/m^2/s$ are used, and in a further embodiment, light intensities less than 500 $\mu E/m^2/s$ are used. Under certain conditions, light is penetrated through the panel 100 or at least partially penetrated to control the depth of light penetration in the panel 100. The photobioreactor panel 100 of the invention minimizes the time that the culture is exposed to "dark zones" that are more apparent in the traditional tubular columns. Preferably, the mixing and flow within the photobioreactor panel is controlled such that optimized, and preferably, optimal light/dark cycling is achieved to maximize the efficiency of the bioreactor. Typically this requires cycling of the organisms between the top and bottom layers of the channels 200 with cycle times shorter than 1 sec. Preferably, dark zones where the culture may be subjected to poor mixing and residence times approaching the minute time scale are essentially eliminated. In various aspects, at least one surface of the photobioreactor panel 100 captures light allowing for maximum light capture for optimum productivity.

The photobioreactor can be illustrated in various dimensions, shape and designs. In preferred embodiments, the panel 100 is a corrugated sheet having a flat-plate design comprising multiple parallel channels 200. The channels 200 allow for continuous flow-through of culture while providing structural support for the panel 100. Additional structural support (e.g., oval contact flats 105) can be implemented, for example through thermoforming. The panel 100 may be in various shapes and sizes and is generally designed to allow a desired amount of light to penetrate the channel 200. A useful feature of the photobioreactor panel 100 allows visible light spectra of wavelengths between 400-700 nm to enter the channel 200 for optimum PAR for the organisms while filtering out the unwanted wavelengths in the spectra.

Certain organisms used in the photobioreactor apparatus may be sensitive to ultraviolet light or radiation, thus, certain portions of the external surface of the panel 100, or alternatively, the entire panel—outer and inner surface may be covered with one or more light filters that can reduce or negate transmission of the undesired radiation. Such filters are integrated into the photobioreactor apparatus design to permit wavelengths of the light spectrum that the organisms require for growth while barring or reducing entry of the harmful portions of the light spectrum. One such optical filter comprises a transparent polymer film optical filter such as SOLUS™. It is recognized that a skilled artisan could employ a wide variety of other optical filters and light blocking/filtering mechanisms for this purpose.

Figure 2:
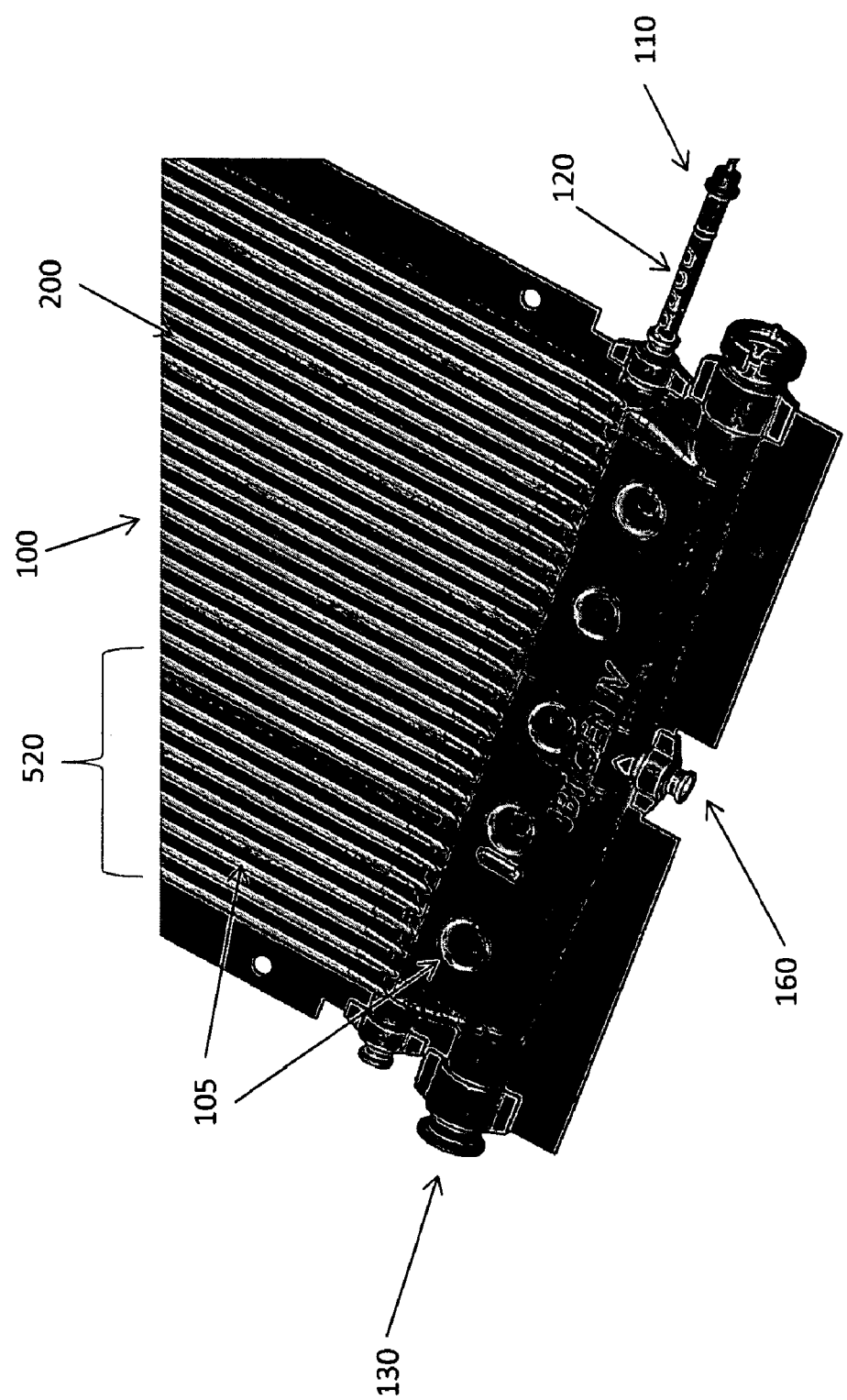
FIG. 2 depicts an enlarged bottom portion of the photobioreactor featuring a removable sparger.

In an alternative embodiment, reflective polymers or materials such as foil, polyester film such as Mylar® can be employed to reflect light to the panel 100 as shown in FIG. 2. In such embodiments, polyester films are placed beneath or along the sides of the panel 100 to reflect PAR back through the channels 200.

In other embodiments, materials may be employed to reflect the spectrum, filter ultraviolet ray or re-emit at an alternate wavelength. Polymers, such as those described in McDonald S A et al Nat Mater 2005 4(2): 138-42 can be used to harvest light above 800 nm. Various polymers have been found that convert UV light to visible spectra light. These polymers have a "whitening effect" by harvesting light above 800 nm and re-emitting light at 400-450 nm, which is peak absorbance of chlorophyll A. They have good thermal stability (>300° C.) and high fluorescent quantum yields (>0.8). Polymers, such as those described herein can be used to convert UV light into light that emits in the spectrum typically absorbed by chlorophyll.

A number of other such UV-to-visible polymers with good photostability exist. They include, for example, 4,4-bis(5-methyl-2-beazoxoazol)ethylene (Hostalux KS-N); 1,4-bis(benzoxazolyl-2-yl)naphthalene (Hostalux KCB); 2,5-bis-(5-tertbutylbenzoxazole-2-yl) thiophene (Uvitex OB); 2,2'-(4,4'-diphenolvinyl)dibenzoxazol; (Uvitex OB-1); 1,1'-biphenyl-4,4'-bis(2-(methoxyphenyl)ethenyl) (Uvitex 127). The choice of a polymer is dependent on its photo-properties, thermal properties, availability and cost.

Polymers can also be co-polymerized by techniques well known to those skilled in the art. See Liu MO Mat Letters 2006 60(17-18) 2132-2137.

In certain aspects of the invention, the photobioreactor can be constructed of any low cost stable building material such as plastics (polycarbonate, polyethylene, polypropylene, chlorinated PVC) that allows light through the panel to drive photosynthesis in the organisms. For instance, such materials can be made of polyethylenes, polypropylenes, polyethylene terephthalates, polyacrylates, polyvinylchlorides, polystyrenes, polycarbonates, thermoplastics, glass, resin-supported fiberglass or plexiglass, etc. In certain embodiments, materials that reflect infrared radiation including but not limited to quartz are used. These materials can be interwoven or used instead of or in addition to other materials used to enclose the panel 100.

Other examples of plastic material are LDPE, linear low density polyethylene (LLDPE), fiber-reinforced LDPE, high-density polyethylene (HDPE), poly vinyl chloride (PVC), polypropylene (PP), single-layer nylon, polyester (PET), ethylene vinyl acetate (EVA), polyvinyledine chloride (PVLC), ethylene vinyl alcohol (EVA), polystyrene (PS) and any other transparent plastic known in the art. Alternatively, since some plastic materials may have an undesirable effect of reacting to certain desired output products, materials such as those that do not react to products, e.g., translucent materials may be used to construct the photobioreactor apparatus. Additionally, any combination of the above materials may be used to create a multi-layer hybrid polymer. Thicknesses of material may vary according to the structural integrity to reduce the cost of the material in constructing the photobioreactor as well as the selected photosynthetic organism grown in the photobioreactor.

Various factors such scalability, flexibility and durability should be considered when selecting for the photobioreactor construction material. For example, the materials should be subjected to variable heat, pressure and allow for turbulence required for light cycling, shear-stress limitations. In some embodiments, materials that prevent cell adhesion are used, for example, biofilms, biocompatible materials, polymers, reduced magnesium ion concentration of the medium (Walach, Marek R., *Appl Microbiol Biotechnol.* Nov. 24, 2004)). Consideration should also be given to ease of cleaning particulates and other undesirable material build-up on the exterior of the photobioreactor.

The photobioreactor material can vary in thickness, depending on the organisms' ability to receive PAR. A preferred example is a corrugated polycarbonate panel 100 having about 1.0-2.0 mm thickness. More preferably, the thicknesses which may be employed in the panel 100 is about 0.10 mm-100 mm, 0.25 mm-50 mm or 1.0 mm-5.0 mm. At such thicknesses, a moderate amount of turbulence within the photobioreactor apparatus would have little effect on its structural integrity while providing the desired level of flow within the channels 200.

To introduce liquid and return the same to the photobioreactor apparatus, in certain aspects of the invention, manifolds (130, 140) are connected to the panel 100. A preferred embodiment for joining the manifolds together with the photobioreactor are thermal plastic welding, adhesives or epoxy set for an appropriate time, pressure and temperature for the materials used. Alternatively, the panel and the manifolds are extruded together or thermoformed.

The surface of the panel 100 and the manifolds (130, 140) can be flat or contoured optimally to control PAR. In one embodiment, the entirety of the photobioreactor apparatus can employ the same material including the various manifolds enclosing the panel 100.

Figure 5:
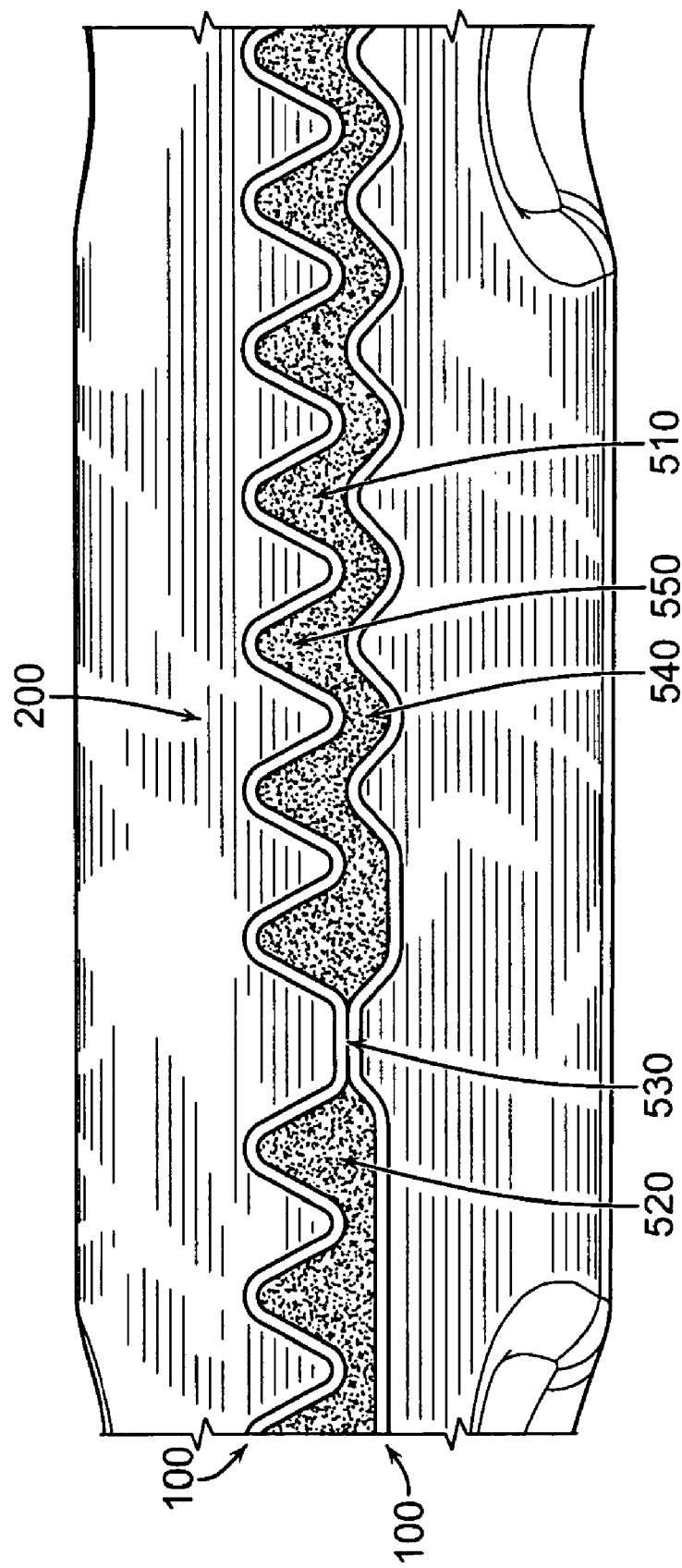
FIG. 5 is a cross-section view along part of the width of the photobioreactor illustrated in FIG. 1.

In preferred embodiments, the reactor structure has a cross-section as shown, in part, in FIG. 5 The cross-section is positioned as indicated in FIG. 1 (see line with arrow, the arrow indicating the viewing direction). The reactor is preferably formed through a thermoform twin-sheeting process. In this implementation, the reactor is not segmented into distinct channels, but rather has a broad upflow (upcomer 510) and downflow region (internal downcomer 520) allowing for enhanced cross mixing. There is a bonded strip 530 that separates the upflow region from the downflow region. This division between the upflow and downflow sections of the reactor typically extends up the length of the active region of the reactor. It also typically serves to bond the top and bottom sheet together. In this view, the left side is the downflow side. In addition, oval contact flats 105 can be included throughout the reactor to locally stiffen the reactor from ballooning under hydrostatic pressure from the culture. The top and bottom walls are wavy, unlike a flat panel bioreactor. The waviness provides several benefits: it further stiffens the walls allowing for thinner plastic sheets, it provides increased surface area on the outside of the reactor that improves heat transfer out of the reactor, for example, when cooling air is blowing along it, and it provides increased exposed surface area of the culture which in conjunction with an overhead light diffuser can decrease the light intensity that the culture is exposed to. As the reactor flow is typically driven with air-lift and the reactor can be operated at an angle less than vertical, air bubbles introduced in the bottom header tend to rise in the peaks of the waves on the top surface. Thus, better mixing and light-dark cycling can be expected in the peak regions relative to the valley regions. The reactor walls are preferably spaced vertically so that for the desired operating OD, most of the PAR light is absorbed in the culture and little PAR is transmitted and lost through the reactor bottom. Spacing the walls more than this can create unproductive dark volume. Since the mixing in the valley regions of the reactor is less optimal than in the peak regions, the vertical reactor gap (i.e., vertical distance between the top surface of a bottom sheet and bottom surface of the top sheet of a reactor structure) is typically smaller in the valley regions to reduce the reactor volume associated with regions of reduced mixing. But the minimum vertical reactor gap in the valley regions is still designed to be sufficient for capturing most of the PAR radiation. From the thermoforming process, all transitions within the reactor can be performed smoothly, enhancing the cleanability of the reactor, reducing contamination issues.

Figure 3:
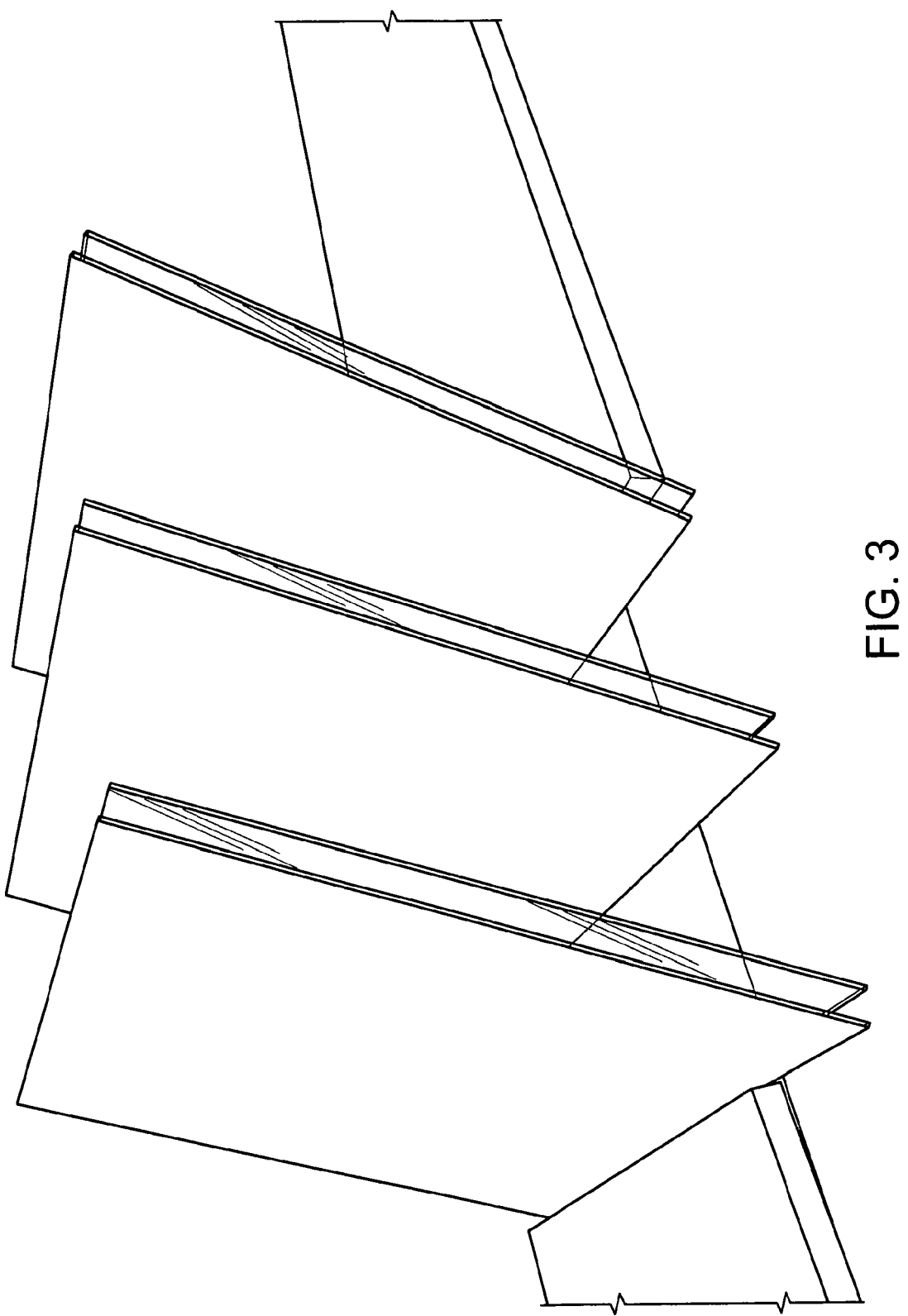
FIG. 3 is a photographic representation of a reflective shield on a photobioreactor.
Figure 4:
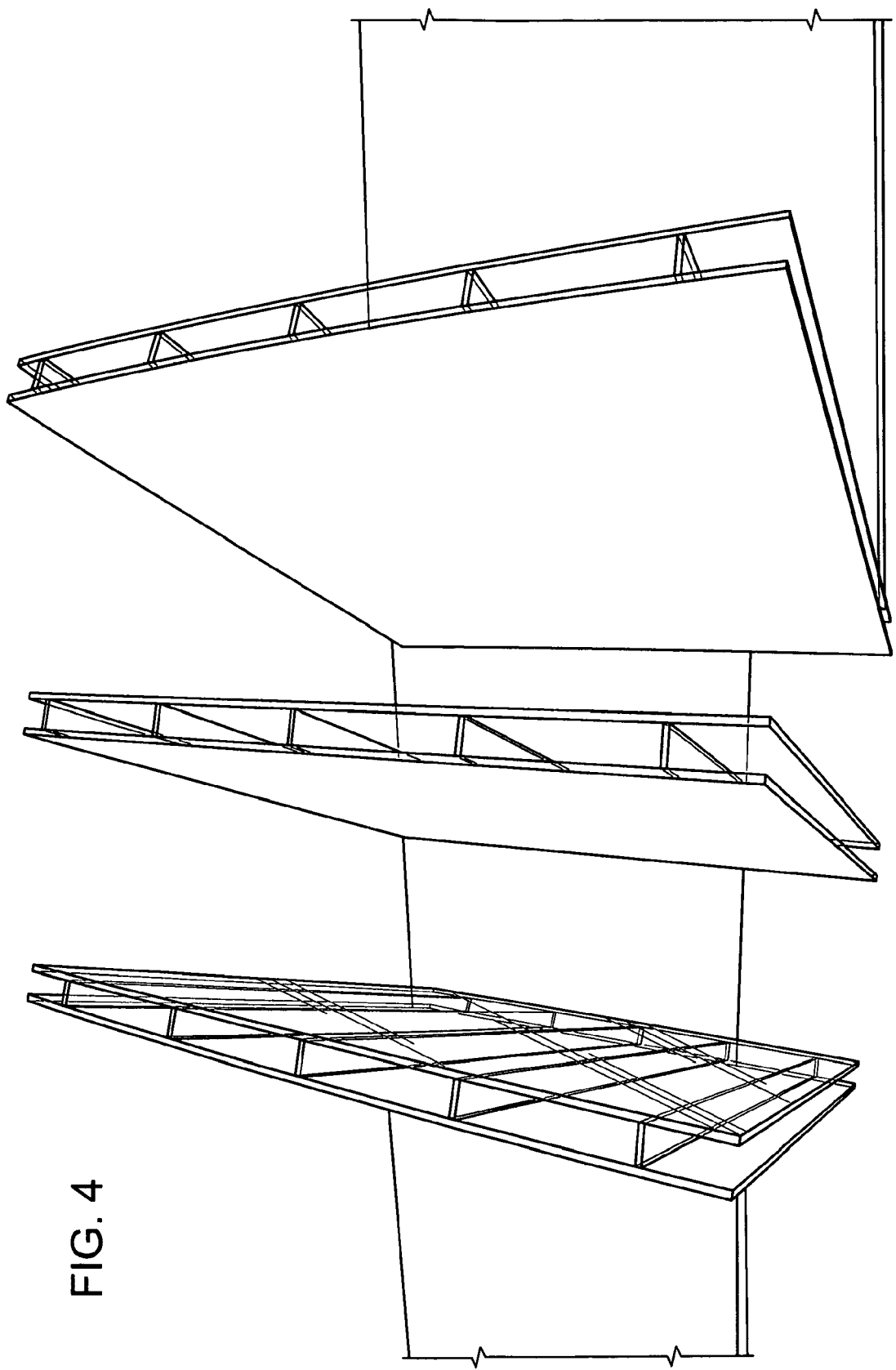
FIG. 4 is a photographic representation of a reflective shield on a photobioreactor.

Another embodiment of the present invention shares the advantages described in the previous paragraph is a photobioreactor comprising a reactor structure for containing a culture medium. The reactor structure includes a top sheet and a bottom sheet which are bonded together to form a reactor volume for containing a culture medium. The vertical reactor gap along at least part of the width (i.e., cross-sectional width as shown, e.g., in FIG. 3) of the reactor structure increases and decreases repeatedly. Preferably, the vertical reactor gap along at least part of the width of the reactor structure minimizes and maximizes repeatedly. More preferably, the vertical reactor gap along at least part of the width of the reactor structure minimizes and maximizes repeatedly while being not smaller than a minimum vertical reactor gap selected such that for an operating OD substantially all (typically, at least 50 percent, more typically, at least 75 percent, even more typically, at least 90 percent, yet even more typically, at least 95 percent) of PAR light transmitted through the top sheet is absorbed in the culture. Even more preferably, the vertical reactor gap along at least part of the width of the reactor structure minimizes and maximizes periodically while being not smaller than a minimum vertical reactor gap selected such that for an operating OD substantially all (typically, at least 50 percent, more typically, at least 75 percent, even more typically, at least 90 percent, yet even more typically, at least 95 percent) of PAR light transmitted through the top sheet is absorbed in the culture. Yet even more preferably, the vertical reactor gap along at least part of the width of the reactor structure varies periodically between a minimum vertical reactor gap and a maximum vertical reactor gap, wherein the minimum vertical reactor gap is provided in troughs of the bottom sheet (i.e., troughs of the internal surface of the bottom sheet) and the minimum vertical reactor gap is selected such that for an operating OD substantially all (typically, at least 50 percent, more typically, at least 75 percent, even more typically, at least 90 percent, yet even more typically, at least 95 percent) of PAR light transmitted through the top sheet is absorbed in the culture. Yet even more preferably, the vertical reactor gap along at least part of the width of the reactor structure varies periodically between a minimum vertical reactor gap and a maximum vertical reactor gap, wherein the minimum vertical reactor gap is provided in the troughs of the bottom sheet, the maximum vertical reactor gap is provided at the peaks of the bottom sheet and the minimum vertical reactor gap is selected such that for an operating OD substantially all (typically, at least 50 percent, more typically, at least 75 percent, even more typically, at least 90 percent, yet even more typically, at least 95 percent) of PAR light transmitted through the top sheet is absorbed in the culture. Most preferably, the vertical reactor gap along at least part of the width of the reactor structure varies periodically between a minimum vertical reactor gap and a maximum vertical reactor gap, wherein the minimum vertical reactor gap is provided in the troughs of the bottom sheet, the maximum vertical reactor gap is provided at the peaks of the bottom sheet, the minimum vertical reactor gap is selected such that for an operating OD substantially all (typically, at least 50 percent, more typically, at least 75 percent, even more typically, at least 90 percent, yet even more typically, at least 95 percent) of PAR light transmitted through the top sheet is absorbed in the culture, the troughs of the bottom sheet are positioned vertically below troughs of the top sheet and peaks of the bottom sheet are positioned vertically below peaks of the top sheet. Further, preferably, the surface of the bottom sheet and/or top sheet changes smoothly. Typically, the maximum vertical reactor gap is between 1 and 10 times the minimum vertical reactor gap. More typically, the maximum vertical reactor gap is between 1 and 5 times the minimum vertical reactor gap. Also, typically, the distance between consecutive peaks of the bottom sheet is between 1 and 10 times the minimum vertical reactor gap. More typically, the distance between consecutive peaks of the bottom sheet is between 1 and 5 times the minimum vertical reactor gap. Also, typically, the vertical reactor gap increases and decreases at least three times, more typically, at least 5 times, even more typically, between 5 and 100 times, and yet even more typically, between 5 and 50 times. Further, the top sheet and the bottom sheet can be bonded along the length of sheets to divide the reactor volume into an upflow volume (upcomer) and downflow volume (internal downcomer).

In further embodiments of the present invention the reactor structure as described in the previous paragraph can be a part of a photobioreactor assembly as described herein and/or include a passive thermal regulation system as described herein. For example, one of these further embodiments is a photobioreactor assembly comprising a reactor structure as described in the previous paragraph, and a greenhouse structure configured to provide a greenhouse environment for the reactor structure, the reactor structure and the greenhouse structure spaced relative to each other to provide temperature control of the photobioreactor. Another example of these further embodiments is a photobioreactor assembly comprising a reactor structure, and a greenhouse structure configured to provide a greenhouse environment for the reactor structure, the reactor structure and the greenhouse structure spaced relative to each other to provide temperature control of the photobioreactor, wherein the reactor structure comprises two spaced apart reactors as described in the previous paragraph and the greenhouse structure comprises a diffuser roof element arranged between the reactors.

In further designs, the photobioreactor has a flexible fitting design conducive to adhesive bonding, ultrasonic welding or insert/functional twinsheet thermoforming as shown in FIG. 1. The photobioreactors are amenable to various dimensions such as lab size (~1.6×4)'~8 L capacity or pilot/commercial (~4×6)'~25 L capacity.

Further, finite element analysis is conducted to optimize structural staking pattern, reduce material thickness and consumption and verify thermal expansion & photobioreactor attachment. Additionally, fluid flow and mass transfer analysis, e.g., computational fluid dynamics create visual internal flow pattern and verify volumetric flow rate through baffle & reactor-to-reactor connecter.

In various embodiments, the photobioreactor apparatus is raised at an angle to most optimally capture light in accordance with various factors depending on for instance light intensity and geographic location. Preferably, the angle is about 10 to 30 degrees relative to the ground. In preferred embodiments, one end of the panel 100 is fixed or pivoted at the base to be freely rotatable, for example to follow the light source during the course of the day. The effect is to create an effective PAR, optimal exposure to light, track the source of the solar energy during the day and throughout the year for maximum biomass yield. A photobioreactor design at a 30-degree tilt can provide fairly uniform yearly insolation in the southwest U.S. for example.

Gas Bubbles for Air-Lift

Various designs can be employed to optimally capture light and efficiently transfer gas to the light-harvesting organisms that are aimed at maximizing cell growth and/or productivity through the use of a photobioreactor apparatus and proper mixing with $CO_2$.

A low-cost efficient mixing system is integrated into the photobioreactor apparatus. In various aspects, bubbles allow for more efficient gas exchange of carbon dioxide uptake and oxygen removal. Use of air and gas bubbles achieves mass diffusion, mixing and pumping with the added benefit of being cost-effective. In certain embodiments, carbon source such as $CO_2$ containing flue gas is sparged into the photobioreactor and exhaust air such as $O_2$ is removed from the system via an exhaust vent 115. In a preferred photobioreactor design with a corrugated panel 100, air bubbles and gas e.g., $CO_2$ are suitable in providing optimal mixing and circulation of culture and media with minimum hydrodynamic force. Furthermore, such aeration exerts little harm to the culture. The bubbles act as a mechanism, e.g., as an air-lift pump, circulating the culture without the need for ancillary pumping. Bubbles are generated by sparging air and $CO_2$ through a sparger 110, which rise to the top manifold 140 relatively quickly. Preferably, bubble characteristics are improved by initiating them at an optimal size.

Figure 6:
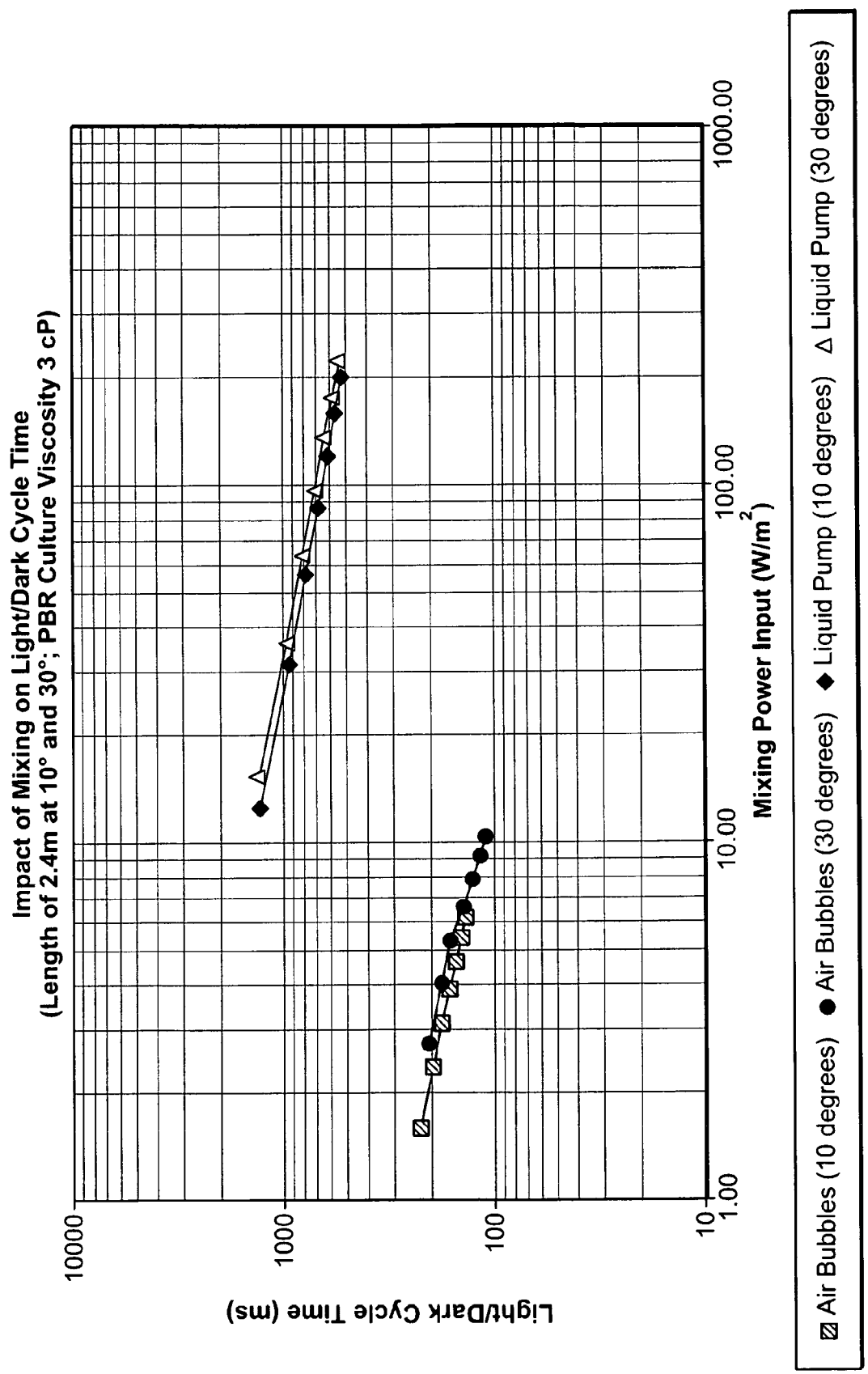
FIG. 6 illustrates the impact of mixing on light/dark cycle time.

In various embodiments, the air-lift used for mixing effectively eliminates large circulation pumps resulting in significant capital and operating costs savings. As shown in FIG. 6 air bubbles are much more effective in promoting radial mixing than simple liquid pumping. Light/Dark (L/D) cycling time of less than 200 ms can be accomplished with very low power input. In certain embodiments, a preferred air-lift design provides sufficient liquid velocity to obtain a pure bubble flow regime. In Example 2, data shown to obtain a light/dark cycle time of order 100-150 milliseconds while using reasonable levels of mixing power shows that the mixing caused by air bubbles in the air bubble lift driven flow is more favorable than mixing associated with turbulent mixing resulting from pumping the liquid. In various embodiments, the conversion of order 80 W/m$^2$ of insolation into product is preferred and therefore it is preferred to use a relatively small fraction of the converted energy for mixing of the culture. Accordingly, the air bubbles provide much more efficient mixing than pumps at the same power while allowing use of a modest amount of total mixing energy relative to the energy conversion to product. The motive force can be provided by other means and various suitable pumps and are known to those of ordinary skill in the art.

Depending on the relative velocities of the liquid medium flow and gas bubble flow within the photobioreactor apparatus, and governing the flow rate, photomodulation frequency of greater or less cycles per second may be achieved. In one instance, a high frequency "flashing light" effect during photosynthetic activity has been found to be very beneficial for growth and productivity of many species of algae (Burlew 1961). Configuring the photobioreactor apparatus with photomodulation, therefore, may provide additional or more extended exposure of the organism to dark, rest periods and may increase productivity.

Figure 8:
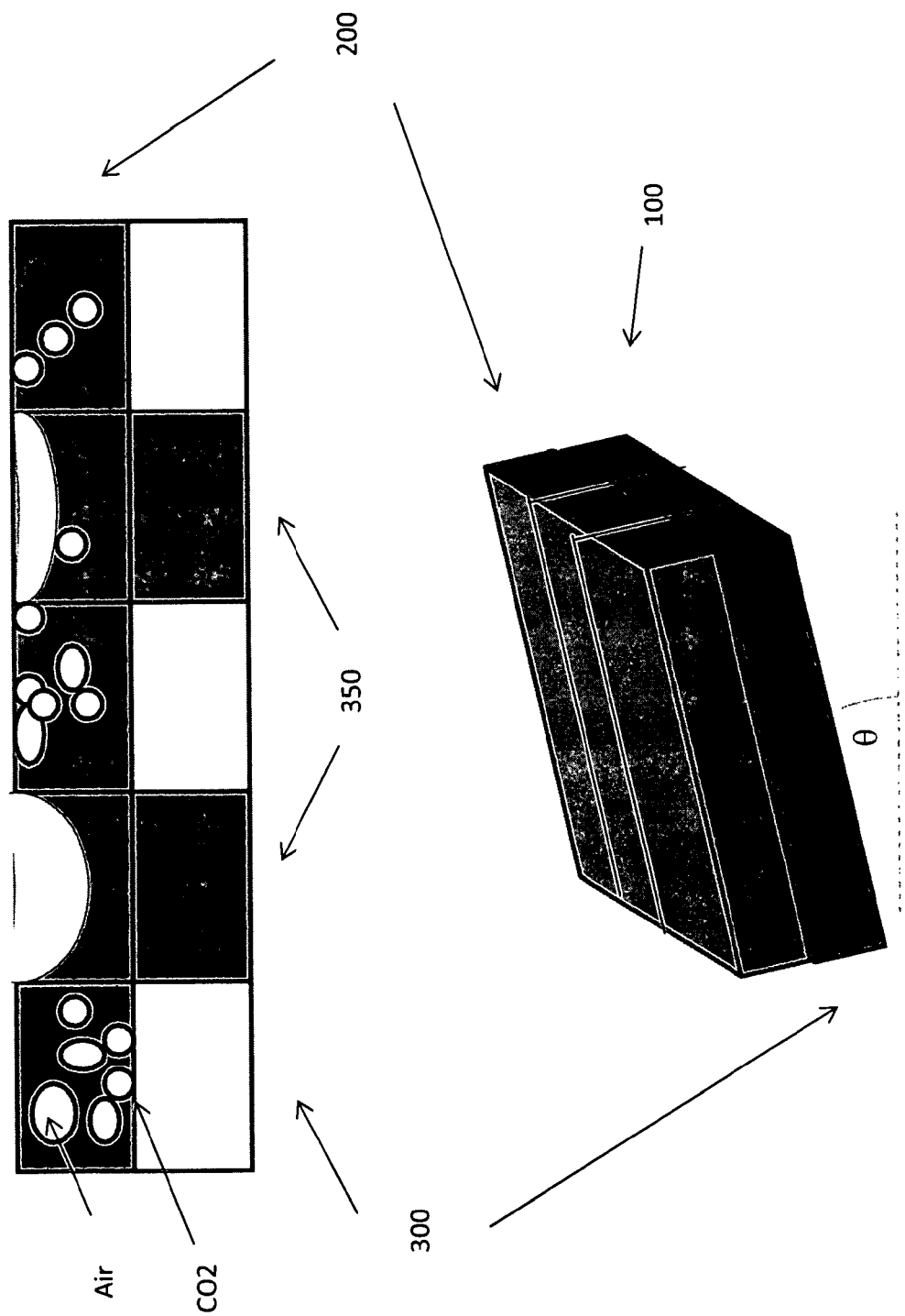
FIG. 8 is a cross-section of multi-layered channels. A side view of the same is shown in the bottom part of FIG. 8.

In certain other embodiments, the photobioreactor apparatus is equipped with controls to adjust the liquid flow direction. For instance, gas is fed to the liquid medium via the apertures 120 using gas spargers 110, which is configured to create a plurality of bubbles rising up to the top manifold 140, thereby inducing liquid flow. In more preferred embodiments, gas spargers 110 are configured and positioned at the bottom of the channel 200 to introduce carbon dioxide so as to create circulation and mixing from various sized gas bubbles that rise up to the surface of the liquid medium contained within the channel 200. The velocity of bubbles is likely to affect the air-liquid interface. In certain instances, the bubbles may collect and as a consequence provide the liquid flow an increased surface area for increased light capture (FIG. 8). Additionally, since bubbles are inherently unstable, stabilizing means such as adding surfactants is contemplated.

Figure 7:
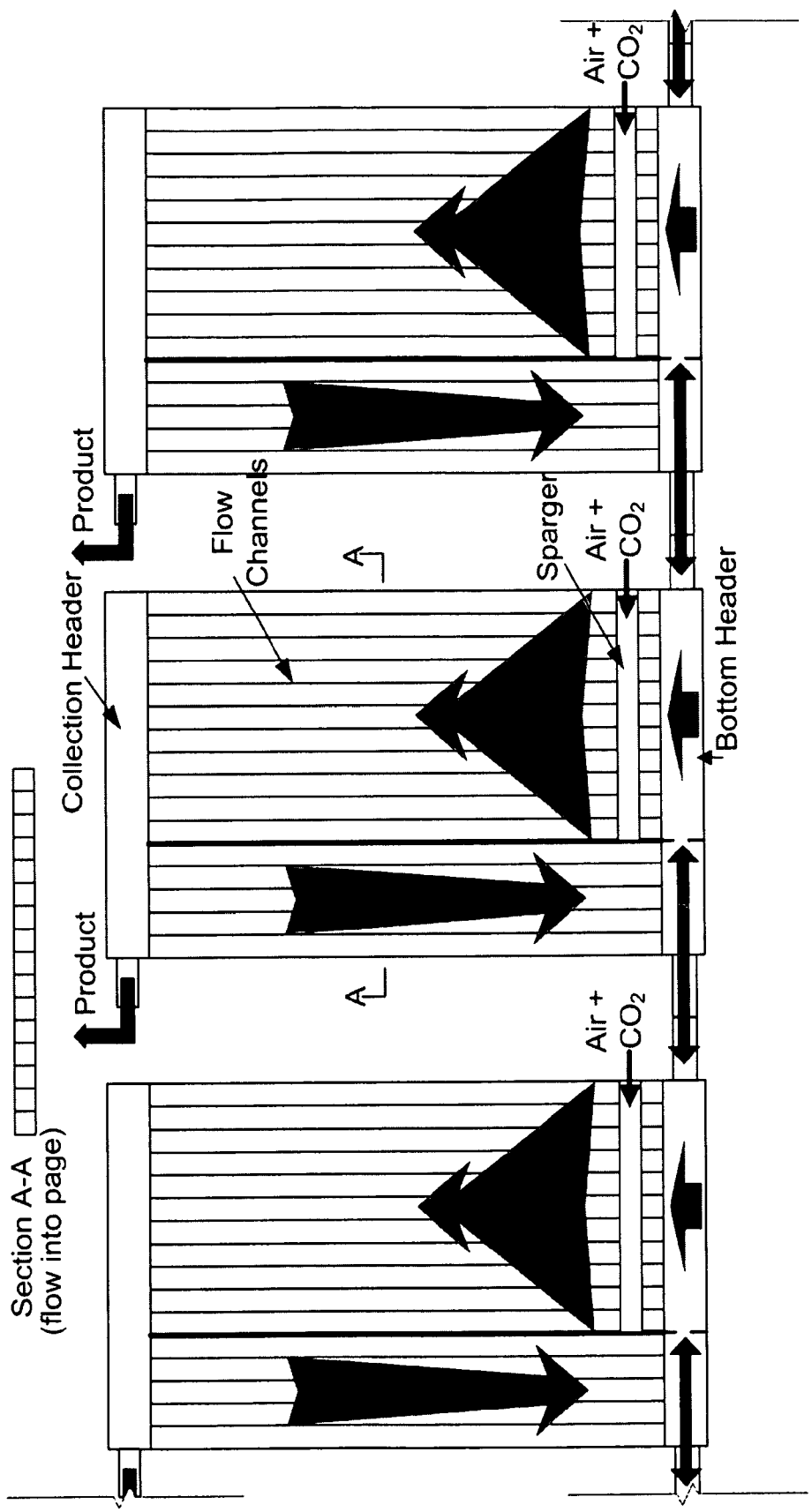
FIG. 7 is an illustration of a multiple photobioreactor assemblies connected in fluid communication, each photobioreactor featuring an internal downcomer providing circulation of media and mixing of cultures.

In certain embodiments, air is sparged into an aperture 120 at a desired pressure e.g., 5 L/m where the bubbles rise upwards through the medium and burst at the air-liquid interface. After the sparged gas creates an upward pressure or lift and forces the culture upwards towards the liquid return manifold 140, the culture is circulated back via a downcomer 520 to the liquid introduction manifold 130. In certain instances, a pump may be included for sufficient liquid velocity and to maintain desired two-phase flow regime. In certain instances, the sizing and flow in the downcomer 520 can be arranged to minimize the residence time of the culture in order to maximize overall productivity and minimize wasteful side-reactions such as respiration under conditions of non-optimal light exposure. Additionally, the downcomer 520 may be either an internal or external feature of the photobioreactor. A downcomer provides internal circulation within the photobioreactor. FIG. 7 shows multiple integrated photobioreactors in fluid communication, each with an internal downcomer 520. One notable advantage of an internal downcomer is the ability to culture the light capturing organisms and transfer to the next photobioreactor unit while maintaining exposure to the light source thereby increasing productivity. Additional advantage includes a setup where the downcomer is fully integrated in a single unit reducing complexity, parts and costs.

A desired amount of light is exposed to the photobioreactor and gas is sparged at a specific interval, which is a function of cell productivity. Residence time is governed by the height of the channel, the initial speed, and pressure of gas injected into the channel. The pumping rate is defined by the flow rate of the gas per the residence time of the bubble to travel the distance of the channel to keep the reactor in steady-state. Bubbles achieve the desired result of mixing and mass diffusion but generally, the bubbles will rise to the surface of the channel fairly quickly. Studying of the fraction of channel residence time of air bubbles of various diameters that rise to the top of the channel indicates the optimal bubble size to be about 0.5 mm to about 2 mm. In various embodiments, bubbles are generated at a desired initial diameter, for instance, to about 1 mm, however, bubble sizes can vary dramatically. Alternatively, the desired initial bubble size may be larger to create a greater surface area of the culture in the channels for better light capture.

In certain instances, media may run countercurrent to the sparged air in the channel 200 but such downward movement media flow can be minimized. As such, the culture may experience co-current and counter-current gas exchange during circulation.

In various embodiments, the photobioreactor is at a particular angle. For instance, the photobioreactor tilt optimum may be at 30° (FIG. 8). This has shown to provide fairly uniform yearly insolation in the southwest U.S. Modifying or adjusting the angle of the photobioreactor apparatus may improve performance. Changing the angle may be performed manually or automatically according to a set of instructions and/or calculations and/or in response to values from various sensors (e.g., temperature sensors or light intensity sensors). Realtime control of the positioning of the photobioreactor apparatus may be facilitated as part of the computer-implemented control strategy.

In certain embodiments supplemental pumping may be required as a result of the incline while in other embodiments, the air-lift pump is sufficient to provide the needed pumping for circulation. Additional riser height may not be effective in increasing pumping due to increased pressure loss associated with riser piping. Increasing riser piping diameter to reduce pressure loss may result in substantial dead volume for the cells.

Photobioreactor Operation

The bioreactor assembly is connected to a gas introduction manifold 110 to sparge air and gas about 1-3% $CO_2$ to each channel 200. The panel 100 is also connected to a liquid introduction manifold 130 where the culture and media are introduced through an inlet 160 optionally via a peristaltic pump to the panel 100. The air bubbles and $CO_2$ culture mix the culture and is passed through the channels 200 to a liquid return manifold 140. The return manifold 140 may comprise a gas exhaust 115 to vent $O_2$. Alternatively, the culture may be optionally circulated via a pump, through a heat exchanger and through a probe block to measure OD, pH and temperature. The culture can be diverted via drain valve. Products can be released through an extraction valve for separation or collection. The return manifold may also connect to a separator, collector or a condenser. Removal or extraction of desired products of interest can be from either the liquid or gas phase. Any such product can be collected by this mechanism or by a separate mechanism.

Figure 10:
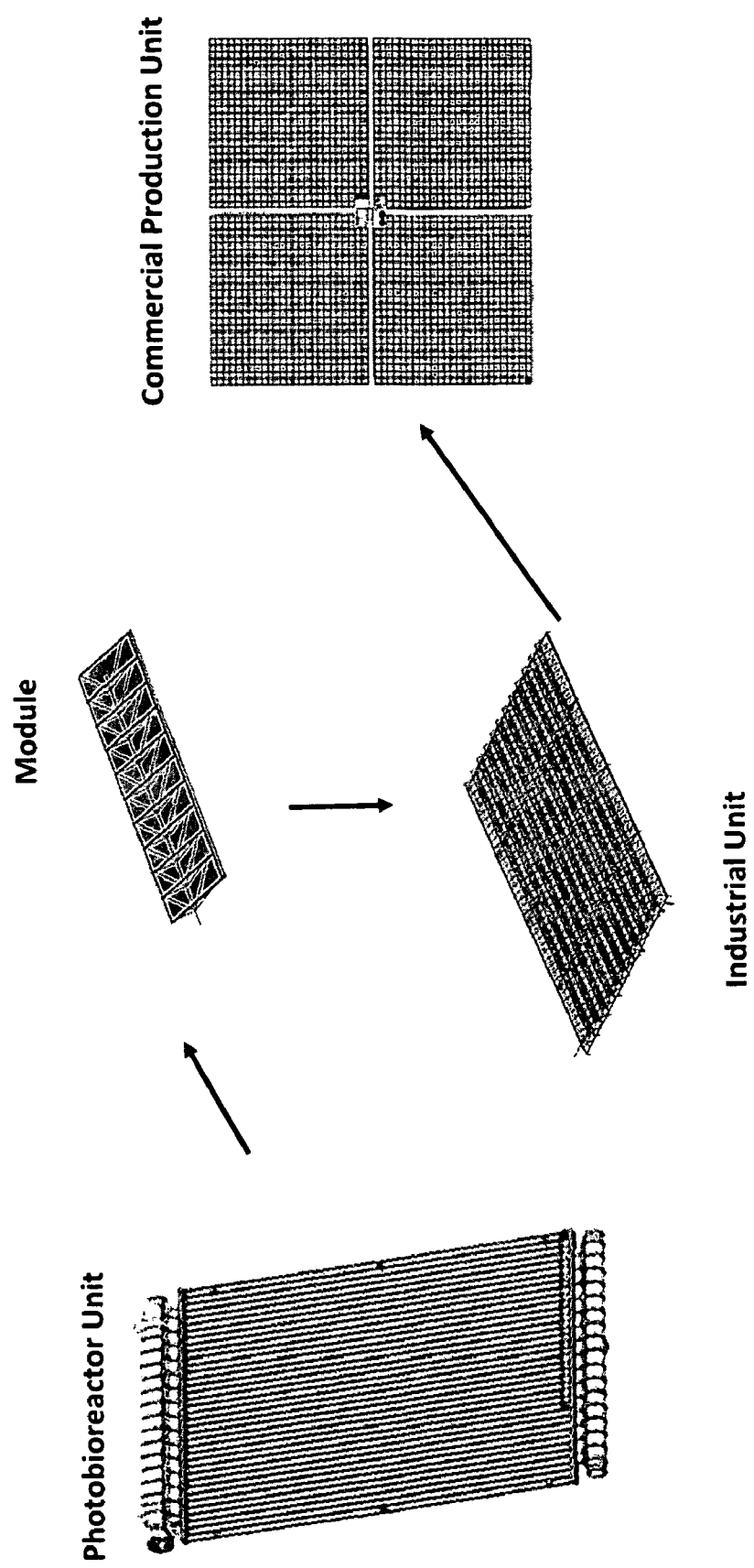
FIG. 10 depicts a scaled, aerial view of a 1,000 acre solar biofactory incorporating the flat-panel photobioreactor apparatus.

In various embodiments, multiple units of the photobioreactor apparatus can be assembled together in modular fashion with relative ease. An example of a multiple photobioreactor apparatus assembly is shown in FIG. 10. After the initial sparge of air and gas, using the air-lift created by the sparged air and gas bubbles, the high pressure of the liquid return manifold 140 (top) of a first panel 100 moves the culture to the low pressure liquid introduction manifold 130 (bottom) of a second panel 100. A series of panels can be assembled to take advantage of this cost-effective and efficient pressure gradient.

Various control points regulate operation of the photobioreactor assembly. For instance, temperature is controlled by thermal management system of the invention. Additionally, pH can be controlled by $CO_2$ concentration. The optical density can be controlled to maintain optimal cell concentration and nutrient profile can be based on feed-forward control. Minimal overpressure to maintain sanitary operation and air flow can be controlled to achieve mass transfer and stripping.

As for control instrumentation, degree of localization of instrumentation and overall automation structure for large solar field is optimized and instruments are minimized or consolidated to achieve low cost but reliable automation at lowest level possible with data aggregation to central computer systems.

Circulating and Media Recycle

In various embodiments, culture is moved from the bottom of the channels 200 up to the height of the top of the channel 200—the liquid return manifold 140 by the gas bubbles as described earlier and then dispersed down through a downcomer 520 connecting the liquid introduction manifold 130 the channels 200 and subsequently returned to the channels 200. In other preferred embodiments, culture collected at the liquid return manifold 140 is recycled and recirculated via a separate panel 100.

In certain embodiments, various conduits are integrated to the photobioreactor apparatus. For instance, media may be passed through various conduits to regulate temperature through a heat exchanger or a water basin. Conduits may block light to employ organisms to undergo light-dark cycle. Gas can be pumped through tubing such as condensation resistant tubing to various inlets. A conduit may be constructed with a variety of suitable materials such as chlorinated PVC, copper, stainless steel or brass. As light is used by reactor placement, the materials can be opaque, and as such, any conduit or fluid piping material known in the art can be used. Tubing that resists biofouling, photoinhibition or those commonly used in fermentations is used.

The internal diameter or minimum internal cross-sectional dimension of conduit will depend on a wide variety of desired operating conditions and parameters and should be selected based upon the needs of a particular application. In general, an appropriate inner diameter of conduit can depend upon, for example, desired volumetric or production capacity, impact of turbulence on cells (although certain cells are known to be sheer tolerant), and the resistance of materials to biofilms.

Furthermore, while the culture is in the photobioreactor, a certain volume of water or other liquid are added in order to compensate for evaporative losses or media/water not otherwise recycled through the system. Water and other liquids can be added via the inlet 160 on the liquid introduction manifold 130. By contrast, effluent can be removed after being filtered and the desired materials can be siphoned off to a separate collector.

Fouling can harm the overall sterility and efficiency of the photobioreactor apparatus and its components. To reduce or avoid it, in some embodiments the photobioreactor apparatus is easily cleanable and be as smooth as possible. Accordingly, in various embodiments, the materials and devices selected are resistant to biofouling to achieve a self-cleaning effect.

Input Sources—$CO_2$ and Water Recycle & Removal

Figure 9:
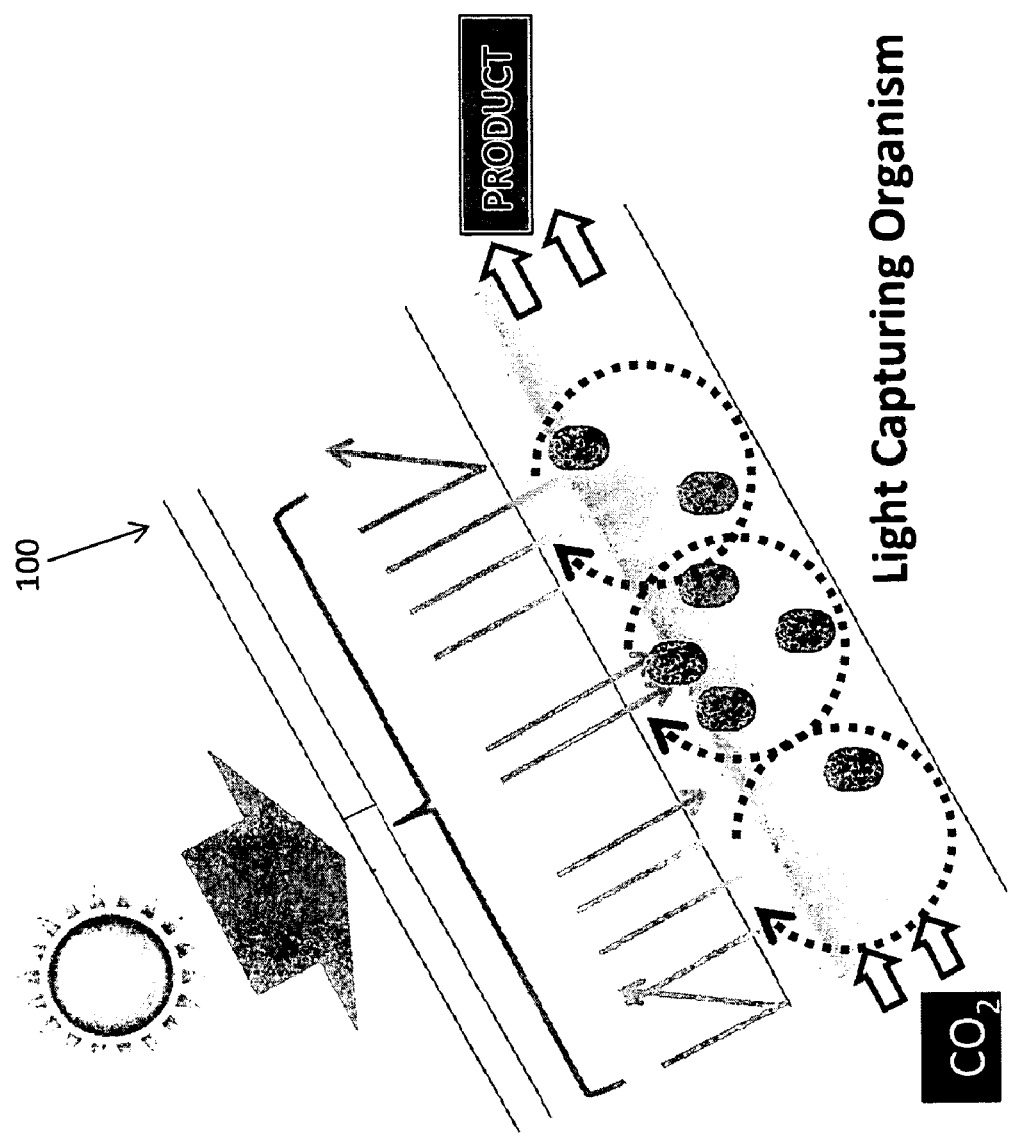
FIG. 9 is an expanded cross-sectional view of culture in media in a photobioreactor as illustrated in FIG. 8.

The photobioreactor system is designed to produce desired carbon-based products including biomass and chemical intermediates as well as biologically produced end products such as fuels, chemicals and pharmaceutical agents and other compounds from minimal inputs: light, water and carbon dioxide (FIG. 9). Input gas can be used from a number of sources including ambient air, concentrated sources, and industrial sources. Carbon dioxide can be supplied from a source where the carbon dioxide would otherwise be emitted into the atmosphere. In certain embodiments, the gas used comes from a source wherein the carbon dioxide concentration is significantly higher than that found in the atmosphere (0.03%). In particular, such concentrations of carbon dioxide can be found in the effluent, flue gas or offgas streams of coal plants, refineries, cement factories, distillaries, breweries, natural gas facilities, breweries, pharmaceutical plants, chemical processing plants, any plants that produce greater than ambient carbon dioxide and the like. Offgas from an example coal plant is at 50-55° C., and is composed of 10.9% $CO_2$ 0.01% CO, 9% $H_2$, 3.01% $CH_4$, 3.0% $O_2$, 0.106% $SO_2$, 74% $N_2$. Concentrations of the various elements can change based on operating parameters as well as from facility to facility.

The integrated solar biofactory can be adapted to treat such emitted gas and provide air pollution control and renewable energy solution to fossil fuel burning facilities, such as power generating facilities. The solar biofactory also comprise emissions control devices and regeneration systems that can remove undesired gases and other pollutants from the environment.

Carbon capture and sequestration (CCS) from power plants and various other sources at present is a costly and energy intensive endeavor, however, the integrated solar biofactory provides an alternative to CCS and provides a means for converting carbon dioxide into fuels and chemicals in scale. Accordingly, the method provides for accounting for or more preferably receiving carbon credits comprising: culturing light capturing organisms in a photobioreactor or photobioreactor assembly using carbon dioxide, light and water; measuring the input, use or reduction of carbon dioxide that is captured by the photobioreactor; and determining an amount of carbon credits based on the input, use or reduction of carbon dioxide.

The gas at an inlet can be at the same, greater, or less pressure than as released as it would for the offgas streams. Higher than ambient pressures can be used for fluid movement within the photobioreactor apparatus as appropriate.

In certain embodiments, the gas sparged into the photobioreactor channels 200 moves cocurrently with the media. After passing through channels 200, the gas exits the chamber through gas exhaust vent 115. These outlets may release directly into the atmosphere, or connect to gas conduits. In some embodiments, the gas conduits reconnect to the gas inlet allowing for gas recycle. In some embodiments the recycling gas conduits also have a system allowing for separation of elements in the gas phase. The outlets and conduits may also be regulated as to maintain desired pressures and concentrations in the photobioreactor.

In those cases where no conduit, recycle, or collection system exists, the gas is released directly into the surroundings. In various aspects, oxygen is primarily exhausted from the photobioreactor and therefore does not accumulate.

In those cases where the gas is recycled, anywhere between 0 and 100% of the gas removed from the photobioreactor can be returned with the balance released directly into the surroundings. The amount released can be controlled to reach desired reactor conditions. The amount not released defines the recycle rate. In some embodiments, not all of the gas is recycled such that various elements harmful to achieving maximal productivity, such as oxygen, can be removed. The recycle can be before or after separation of gas elements into one or more components. As such recycle does not necessarily refer to the gas as a bulk but as a relative amount to the gas removed from the photobioreactor. Recycled gas is then blended in some proportion with gas at the gas inlet of the appropriate reactor system to achieve the desired reactor conditions.

Water useful in the solar biofactory can be no-salt, low-salt, brackish, marine, or high salt. The water can derive from natural stores (e.g., lakes, rivers, ponds, etc) or from processed streams.

There are numerous recognized advantages in the solar biofactory as for example it optimizes land use, excellent (preferably maximum) light capture and distribution, efficiently controls heat, low cost, within a closed culture, has flexible design, scalable and ease of construction, good volume, optimal mixing, cost-effective means of pumping, requires minimal inputs and it obviates the need for added steps to convert biomass to their component sugars. The focus from feedstock has shifted to renewable and lower cost sources of biomass, for example, the use of non-starch, non-food-related biomass such as trees, grasses, and waste materials. The largest components of these biomass sources are cellulose, hemicellulose, and lignin. The focus on these sources still falls short in comparison to the solar biofactory system as they employ steps for hydrolyzing biomass, mechanical milling, dilute-acid thermochemical pretreatment and other such methods to convert biomass into their component sugars. The solar biofactory can achieve highly efficient productivity with light capturing organisms using light, carbon dioxide, and water as inputs.

Photobioreactor Scale Up

FIG. 10 represents a schematic aerial diagram of a novel solar biofactory composed in part of multiple photobioreactor apparatuses. A scalable design for cost-competitive production of biofuel should be low cost, easy to construct, assemble and require considerably less capital and maintenance costs. In various embodiments, the photobioreactor apparatus is scalable to about any volume, e.g., 1 to 90,000 L, easily connected in fluid communication to a separate vessel or reactor allowing easy assembly of a multiple photobioreactor design. In various embodiments, the photobioreactor is about 10 to about 1,000 L.

In certain aspects of the invention, the photobioreactor is configured to a particular dimension, e.g., 4 ft×8 ft ("cell"). Such individual cells are in fluid communication and configured to cover 200 $m^2$ as a Circulation Unit. More preferably, the Circulation Units are assembled modularly to 1000 acres yielding 27.5 mM Gal as shown in FIG. 10.

A single photobioreactor unit can be employed as the same basic building block for full-scale eliminating scale-up risk. For instance, multiple photobioreactor units approximately 4 ft×8 ft are connected together into a 40' module for simplified logistics and installation. Approximately 60 photobioreactors can cover about 2000 sq ft (200 $m^2$). An industrial unit of 0.4 acre includes full process functionality and is simply multiplied to increase capacity. A Commercial Production Unit can comprise 2500 industrial units, covering approximately 1,000 acres (2 km×2 km). At scale, it is capable of producing 27.5 mM gallons of EtOH for example. Industrial unit can be multiplied to any desired size based on land and $CO_2$ availability.

A distillation plant can be located nearby to collect, process or refine the final product.

The solar biofactory can be placed in a number of locations, preferably near a flue gas source, where light is ubiquitous as intensity varies by location and land area, preferably next to a water source. In various embodiments, the photobioreactor apparatus is above ground or in the ground or even in the ocean.

In various aspects of the invention, the solar biofactory can be either open or closed.

In certain embodiments, the solar biofactory is a closed system. In various embodiments, can be aseptic and overcomes the common light penetration limitations. In alternative embodiments, a water basin is placed adjacent to the photobioreactor apparatus to regulate temperature. For instance, the culture can be circulated through a water basin.

Photobioreactor Biomass Productivity

The solar biofactory also provides methods to achieve organism productivity as measured by production of desired products, which includes cells themselves.

The desired level of products produced from the engineered light capturing organisms in the solar biofactory system can be of commercially utility. For example, the engineered light capturing organisms in the solar biofactory system convert light, water and carbon dioxide to produce biofuels, biomass or biochemicals at about 1 g/L per 12 hr day or in certain embodiments, about 2.5 g/L per 12 hr day or greater. Similarly, the engineered light capturing organisms in the solar biofactory system convert light, water and carbon dioxide to produce chemicals, carbon-based products of interest or pharmaceutical agents at about 5 g/L per 12 hr day or greater.

In certain preferred embodiments, the photobioreactor produces about 10 g/L DCW biomass, or about 13.7 g/L DCW biomass. In one instance, an areal productivity of 79 g/m$^2$ per 24 hours has been demonstrated in 5 L lab prototype corrugated flat-plate photobioreactor.

The photobioreactor system affords high areal productivities that offset associated capital cost. Superior areal productivities are achieved by: optimizing cell culture density through control of growth environment, optimizing $CO_2$ infusion rate and mass transfer, optimizing mixing to achieve highest photosynthetic efficiency/organisms, achieving maximum extinction of insolating light via organism absorption, achieving maximum extinction of $CO_2$ and initial product separation.

Figure 11:
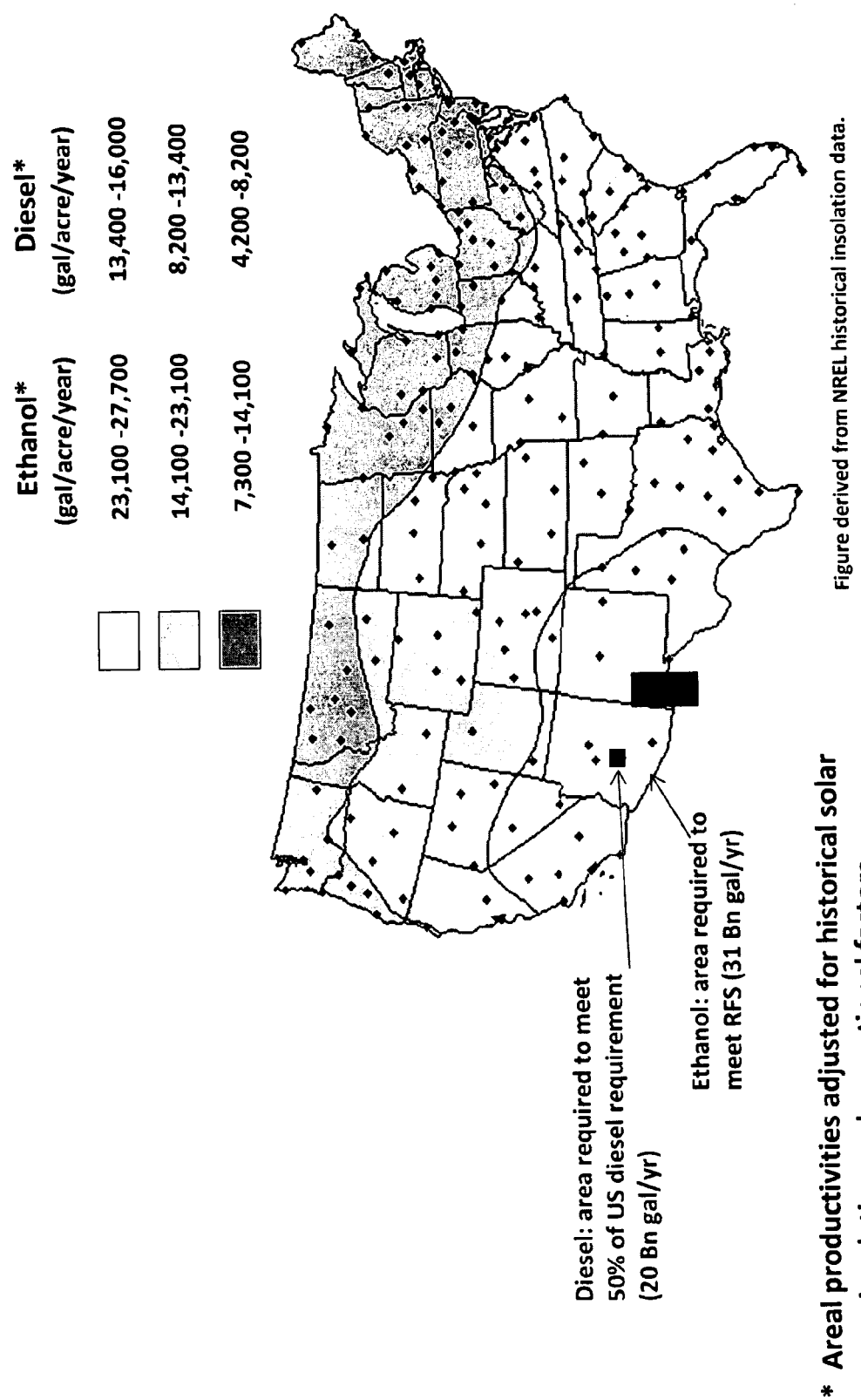
FIG. 11 is a map of the U.S. solar insolation for projected productivites.

In particular, southwestern US has sufficient solar insolation to drive maximum areal productivities to achieve about > 25,000 gal/acre/year ethanol or about >15,000 gal/acre/year diesel although majority of the US has insolation rates amenable to cost effective production of commodity fuels or high value chemicals (FIG. 11).

Furthermore, $CO_2$ is also readily available in the southwestern US region, which is calculated to support large scale commercial deployment of the invention to produce 120 Bn gal/year ethanol, or 70 Bn gal/year diesel.

Temperature Control & Heat Balance

In various embodiments, it is important to control the temperature within the photobioreactor apparatus for culturing organisms during operation. Generally, the temperature of the liquid medium within the photobioreactor apparatus should be maintained between about 5° C. and about 60° C., between about 30° C. and about 60° C., and in some embodiments, between about 37° C. and about 60° C. Temperature can be easily regulated and maintained depending on the organism used in the photobioreactor apparatus for optimal growth, circulation and productivity.

When using solar inputs, infrared light, which is not usable, if not otherwise reflected or converted, will produce heat. Other light inputs that are not used or reflected may also contribute to heat, but not with the same magnitude. A number of means can be used to enable temperature regulation. The input gases represent another potential heat source. If carbon dioxide is being used from the offgas of plants, its temperature is typically about 50° C. to 60° C., and therefore represents a second heat source. Mechanical devices necessary for the fermentation or culturing can also be another source of heat. The cellular processes are contemplated to be net endothermic and should therefore not significantly contribute. As the cells require specific temperature ranges for optimal function, temperature control is important to the reactors. A number of means can be used to control the temperature of the photobioreactor based on the total heat needs of the reactor and the various other means being employed. For example, if the infrared contribution is eliminated, the reactor system no longer requires active cooling through heat exchangers or other means, but can be maintained with fluid control and evaporation alone.

Other means of cooling include evaporative cooling, reducing the gas recycle (e.g., requiring more external fluid to be added at a lower (ambient) temperature, or heat exchanger. A heat exchanger may be employed to maintain the bioprocess at a constant temperature. Heat exchangers as well as fluids can be used to compensate for evaporation losses as the temperature is likely to be lower than around 40 to around 60° C.

Evaporative cooling techniques can be employed, as the need for a separate operating equipment is obviated. In some embodiments this can include distributing cooling water over the top surface of photobioreactor using a distribution pipe or sprays and optionally collecting the water in a tray at the bottom of the photobioreactor. Reduced recycle may be used, but has a higher cost given the need for potentially large supplies of water. As a further alternative, carbon dioxide can be stored as dry ice and used for cooling purposes.

A drawback of various closed photobioreactor systems is the significant amount of water consumption and the potential use of evaporative cooling towers, fans, circulation pumps and the associated electrical costs. In certain aspects, the solar biofactory is advantageous in reducing the cooling load and the electrical load. For instance, the photobioreactor panel 100 can be layered on top to create a multi-layered panel as shown in the bottom part of FIG. 8. In various embodiments, water is circulated through a select few channels 350 while other channels 300 remain empty. In such embodiments, the culture is circulated through only the channels 200 of one panel 100. Variations of such embodiments are possible, for instance, to alternate channels (e.g., one out of every four channels) that circulate water as well as varying the layers of panels to regulate temperature.

In various embodiments, thermophiles are used in the photobioreactor running at 60° C., which will allow 100% of heat to be rejected under hottest summer conditions with passive radiation and natural convection without any assistance. In preferred embodiments, low grade heat at 60° C. is also usable to drive EtOH distillation without external source of heat. In other embodiments, water in pond or the like is used to absorb heat during the day and cooling at night passively or actively. Other options are use of material to reduce or reject heat or other suitable means of insulation required at night. In preferred embodiments, a culture comprising a single organism is run for the entire year. Alternative embodiments allow use of mesophile during winter and thermophile during summer to optimize process.

Thermophiles can be cultured in the photobioreactor apparatus at 60° C. during operation and 35° C. during nighttime "cooling" operation. An alternative could be to run the photobioreactor at 50° C. Mesophiles can be cultured at 37° C. during operation and at 15° C. during nighttime "cooling" operation. Another approach is to culture thermophiles in the photobioreactor in the spring, summer and fall and the mesophiles in the winter.

In certain embodiments, thermal storage system is employed to store heat during the day and cold at night. Preferably, the required amount of external heat/cooling is minimized but the photobioreactor apparatus can be designed to require only external heat.

In certain embodiments, the solar energy absorbed and rejected by the photobioreactor varies over the course of a given day and at different times of the year.

In other embodiments, the photobioreactor system may include a heat source, a cooling source or a combination of both. Under conditions, for example during nighttime where the temperature drops, heat is preferable.

In certain aspects, heat is added to the photobioreactor system taking into consideration various factors such as solar irradiance inputs such as latitude/longitude, day, time, plate tilt angle, earth's orbit and atmosphere and adjusting for reflective losses. In other aspects, the output heat is natural convection or radiation.

In other aspects, alternative for heat rejection and non-PAR photon utilization include light scattering pigments with concentrating pV (MIT), thermal electrical couples, piezo electrical couples (thermal expansion etc.), selective coatings etc., pumps, sensors and control systems were integrated into the system. Various components in systems integration include for example, the use of a water basin for thermal regulation.

Photobioreactor & Passive Thermal Regulation

Various embodiments of the invention concern a process for converting $CO_2$ to various products of interest. A novel feature is the integration of a passive thermal regulation system to obviate the costly implementation of heat exchange used in photobioreactors.

The use of the passive thermal regulation system in an enclosed photobioreactor has distinct advantages for the production of fuels and chemicals using various host cells of interest. It has the further advantage of enabling growth of engineered phototrophic strains.

The ability to produce a chemical or fuel product directly from sunlight and $CO_2$ dramatically improves the economics of the process by eliminating costly and inefficient separation, chemical conversion of the biomass and also obviates the need to develop new markets for significant quantities of biomass co-product. A photobioreactor that optimizes the expression of the end-product at the same time as allowing separation of the product directly from the broth (i.e. continuous product removal) dramatically improves the economics such that the increased capital cost of the enclosed photobioreactor is fully justified.

Certain embodiments of the proposed solar biofactory overcomes all of these limitations: photon conversion efficiency, overheating, radiative and convective losses, excessive cooling, low productivity or even an extensive lag at the start of the next daylight cycle and in extreme conditions results in freezing with extensive damage to the culture and the photobioreactor itself and for the first time allows for cost competitive production of fuels and chemicals using only sunlight and $CO_2$ (and minor quantities of additional nutrients) to produce end products (fuels and chemicals) using engineered phototrophs using passive heating and cooling exclusively or essentially exclusively whilst eliminating external sources of cooling and heating. In certain embodiments, the invention further separates the end-product continuously with the production culture being effectively immobilized in the photobioreactor eliminating costly separation and handling of relatively low concentration of biomass (e.g. less than 20 g/L, less than 10 g/L and especially less than 5 g/L). Rather than exchanging the heat that is absorbed by the culture with external utilities natural heating and cooling is used to manage the heat load dynamically through an optimized photobioreactor assembly that combines a real time adaptive control system to continuously adjust the inclination of photobioreactor units based on multi-wall plastic panels that can absorb sunlight and heat in a controlled manner throughout the day and night to regulate temperature to maintain optimum productivity. To accomplish this, the photobioreactor units have engineered surface coatings including but not limited to a reflective heat shield on one side. Additional features include a ground surface coating or material (e.g. sand) that creates diffuse reflection of visible light while selectively trapping IR as heat to limit heat gain of the photobioreactor during the day while allowing heat preservation of the photobioreactor at night by rotating the photobioreactor panels to face the ground with the reflective shield facing upwards minimizing radiative losses. These features and additional embodiments are described in more detail below. It should be realized that several variations are possible that will become obvious to these skilled in the art when considering the general concept of a photobioreactor that manages incident solar radiation in a passive manner. Non-limiting examples include: pigments dispersed in plastic to reject UV, fluorescent pigments dispersed in plastic to up-shift non-usable wavelengths to visible light (e.g. UV to PAR shift), pigments such as organic solar concentrators integrated with photovoltaics to generate electricity with part of the spectrum, IR reflective coatings to reject heat, and IR absorptive materials as groundcover to serve as passive heat sink during the day that can be used at night to release heat.

Selective thin film pV coating to convert portions of the spectrum that are not efficiently or less efficiently converted by the phototroph to create a hybrid fuel and electricity photobioreactor.

In various aspects, materials such as acrylic used to assemble the photobioreactor are adapted to have certain characteristics, which can be exhibited depending on changes relative to the light intensity. For instance, the material may turn more translucent or even opaque at a higher light intensity and reject excess light thereby rejecting excess heat. By contrast, the material may turn more transparent or even clear at a lower light intensity. In preferred embodiments, pigments, dyes or thin films are incorporated into the acrylic. In various embodiments, pigmented acrylic panels are extruded during the photobioreactor manufacturing process. Similarly, materials that are adapted to be sensitive to various other parameters such as temperature fluctuations, weather patterns, pH changes are within the scope of this invention.

Photosynthetically Active Radiation

At maximum photon conversion efficiency approximately 20-25% of PAR (photosynthetically active radiation) or 10% of the total sunlight spectrum can be converted to useful chemical energy depending on the exact composition of the biomass or chemical or fuel product targeted (Pirt, J. "The thermodynamic efficiency (quantum demand) and dynamics of photosynthetic growth", New Phytol. (1986) 102:3-37). Certain phototrophic cultures selectively reflect some portion of the IR wavelengths (approximately 40% of IR above 750 nm) (Gitelson, A. et al "Photic volume in photobioreactors supporting ultrahigh population densities of the photoautotroph *Spirulina platensis*" Applied and Environmental Microbiology (1996) 62:1570-1573). Therefore, the bulk of the incident sunlight to a photobioreactor is ultimately converted to heat that has to be removed to maintain optimum culturing conditions and even avoid total loss of the culture due to overheating. The opposite effect occurs at night when radiative and convective losses results in cooling of the culture volume. Excessive cooling could damage the culture, result in low productivity or even an extensive lag at the start of the next daylight cycle and in extreme conditions results in freezing with extensive damage to the culture and the photobioreactor itself. To protect against both conditions both heating and cooling is typically required to control the photobioreactor temperature. The implications of these heat gains and losses are further detailed in FIG. 13 which shows net heat absorbed and FIG. 12 which shows heat flux integration. The magnitude of the heat flows involved essentially limits the application of current enclosed photobioreactor technology to very temperate climate zones or small units that can make effective use of inexpensive waste heat that may be locally available (e.g. from the power plant or factory supplying the $CO_2$). During warmer days the cooling requirements of a 1000 acre facility would be of similar order to that of a 600 MW power plant. Clearly, this represents a significant challenge for large-scale applications in areas that receive good sunlight but without very significant cooling water resources. The cost of countering these heat flows using heat exchange fluids with associated storage, pumps, cooling towers, heat exchange surfaces and supplemental heat energy is a significant impediment to the adoption of enclosed photobioreactor technology for production of large volume fuel and chemical products.

Photobioreactor Passive Thermal Management

The passive thermal regulation system can be implemented in various photobioreactors including flat panels, bubble columns, tubular reactors and a variety of annular designs aimed at managing cooling and heating. Many design variations of the photobioreactor are contemplated within the scope of the invention. Preferably, by maximizing the surface area of the photobioreactor to capture light, maximum amount of light is exposed and captured by the microorganisms to produce products of interest. Provided below is one such photobioreactor design.

In various embodiments, the photobioreactor may be fabricated with inexpensive materials such as acrylic or polycarbonate. For instance, such materials may be extruded into multiple parallel channels and welded to a header assembly to form a single panel. Alternatively, the series of channels and the header assembly may be co-extruded to form a panel. The walls that form the channels within the panel provide structural integrity and support capable of being impact resistant and weather resistant. In an embodiment, the reactor volume may be about 5 liters. In other embodiments, the volume of the reactor may be about 15 to about 25 liters or greater.

In various embodiments, many photobioreactors can be aligned in fluid communication to make up a solar biofactory. The photobioreactors may be set at an angle, anywhere from 0 to 90° depending on various conditions. For example during daytime operations, the photobioreactors are at a 90° angle primarily for diffuse light capture to reduce excess light and photoinhibition while reducing the likelihood of subsequent increase in temperature. For nighttime operations, the photobioreactors are at a 0° angle to maintain temperature in the absence of light.

In certain embodiments, the inclination of the photobioreactors is adjusted quickly in anticipation of advancing weather patterns using a real-time local weather tracking control system. The system can utilize National Weather Service local forecasts and recent local weather patterns to manage the thermal loads and photosynthetic requirements of the photobioreactor field, such as solar irradiation exposure, shading, radiative and convective losses, and ground reflection. The software control system responds to local weather changes, for example cloud cover and rainfall, wind speeds and solar intensity, controlling photobioreactor inclination accordingly. The Passive Thermal Management System can shift a solar biofactory plant into preservation mode when undesirable weather conditions approach, thereby protecting the culture and reducing internal energy losses. In preferred embodiments the photobioreactor inclination can have the ability to move into a horizontal, or close-to-horizontal position, thus reducing radiative losses and maintaining heat of the internal thermal mass during cold weather and especially at night. Heat absorbed and stored in the ground will be contained in the horizontal, or close-to-horizontal position, and will provide additional passive energy.

The controller communicates with a centralized data center to exchange weather observations and to receive thermal management instructions. Controller instructions are driven by real-time local weather. Historic thermal management records will be used to optimize future calculations.

Importantly, the intelligent, centralized thermal management system can reduce or more preferably, eliminate the need for supplemental heating and/or cooling, thereby significantly reducing energy consumption. The system combines weather stations and advanced stepper motor and controls technology in a network-centric design. It can also communicate with the thermal management data center where a sophisticated inclination scheme is applied to tailor heat load and optimize photosynthetic efficiency to the local weather.

Additionally, flue gas injection can provide adequate freeze protection, as well as supplemental heating if required. It is anticipated that additional supplemental heating provided by the flue gas will be greater than about 1 W $m^{-2}$ but less than about 10 W $m^{-2}$. In any event to maximize the efficiency of the system and make maximum use of passive thermal management it is desirable to limit any supplemental heating and cooling to less than about 10 W $m^{-2}$ more preferably less than about 5 W $M^{-2}$ and most preferably less than about 3 W $m^{-2}$.

Figure 14:
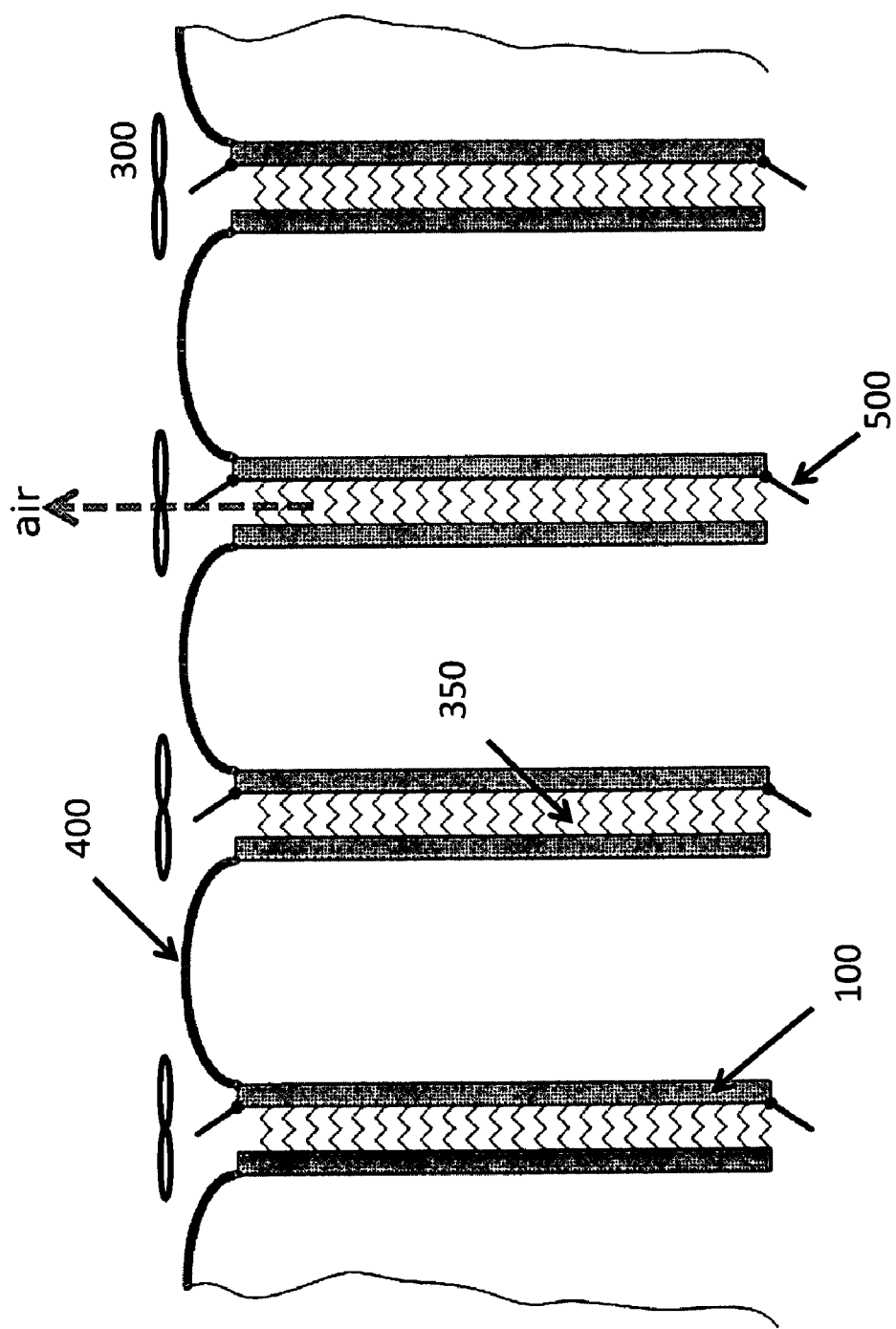
FIG. 14 is a diagram illustrating an arrangement of photobioreactors with a diffuser roof.

FIG. 14 is a side view of multiple photobioreactors oriented North-South. In various embodiments, the photobioreactor comprises a roof 400 connected to at least a second photobioreactor. In certain embodiments, the roof diffuses light, illuminating east and west-facing photobioreactor throughout the day. Additionally, the roof also creates a greenhouse environment around the reactors to achieve desired temperatures. In preferred embodiments, a desired distance between two photobioreactors provides a space or chimneys 350 between photobioreactor with adjustable closures on top and bottom 500 for passive temperature control. There is an optional fan 300 configuration to draw air through the chimney for additional temperature control.

Figure 15:
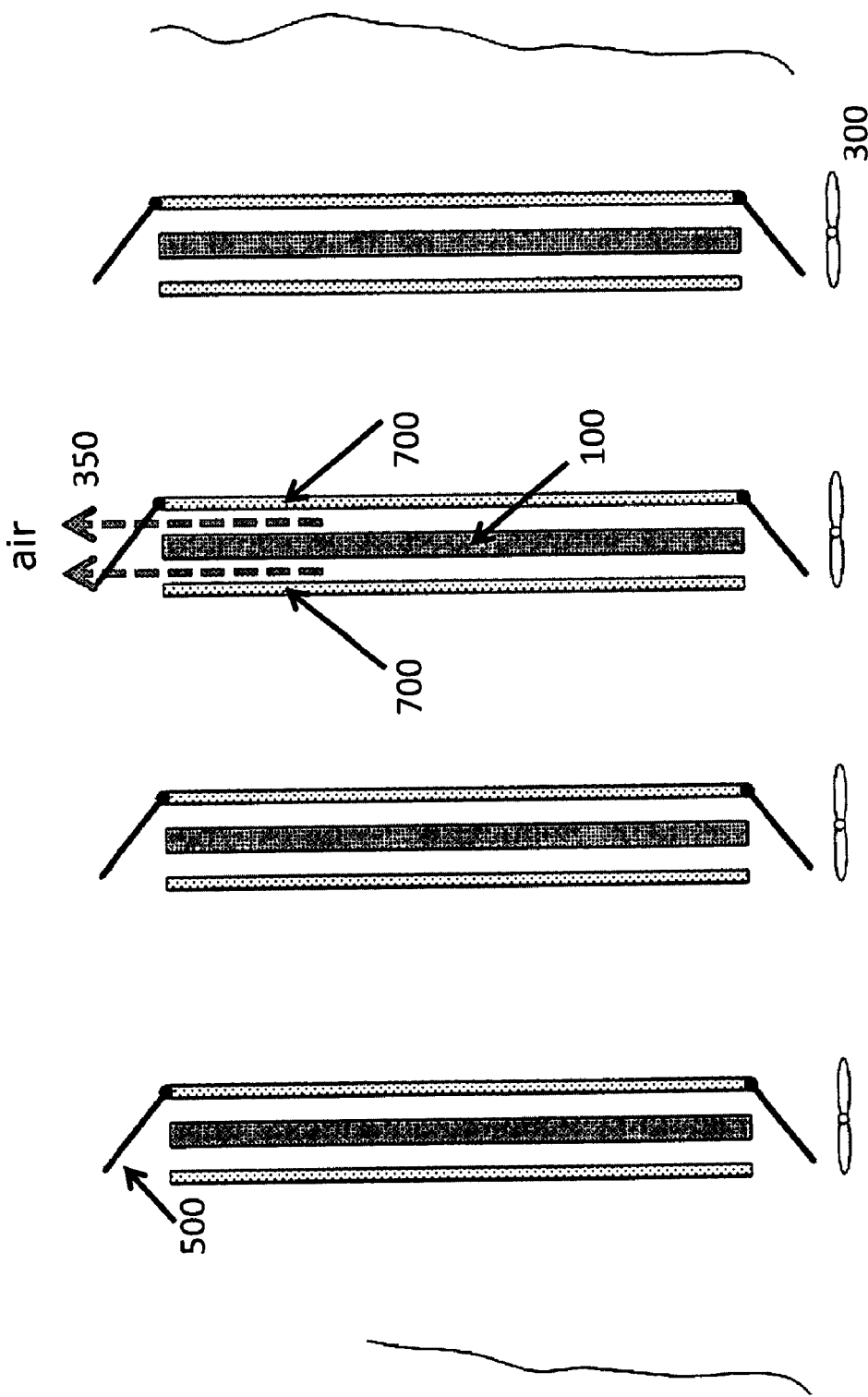
FIG. 15 is an illustration of photobioreactor greenhouses.

FIG. 15 is a side view of another embodiment of a photobioreactor assembly. In this embodiment, at least two side sheets 700 enclose each photobioreactor in a greenhouse environment. A gap between each photobioreactor and the side sheets 700 creates a chimney 350 that cools the photobioreactor when the top/bottom closures are open. Cooling through the chimney can be passive or driven by fans 300. The photobioreactor sidewalls may be shaped to increase area to reduce light intensity and increase heat transfer area. The side sheets can be diffusing to spread light.

Figure 16:
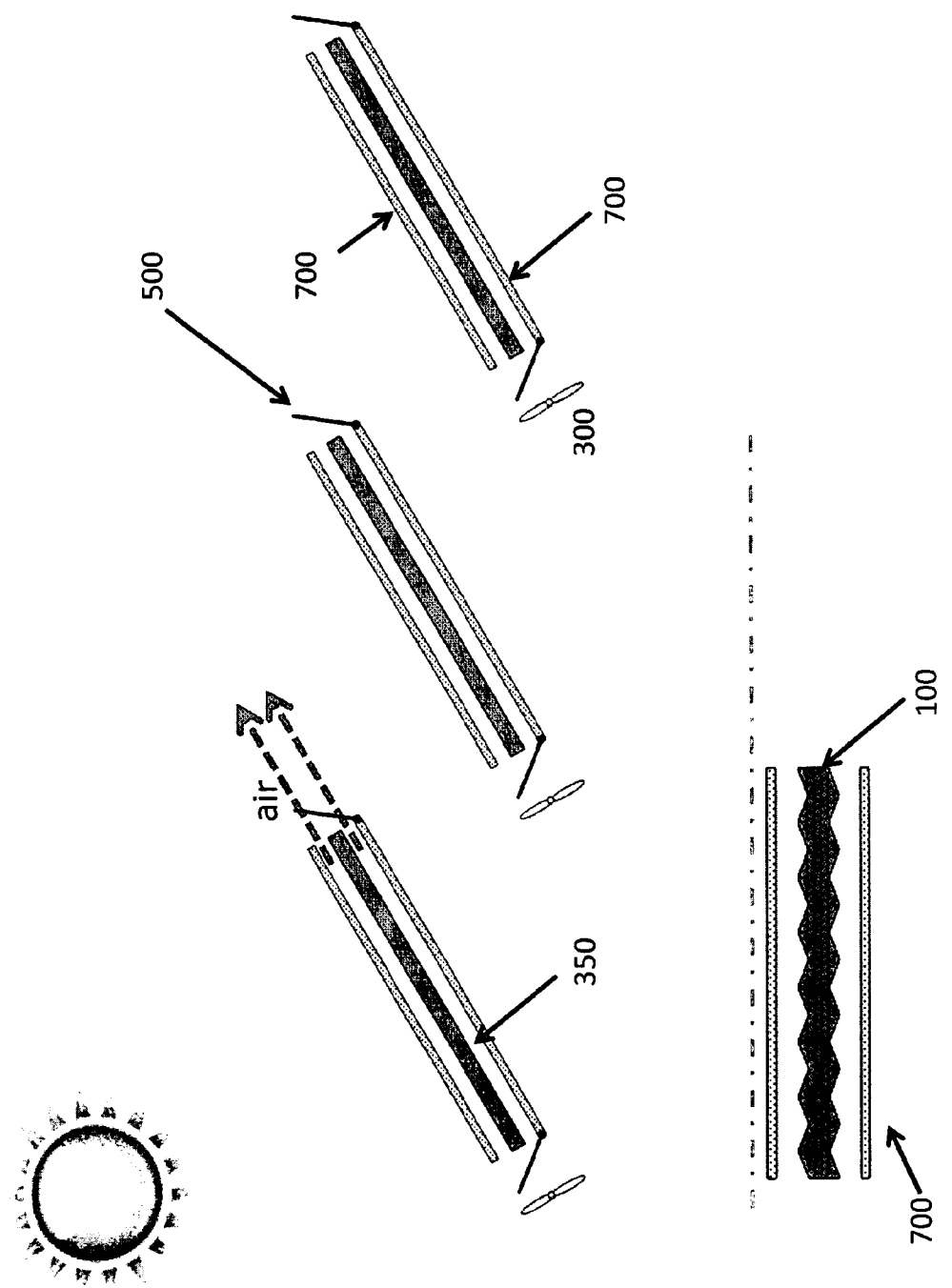
FIG. 16 is an illustration of a tilted photobioreactor arrangement. In the bottom part, an aerial view of a photobioreactor with increased surface area covered by side sheets is shown.

FIG. 16 (upper part) is a side view of another embodiment of a photobioreactor assembly. In this embodiment, at least two side sheets 700 enclose each photobioreactor in a greenhouse environment. A gap between each photobioreactor and the side sheets 700 creates a chimney 350 that cools the photobioreactor when the top/bottom closures 500 are open. Cooling through the chimney 350 can be passive or driven by fans 300. The photobioreactor sidewalls 100 can be shaped to increase area to reduce light intensity and increase heat transfer area FIG. 16 (bottom part). The side sheets 700 can be diffusing to spread light for intensity control. The side sheets 700 and reactor walls 100 may have surface treatment to preferably pass/reflect specific wavelengths for intensity and thermal control. The side sheets 700 and reactor walls 100 can be manufactured with wavelength specific absorbing dyes. The side sheets and reactor walls can be shaped to modify surface area to enhance heat transfer and modify light intensity to the media.

In the embodiment of FIG. 16, the reactor tilt angle can be changed for specific seasons, or throughout the day, to improve control of passive thermal management. A radiation shield can be applied to the back of the reactor (side sheet or reactor walls) for thermal management control. Thermal insulation can be applied to the back of the reactor (side sheet or reactor walls) for thermal management control. The panel can be rotated to face the ground at night to minimize radiation losses to the sky. Individual rows can be rotated to different angles to optimize light intensity and thermal control. Depending on the season, not all rows need to be used.

In certain embodiments, the side sheets and reactor walls may be made from materials such as acrylic or polycarbonate, with high optical clarity. In one embodiment, an anti-reflective coating may be applied to the side sheets and/or reactor walls. Dyes that are absorptive in IR may also be included in the materials. In other embodiments, thermochromic dyes may be added that are tuned to darken once the sheet reaches a certain temperature.

The diffuser roof may be constructed of acrylic or polycarbonate with surface treatment or a thin film added to make it diffusive. In some embodiments, dyes that are absorptive in IR may be used in constructing the diffuser roof. Some embodiments may include thermochromic dyes that are tuned to darken once the diffuser roof element reaches a certain temperature.

Chimney and Spacing: In some embodiments, the side sheets are spaced about 1 inch from the reactor walls, but the spacing may range from about 0.5 to about 2 inches.

Regarding the adjustable closures (top and bottom), in some embodiments these may be electrically driven. In other embodiments these can be driven hydraulically by thermal actuators, and thus be fully passive.

Regarding fans, in some embodiments they can be individual small fans at each reactor, or a larger fan supplying a small group of reactors. In some embodiments the fans can be powered by photovoltaic panels.

Several advantages of the passive thermal regulation include illumination of the photobioreactor under a novel passive cooling regime with low capital costs allowing organisms to maintain maximum productivity in a wide range of environments; use of multiple photobioreactors in a modular array that can be expanded without significant modification over land areas from about 100-about 10,000 acres; use of key inputs such as concentrated $CO_2$ emanating from critical sectors, e.g., fossil fuel energy production and cement manufacturing, to directly convert $CO_2$ emissions to desired output products; ability to located solar biofactories, e.g., near $CO_2$ sources or pipelines so that $CO_2$ distribution is minimized within the facility with minimal parasitic loads. Preferred photobioreactor designs will be optimized to ensure optimum or maximum light capture, mixing, $CO_2$ injection and fuel separation while minimizing energy needs.

In some embodiments, the photobioreactors are able to achieve passive thermal control within about 5° C. to about 10° C. of ambient.

In some embodiments, the photobioreactor comprises at least two different organisms. A thermotolerant cyanobacteria, plant or algae or another thermophilic strain can accommodate the temperature spectrum envisioned for year-round heat integration in the solar conversion process. Alternatively, a mix of thermophilic strains and mesophilic strains may also be used.

In other embodiments, the methods are disclosed to use of photobioreactors to enable the production of carbon-based products on non-arable land. The photobioreactor and process design are optimized to ensure efficient conversion of sunlight to fuel. Advanced bioprocessing and optics design principles are deployed to optimize light distribution, mass and heat transfer and mixing to maximize productivity.

Preferably, photobioreactor design, prototyping and manufacturing design meet process requirements with a cost target of less than about $20/m$^2$ of land area to allow for a scalable solution that can be deployed over a large area. Design for Manufacturability (DFM) concepts are a particular focus to enable low cost, reliable mass production. Fermentation nutrient control strategies are developed that are tightly integrated with organism engineering to ensure maximum yield of end-product on fixed carbon.

In various embodiments, the combination of strain optimization via carbon flux control and the photobioreactor of the invention has increased ethanol output to daily areal productivity levels surpassing those projected for mature cellulosic-based processes (>3.5 g/m$^2$/day).

An example pilot plant for the production of diesel fuel may occupy approximately 1 acre of non-arable land and may produce about 25 gallons of diesel per day. A diesel process prototype pilot plant may function in an operational environment as follows:

Continuous, controlled chain-length diesel production at an areal productivity of ~20 g/m$^2$/day from a concentrated industrial $CO_2$ source with net water use less than about 5 gal/gal fuel;

>30 days continuous production at >5% photon energy capture efficiency;

An integrated production platform that can scale to energy independence at a cost that is competitive with current fossil resources without subsidies; and Such process offsets the impacts of conventional power generation by converting waste $CO_2$ to valuable liquid fuels through use of flue gas or other concentrated $CO_2$ sources.

The highly efficient, integrated process reduces or eliminates costly and wasteful intermediates and processes resulting in a very high net positive energy ratio. The passive thermal management reduces or eliminates the need for external cooling sources, resulting in little, if any, evaporative water loss.

In certain aspects, contamination by competing organisms is problematic for efficient carbon conversion. At laboratory scale, the photobioreactor can be sterilized and run in monoculture mode. Organism engineering strategies or scaled process methods developed would help to minimize contamination issues at full-scale. Accordingly, the photobioreactors are sterilizable individually or in multiple arrays.

Passive thermal designs that allow tight temperature control in the largest range of locations, and minimize water and parasitic power consumption, are important to the success of the technology. Further refinement of the current passive thermal design concepts are contemplated by performing stress and life cycle tests under simulated and real outdoors conditions.

Preferably, photobioreactors may be located in environments that experience significant solar radiation and large temperature transitions.

Nighttime Operations

Operating at night can significantly increase to potentially double total productivity. Accordingly, operating a solar biofactory with artificial light is also contemplated. It is contemplated that various artificial lighting sources adapted to the solar biofactory, e.g., fluorescent lamps can be used. Such solar biofactory can harness power from the grid to drive biological processes at night.

In another embodiment, inputs that would not otherwise be used at night in the absence of artificial light can be used. Carbon dioxide from a concentrated source can be concentrated and stored, preferentially as dry ice to allow for cooling as well as condensation free gas distribution. Power for this can be preferentially used from the same concentrated source (e.g., a coal plant) but at non-peak times of night (e.g., 12-4 AM).

In another embodiment, the cell system can have two biological elements to it (either in the same cell or in multiple cells) wherein it is light driven during the day and driven by stored or otherwise derived inputs at night. For example a cell can harvest light and covert to an intermediate during the day and the same or different cell can convert that intermediate to a desirable end product at night.

Operations During Different Seasons

FIG. 13 indicates the net heat load of the photobioreactor as a function of different seasons for both a thermophile operating at 65° C. and a mesophile operating at 37° C. In the event of a net negative load supplemental heating must be supplied. Approximately 10-20 W $m^{-2}$ of solar energy can be captured as chemical energy (fuel) and therefore waste heat at essentially zero cost would be required to ensure a positive overall energy balance. Given the amount of waste heat available at a power plant this would limit the potential size of a facility to less than 1 acre per MW of operating capacity. In the event that cooling is required (positive net heat absorbed) this would require significant cooling water. A 1000 acre facility with a cooling requirement of 100 W $m^{-2}$ requires 400 MW of cooling (similar order as a 600 MW power plant unit). Such a significant cooling water requirement would limit the potential application of the photobioreactor technology at large scale.

Accordingly, the passive thermal regulation would obviate the need or at least reduce the dependency on water and minimize energy input required to circulate or pump water.

Figure 12:
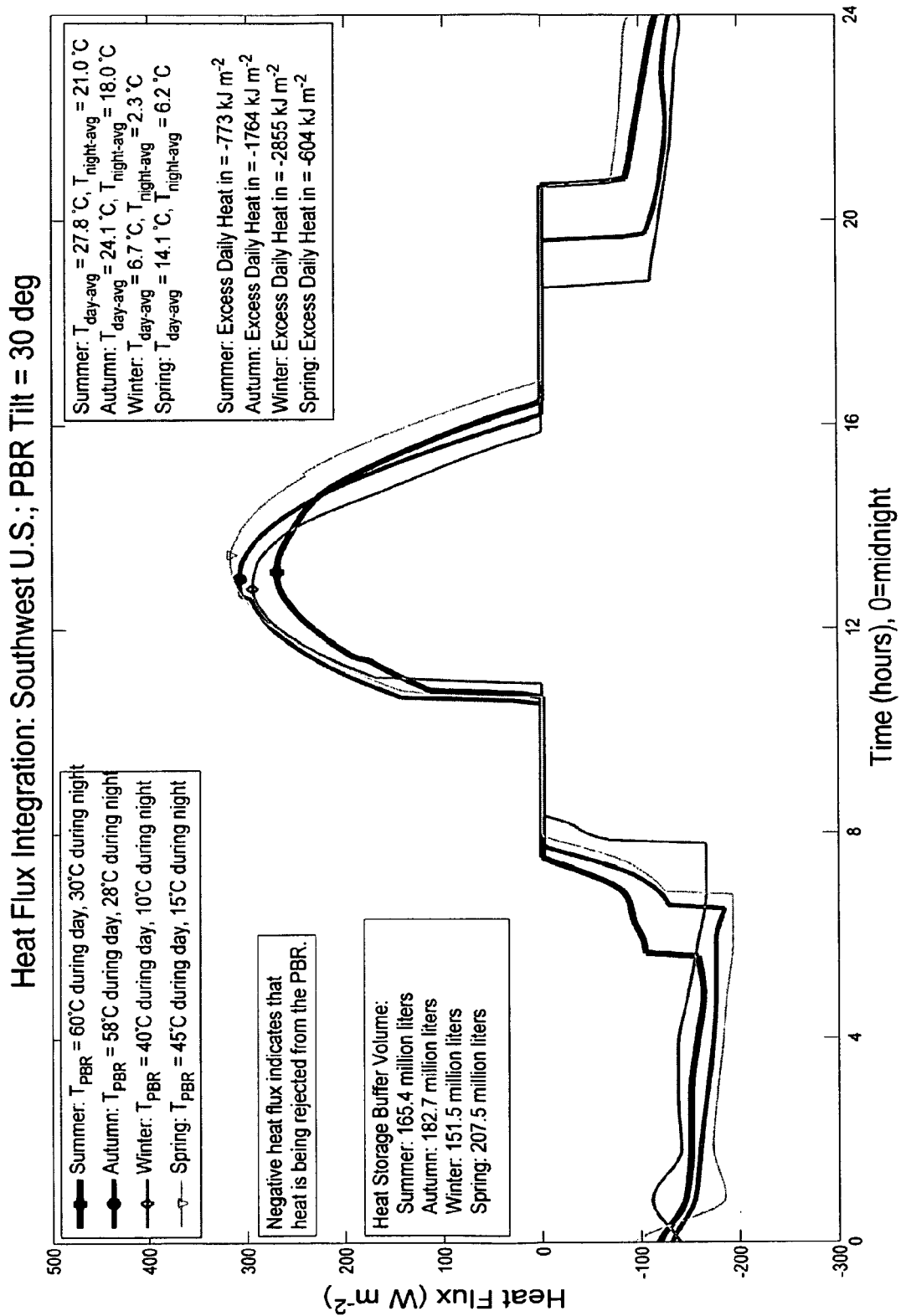
FIG. 12 is a graphical representation of optimized heat integration with variable temperature operation and external heating/cooling reservoir.

FIG. 12 shows the net heat absorbed into a photobioreactor over the course of a day. Data is shown for operation during different times of the year. Average local temperatures for day and night are shown, indicating the large variation in ambient conditions in which the reactor is operating. Integrated heat fluxes are indicated. The size of buffer storage required to absorb heat during the day that is then used to heat the reactor during the night is shown for a 1000 acre plant. The excess daily heat values are negative indicating that even after using the buffer storage, external heating of about 5 to about 35 W $M^{-2}$ is required depending on the time of year and the operating temperature. Given typical waste heat available form a power plant this would limit the size of a facility to approximately 1 acre per MW power plant capacity, whereas at least 10 acres can be supported by the typical $CO_2$ emission the same power plant rating of 1 MW. Optimization of the heat integration significantly minimize external heating and cooling but requires production strains that can operate over a wide range of temperatures and a large buffer storage.

A modular and mass-manufactured photobioreactor is the building block of this invention. Preferably, the photobioreactor is designed for deployment in pre-fabricated assemblies that can be installed easily with minimal skilled labor. Muliwall (multi-skinned) extruded Polycarbonate or Acrylic (PMMA) sheet provides the substrate for the radiant and insulative barrier or shield, and reflective thin film technology, as well as the conduit for the growth of the photosynthetic organisms. More preferably, the photobioreactor is bonded (multi-stage molding, vibration or laser welding) to a proprietary header and sparger mechanism. The entire assembly snaps into a light weight, structural substrate (e.g. carbon fiber-reinforced or aluminum) and mounts to a single-axis incliner that houses the stepper motor and controls mechanism. The single-axis incliner serves as a mechanical underpinning for multiple photobioreactor assemblies and is adapted to adjust in real-time to optimize photosynthetic efficiency and regulate shading to manage heat loads.

Systematically spaced photobioreactor assemblies combine to form a geometrically optimized modular field. The sub-field design geometrically optimizes the layout to maximize the harvested solar energy and to minimize undesired thermal effects.

Photobioreactor Passive Thermal Management & Weather Tracking Technology

The inclination of the photobioreactors is adjusted quickly in anticipation of advancing weather patterns using a real-time local weather tracking control system. The system will utilize National Weather Service local forecasts and recent local weather patterns to manage the thermal loads and photosynthetic requirements of the photobioreactor field, such as solar irradiation exposure, shading, radiative and convective losses, and ground reflection. The software control system responds to local weather changes, for example cloud cover and rainfall, wind speeds and solar intensity, controlling photobioreactor inclination accordingly. The Passive Thermal Management System can shift the plant into preservation mode when undesirable weather conditions approach, thereby protecting the culture and reducing internal energy losses. Photobioreactor inclination can have the ability to move into a horizontal, or close-to-horizontal position, thus reducing radiative losses and maintaining heat of the internal thermal mass during cold weather and especially at night. Heat absorbed and stored in the ground can be contained in the horizontal, or close-to-horizontal position, and can provide additional passive energy.

The controller communicates with a centralized data center to exchange weather observations and to receive thermal management instructions. Controller instructions are driven by real-time local weather. Historic thermal management records will be used to optimize future calculations.

The intelligent, centralized thermal management system will reduce or eliminate the need for supplemental heating and/or cooling, thereby reducing energy consumption. The system combines weather stations and advanced stepper motor and controls technology in a network-centric design. It communicates with a thermal management data center where an inclination scheme is applied to tailor heat load and optimize photosynthetic efficiency to the local weather.

Flue gas injection can provide adequate freeze protection, as well as supplemental heating if required. It is anticipated that additional supplemental heating provided by the flue gas will be greater than about 1 W m$^{-2}$ but less than about 10 W m$^{-2}$. In any event to maximize the efficiency of the system and make maximum use of passive thermal management it is desirable to limit any supplemental heating and cooling to less than about 10 W m$^{-2}$ more preferably less than about 5 W m$^{-2}$ and most preferably less than about 3 W m$^{-2}$.

Figure 17:
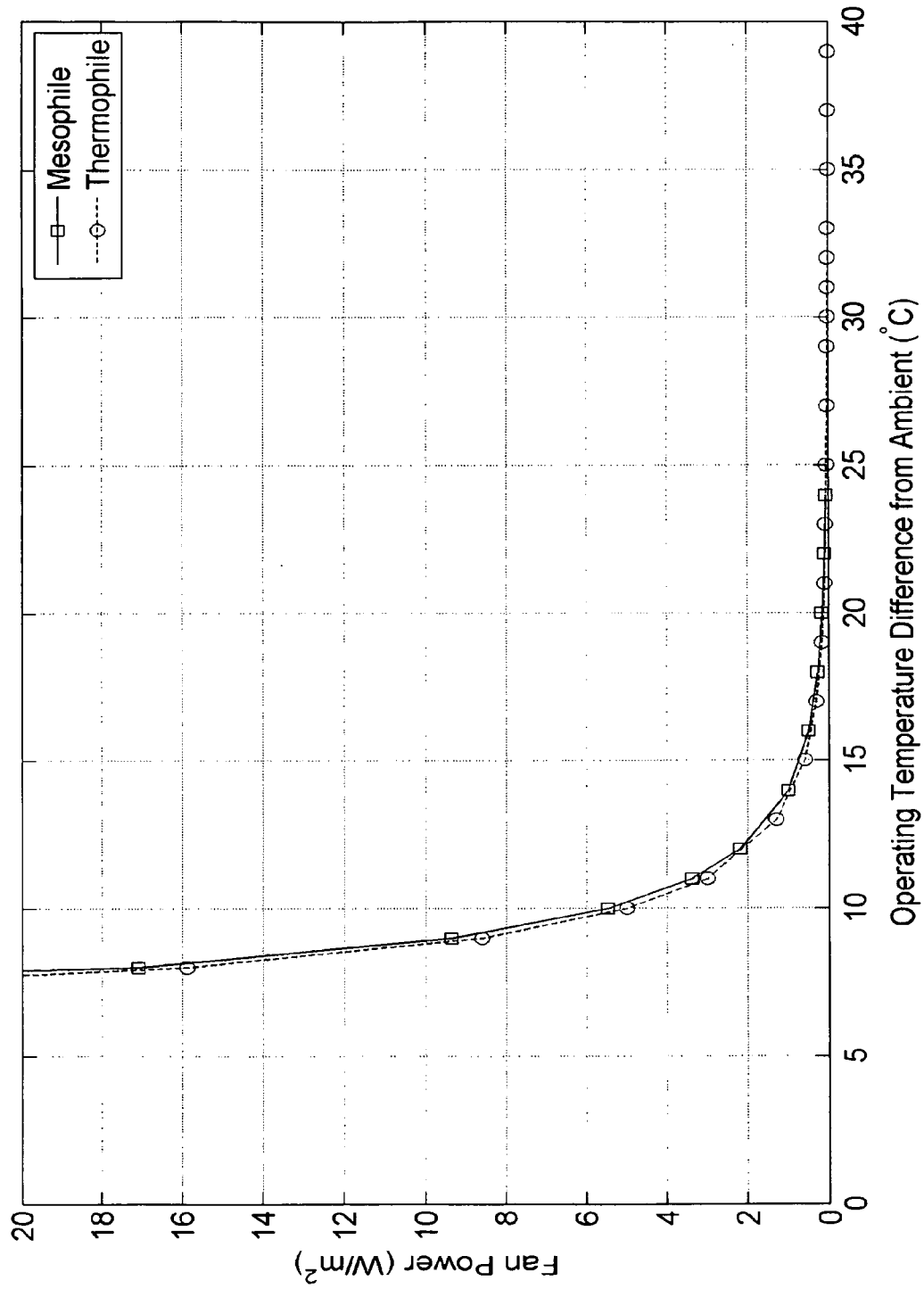
FIG. 17 is a graphical representation showing fan power used to cool an example reactor to a desired operating temperature for two cases: mesophile (desired T-37° C.) and thermophile (desired T-58° C.).

FIG. 17 is a graphical representation showing fan power used to cool an example reactor to a desired operating temperature for two cases: mesophile (desired T~37° C.) and thermophile (desired T~58° C.). The graph shows a solution for an example tilted greenhouse, tilted at 30 degrees, south-facing. The computation is for a summer day (~mid-July) at solar noon, assuming average solar insolation. In particular, the graph shows how much fan power is used in the example configuration to cool the reactor to a desired operating temperature for two cases: mesophile (desired T ~37° C.) and thermophile (desired T ~58° C.). The x-axis shows the difference between desired operating temperature and the ambient temperature. Note that the mesophile and thermophile cases essentially collapse in this way of displaying the results. As the ambient gets cooler, the "difference" gets larger and the amount of fan power decreases. In this example, the plot indicates that so long as the ambient temperature is more than 10 degrees C. less than operating temperature, the system can be run passively.

Temperature control of the photobioreactors may be obtained using air, preferably ambient air. In example systems, less than about 10 W/m2 of power input is used to obtain the cooling (e.g., for blowing the air and operating the temperature control system), and preferably less than about 5 W/m$^2$. For example, in a system for which one may need to reject on the order of about 500 W/m$^2$ of heat at mid-day, the input power is about 1% of the heat load to be rejected. In one implementation, the power may be obtained from a pV solar panel located near the reactor. pV panels typically produce about 130 W/m$^2$. For instance, if 5 W/m$^2$ power is provided by the pV panel, the area of the PV panel can be less than 4% of the ground area. In this implementation, cooling may be obtained from sources local to the reactor, minimizing infrastructure. An air-based cooling system provides the advantage of being more location independent.

Culture Media

The liquid medium contained within the chamber of the photobioreactor apparatus during operation may comprise water or a saline solution (e.g. sea water or brackish water) mixed with sufficient nutrients to facilitate viability and growth of light capturing organisms contained therein. Depending on the organism, it may be advantageous to use liquid medium comprising brackish water, sea water, or other non-potable water obtained from a locality in which the photobioreactor apparatus will be operated and from which the organism contained therein was derived from or is adapted to.

Organisms are, in particular, supplemented with one or nitrogen sources. In one embodiment, the nitrogen source is one or more of urea, uric acid, ammonia, ammonium salts, nitrate, or one or more amino acids. In certain embodiments, the nitrogen source is ammonia. In an alternative embodiment, the nitrogen source is provided through the gas inlet, which can take the form of one or more of N$_2$, NO, NO$_x$, among others.

Particular liquid medium compositions, nutrients, etc. required or suitable for use in maintaining a growing algae or other light capturing organism culture (e.g., liquid BG-11 medium, A+) are generally well known in the art. Potentially, a wide variety of liquid media can be utilized in various forms for various embodiments of the solar biofactory, as would be understood by those of ordinary skill in the art. Appropriate liquid medium components and nutrients are, for example, discussed in detail in: Rogers, L J. and Gallon J. R. "Biochemistry of the Algae and Cyanobacteria," Clarendon Press Oxford, 1988; Burlew, John S. "Algal Culture: From Laboratory to Pilot Plant." Carnegie Institution of Washington Publication 600. Washington, D.C., 1961 (hereinafter "Burlew 1961"); and Round, F. E. The Biology of the Algae. St Martin's Press, New York, 1965; Golden S S et al. (1987) "Genetic engineering of the Cyanobacteria chromosome" Methods Enzymol 153:215-231 and in S. S. Golden and L. A. Sherman, J. Bacteriology 158:36 (1984), incorporated herein by reference).

Enhanced media composition is described in Examples 3, 4 and 5. In various embodiments, the invention provides a media composition as set forth in Example 4. Additional embodiments include increased amount N, P and/or Fe in the media for enhanced growth of light capturing organisms.

During operation of the photobioreactor apparatus, the panel 100 is filled with enough liquid medium so as to permit circulation of the liquid medium (e.g., in one direction) during operation. In some embodiments, at least some portion of the volume of the panel is left unfilled with liquid medium.

It is contemplated that certain conditions, such as low pH, high EtOH or organic acids in medium, are likely to render the photobioreactor environment harsh for culturing organisms pH of Media The pH of the liquid medium can be monitored with a pH probe. pH of the medium can be controlled at desirable levels for a particular organism by adjusting CO$_2$ or chemicals, such as, ammonia, tris, urea, HEPES, hydrochloric acid and sodium hydroxide. Preferably, the addition of acidic CO$_2$ to the photobioreactor is controlled to match the production of products to maintain a stable pH under balanced growth or production conditions. The choice of nitrogen source in the media is important as a means to provide for pH control. Additionally, the amount of evaporation and appropriate new fluid addition provides for another means to provide pH control.

In general, chemicals for nutrient level maintenance and pH control and other factors may be added automatically directly into the liquid phase within the photobioreactor apparatus, if desired. The computer control system can also be configured to control the liquid phase temperature in the photobioreactor apparatus by either or both of controlling a heat exchange system or other temperature control system within or connected with the photobioreactor apparatus, or, in alternative embodiments removing liquid medium from the photobioreactor apparatus and passing through a heat exchanger in, for example, a temperature controlled water bath or a water basin.

Optical Density

The optical density of the liquid medium can be measured at certain wavelengths appropriate for the given organism. These wavelengths, which are assumed to be linearly related to biomass concentration, are generally well known in the art. Cell density can be calculated using spectrophotometer measurements (see, Hiroyasu et al., 1998). Such readings can be used to monitor organism concentration to ensure proper cell activity as well as potential signs of challenges to the desired cell population, such as non-optimal media conditions, altered pH, high concentrations of toxic substances, as well as the presence of exogenous organisms.

Operating Conditions and Cell Population Control

In various embodiments, engineered organisms are cultured in the solar biofactory, systems and methods. In such embodiments, in order to keep the concentration of organisms within the photobioreactor apparatus within a range suitable for long term operation and productivity, a portion of the organism may be harvested and the photobioreactor apparatus may be supplemented with fresh, organism-free medium (or previously harvested medium having a low concentration) to adjust concentration of organism within the photobioreactor apparatus. Concentration can increase exponentially with time (the log growth phase) up to a certain point, after which the concentration will tend to level off and proliferation and growth will decrease. In certain embodiments, the concentration within the photobioreactor apparatus is maintained within an operating range that is near the upper end of the concentration in which the organism is still in the log growth regime. As would be understood by those by those skilled in the art, the particular growth curve characterizing a given species of organism will be different from species to species and, even within a given species of organism, may be different depending on differences in operating and environmental factors, as well as with any genetic modifications that may have been made through the insertion of exogenous nucleic acids or through an evolutionary process (e.g., liquid medium composition, growth temperature, gas feed composition, etc.).

Harvesting the organism, adjusting concentration, and introducing additional liquid medium can be facilitated via inlet means and outlet means as described earlier. Control of the concentration of organism is important both from the standpoint of maintaining a desirable level of growth and proliferation as well as providing desirable levels of photomodulation within the conduits. The organism can be harvested periodically or continuously to maintain the desired concentration range during operation.

According to one method, harvesting takes place in a semi-continuous fashion, meaning that only a portion of the organism is removed from the photobioreactor apparatus at a given time. To harvest the organism, media containing the organism is removed from the photobioreactor and allowed to settle such that the density of the organism will allow it to settle at the bottom of the chamber, wherein the organism can be readily removed. Additionally, flocculants, chemicals that cause the organism to clump and settle, may be used, in certain embodiments, to assist in the harvest. Some useful flocculants include clay (e.g. with particle size<2 µm), aluminum sulfate or polyacrylamide. After settling, organism may be withdrawn through the bottom of the channels or through various outlets. The water and nutrients contained in the harvested cells can be extracted and recycled to the liquid medium supply of the photobioreactor apparatus. This step may reduce waste and water use of the photobioreactor apparatus and the overall system, thereby lowering environmental impact and operational cost. In certain cases cells can be separated from the medium using filtration (e.g. micro- or ultrafiltration using polymeric, ceramic or metal membranes), centrifugation (e.g. decanter or high speed disc centrifuge) or flotation before harvesting. Removed cells may then be processed by any means known in the art, such as extraction of the cell membrane for the production of biodiesel, saccharification of polymeric moieties for the production of ethanol, and burning of the biomass for the generation of energy, among others.

In some embodiments, cell concentration is kept constant by maintaining the photobioreactor apparatus as a chemostat wherein the fluid is constantly flowed and retaining within a closed loop. Through this method, which is well known to those skilled in the art, dead or dying cells can be readily removed as processed by any means known in the art.

In certain embodiments, a solar biofactory is adapted to be used with sensors, controllers, programmable logic controllers and a control system, networked together for the photobioreactor apparatus. Such control systems are well-known in the art and can be modified or adapted to accordingly by a skilled artisan.

The solar biofactory systems and methods can be configured with various probes and monitors for measuring the pressure of the feed gas fed into the spargers (e.g., one or more pressure monitors), as well as one or more flow meters for measuring gas flow rates, and one or more flow meters for measuring bulk liquid flow rate within the photobioreactor apparatus. Gas and liquid flow rates can be controlled, at least in part, to facilitate desired or optimal levels of photomodulation by inducing desirable liquid flow patterns within the photobioreactor apparatus. Another control factor dictating the overall flow of gas fed to photobioreactor apparatus can be the desired level of removal of pollutants such as $CO_2$ and/or $NO_x$ by the photobioreactor apparatus. For example, the system includes appropriate gas composition monitoring devices for monitoring the concentration of various gases, such as $CO_2$, $NO_x$, $O_2$, etc. in the feed gas and treated gas. Gas inlet flow rate and/or distribution to the spargers can be adjusted and controlled to yield a desirable level of pollutant removal by the solar biofactory system.

Organisms

Various embodiments of solar biofactory systems and methods described herein enable conversion of light, water and carbon dioxide into biomass, biofuels, chemical intermediates, chemicals, pharmaceutical agents and biologically produced chemicals in any light capturing organisms. Light capturing organisms include autotrophs, phototrophs, heterotrophs, and organisms engineered to downregulate or knock out expression of an endogenous gene, express one or more heterologous genes, overexpress one or more endogenous genes related to photosynthesis or its central metabolism.

Plants include but are not limited to the following genera: *Arabidopsis, Beta, Glycine, Jatropha, Miscanthus, Panicum, Phalaris, Populus, Saccharum, Salix Simmondsia*, and *Zea*. Algae and cyanobacteria include but are not limited to the following genera: *Acanthoceras, Acanthococcus, Achnanthes, Achnanthidium, Actinastrum, Actinochloris, Actinocyclus, Actinotaenium, Amphichrysis, Amphidinium, Amphikrikos, Amphipleura, Amphiprora, Amphithrix, Amphora, Anabaena, Anabaenopsis, Aneumastus, Ankistrodesmus, Ankyra, Anomoeoneis, Apatococcus, Aphanizomenon, Aphanocapsa, Aphanochaete, Aphanothece, Apiocystis, Apistonema, Arthrodesmus, Artherospira, Ascochloris, Asterionella, Asterococcus, Audouinella, Aulacoseira, Bacillaria, Balbiania, Bambusina, Bangia, Basichlamys, Batrachospermum, Binuclearia, Bitrichia, Blidingia, Botrdiopsis, Botrydium, Botryococcus, Botryosphaerella, Brachiomonas, Brachysira, Brachytrichia, Brebissonia, Bulbochaete, Bumilleria, Bumilleriopsis, Caloneis, Calothrix, Campylodiscus, Capsosiphon, Carteria, Catena, Cavinula, Centritractus, Centronella, Ceratium, Chaetoceros, Chaetochloris, Chaetomorpha, Chaetonella, Chaetonema, Chaetopeltis, Chaetophora, Chaetosphaeridium, Chamaesiphon, Chara, Characiochloris, Characiopsis, Characium, Charales, Chilomonas, Chlainomonas, Chlamydoblepharis, Chlamydocapsa, Chlamydomonas, Chlamydomonopsis, Chlamydomyxa, Chlamydonephris, Chlorangiella, Chlorangiopsis, Chlorella, Chlorobotrys, Chlorobrachis, Chlorochytrium, Chlorococcum, Chlorogloea, Chlorogonium, Chlorolobion, Chloromonas, Chlorophysema, Chlorophyta, Chlorosaccus, Chlorosarcina, Choricystis, Chromophyton, Chromulina,*

*Chroococcidiopsis, Chroococcus, Chroodactylon, Chroomonas, Chroothece, Chrysamoeba, Chrysapsis, Chrysidiastrum, Chrysocapsa, Chrysocapsella, Chrysochaete, Chrysochromulina, Chrysococcus, Chrysocrinus, Chrysolepidomonas, Chrysolykos, Chrysonebula, Chrysophyta, Chrysopyxis, Chrysosaccus, Chrysophaerella, Chrysostephanosphaera, Clodophora, Clastidium, Closteriopsis, Closterium, Coccomyxa, Cocconeis, Coelastrella, Coelastrum, Coelosphaerium, Coenochloris, Coenococcus, Coenocystis, Colacium, Coleochaete, Collodictyon, Compsogonopsis, Compsopogon, Conjugatophyta, Conochaete, Coronastrum, Cosmarium, Cosmioneis, Cosmocladium, Crateriportula, Craticula, Crinalium, Crucigenia, Crucigeniella, Cryptoaulax, Cryptomonas, Cryptophyta, Ctenophora, Cyanodictyon, Cyanonephron, Cyanophora, Cyanophyta, Cyanothece, Cyanothomonas, Cyclonexis, Cyclostephanos, Cyclotella, Cylindrocapsa, Cylindrocystis, Cylindrospermum, Cylindrotheca, Cymatopleura, Cymbella, Cymbellonitzschia, Cystodinium Dactylococcopsis, Debarya, Denticula, Dermatochrysis, Dermocarpa, Dermocarpella, Desmatractum, Desmidium, Desmococcus, Desmonema, Desmosiphon, Diacanthos, Diacronema, Diadesmis, Diatoma, Diatomella, Dicellula, Dichothrix, Dichotomococcus, Dicranochaete, Dictyochloris, Dictyococcus, Dictyosphaerium, Didymocystis, Didymogenes, Didymosphenia, Dilabifilum, Dimorphococcus, Dinobryon, Dinococcus, Diplochloris, Diploneis, Diplostauron, Distrionella, Docidium, Draparnaldia, Dunaliella, Dysmorphococcus, Ecballocystis, Elakatothrix, Ellerbeckia, Encyonema, Enteromorpha, Entocladia, Entomoneis, Entophysalis, Epichrysis, Epipyxis, Epithemia, Eremosphaera, Euastropsis, Euastrum, Eucapsis, Eucocconeis, Eudorina, Euglena, Euglenophyta, Eunotia, Eustigmatophyta, Eutreptia, Fallacia, Fischerella, Fragilaria, Fragilariforma, Franceia, Frustulia, Curcilla, Geminella, Genicularia, Glaucocystis, Glaucophyta, Glenodiniopsis, Glenodinium, Gloeocapsa, Gloeochaete, Gloeochrysis, Gloeococcus, Gloeocystis, Gloeodendron, Gloeomonas, Gloeoplax, Gloeothece, Gloeotila, Gloeotrichia, Gloiodictyon, Golenkinia, Golenkiniopsis, Gomontia, Gomphocymbella, Gomphonema, Gomphosphaeria, Gonatozygon, Gongrosia, Gongrosira, Goniochloris, Gonium, Gonyostomum, Granulochloris, Granulocystopsis, Groenbladia, Gymnodinium, Gymnozyga, Gyrosigma, Haematococcus, Hafniomonas, Hallassia, Hammatoidea, Hannaea, Hantzschia, Hapalosiphon, Haplotaenium, Haptophyta, Haslea, Hemidinium, Hemitoma, Heribaudiella, Heteromastix, Heterothrix, Hibberdia, Hildenbrandia, Hillea, Holopedium, Homoeothrix, Hormanthonema, Hormotila, Hyalobrachion, Hyalocardium, Hyalodiscus, Hyalogonium, Hyalotheca, Hydrianum, Hydrococcus, Hydrocoleurn, Hydrocoryne, Hydrodictyon, Hydrosera, Hydrurus, Hyella, Hymenomonas, Isthmochloron, Johannesbaptistia, Juranyiella, Karayevia, Kathablepharis, Katodinium, Kephyrion, Keratococcus, Kirchneriella, Klebsormidium, Kolbesia, Koliella, Komarekia, Korshikoviella, Kraskella, Lagerheimia, Lagynion, Lamprothamnium, Lemanea, Lepocinclis, Leptosira, Lobococcus, Lobocystis, Lobomonas, Luticola, Lyngbya, Malleochloris, Mallomonas, Mantoniella, Marssoniella, Martyana, Mastigocoleus, Gastogloia, Melosira, Merismopedia, Mesostigma, Mesotaenium, Micractinium, Micrasterias, Microchaete, Microcoleus, Microcystis, Microglena, Micromonas, Microspora, Microthamnion, Mischococcus, Monochrysis, Monodus, Monomastix, Monoraphidium, Monostroma, Mougeotia, Mougeotiopsis, Myochloris, Myromecia, Myxosarcina, Naegeliella, Nannochloris, Nautococcus, Navicula, Neglectella, Neidium, Nephroclamys, Nephrocytium, Nephrodiella, Nephroselmis, Netrium, Nitella, Nitellopsis, Nitzschia, Nodularia, Nostoc, Ochromonas, Oedogonium, Oligochaetophora, Onychonema, Oocardium, Oocystis, Opephora, Ophiocytium, Orthoseira, Oscillatoria, Oxyneis, Pachycladella, Palmella, Palmodictyon, Pnadorina, Pannus, Paralia, Pascherina, Paulschulzia, Pediastrum, Pedinella, Pedinomonas, Pedinopera, Pelagodictyon, Penium, Peranema, Peridiniopsis, Peridinium, Peronia, Petroneis, Phacotus, Phacus, Phaeaster, Phaeodermatium, Phaeophyta, Phaeosphaera, Phaeothamnion, Phormidium, Phycopeltis, Phyllariochloris, Phyllocardium, Phyllomitas, Pinnularia, Pitophora, Placoneis, Planctonema, Planktosphaeria, Planothidium, Plectonema, Pleodorina, Pleurastrum, Pleurocapsa, Pleurocladia, Pleurodiscus, Pleurosigma, Pleurosira, Pleurotaenium, Pocillomonas, Podohedra, Polyblepharides, Polychaetophora, Polyedriella, Polyedriopsis, Polygoniochloris, Polyepidomonas, Polytaenia, Polytoma, Polytomella, Porphyridium, Posteriochromonas, Prasinochloris, Prasinocladus, Prasinophyta, Prasiola, Prochlorphyta, Prochlorothrix, Protoderma, Protosiphon, Provasoliella, Prymnesium, Psammodictyon, Psammothidium, Pseudanabaena, Pseudenoclonium, Psuedocarteria, Pseudochate, Pseudocharacium, Pseudococcomyxa, Pseudodictyosphaerium, Pseudokephyrion, Pseudoncobyrsa, Pseudoquadrigula, Pseudosphaerocystis, Pseudostaurastrum, Pseudostaurosira, Pseudotetrastrum, Pteromonas, Punctastruata, Pyramichlamys, Pyramimonas, Pyrrophyta, Quadrichloris, Quadricoccus, Quadrigula, Radiococcus, Radiofilum, Raphidiopsis, Raphidocelis, Raphidonema, Raphidophyta, Peimeria, Rhabdoderma, Rhabdomonas, Rhizoclonium, Rhodomonas, Rhodophyta, Rhoicosphenia, Rhopalodia, Rivularia, Rosenvingiella, Rossithidium, Roya, Scenedesmus, Scherffelia, Schizochlamydella, Schizochlamys, Schizomeris, Schizothrix, Schroederia, Scolioneis, Scotiella, Scotiellopsis, Scourfieldia, Scytonema, Selenastrum, Selenochloris, Sellaphora, Semiorbis, Siderocelis, Diderocystopsis, Dimonsenia, Siphononema, Sirocladium, Sirogonium, Skeletonema, Sorastrum, Spermatozopsis, Sphaerellocystis, Sphaerellopsis, Sphaerodinium, Sphaeroplea, Sphaerozosma, Spiniferomonas, Spirogyra, Spirotaenia, Spirulina, Spondylomorum, Spondylosium, Sporotetras, Spumella, Staurastrum, Stauerodesmus, Stauroneis, Staurosira, Staurosirella, Stenopterobia, Stephanocostis, Stephanodiscus, Stephanoporos, Stephanosphaera, Stichococcus, Stichogloeoa, Stigeoclonium, Stigonema, Stipitococcus, Stokesiella, Strombomonas, Stylochrysalis, Stylodinium, Styloyxis, Stylosphaeridium, Surirella, Sykidion, Symploca, Synechococcus, Synechocystis, Synedra, Synochromonas, Synura, Tabellaria, Tabularia, Teilingia, Temnogametum, Tetmemorus, Tetrachlorella, Tetracyclus, Tetradesmus, Tetraedriella, Tetraedron, Tetraselmis, Tetraspora, Tetrastrum, Thalassiosira, Thamniochaete, Thorakochloris, Thorea, Tolypella, Tolypothrix, Trachelomonas, Trachydiscus, Trebouxia, Trentepholia, Treubaria, Tribonema, Trichodesmium, Trichodiscus, Trochiscia, Tryblionella, Ulothrix, Uroglena, Uronema, Urosolenia, Urospora, Uva, Vacuolaria, Vaucheria, Volvox, Volvulina, Westella, Woloszynskia, Xanthidium, Xanthophyta, Xenococcus, Zygnema, Zygnemopsis,* and *Zygonium.*

Green non-sulfur bacteria include but are not limited to the following genera:

*Chloroflexus, Chloronema, Oscillochloris, Heliothrix, Herpetosiphon, Roseiflexus,* and *Thermomicrobium.*

Green sulfur bacteria include but are not limited to the following genera: *Chlorobium, Clathrochloris,* and *Prosthecochloris,*

Purple sulfur bacteria include but are not limited to the following genera: *Allochromatium, Chromatium, Halochro-*

*matium, Isochromatium, Marichromatium, Rhodovulum, Thermochromatium, Thiocapsa, Thiorhodococcus,* and *Thiocystis,*

Purple non-sulfur bacteria include but are not limited to the following genera: *Phaeospirillum, Rhodobaca, Rhodobacter, Rhodomicrobium, Rhodopila, Rhodopseudomonas, Rhodothalassium, Rhodospirillum, Rodovibrio,* and *Roseospira.*

In various embodiments, engineered organism are modified to comprise an engineered nucleic acid that encodes a heterologous protein that is expressed by the engineered cell, causes overexpression of an endogenous protein within the engineered cell, causes downregulation of an endogenous protein in the engineered cell, or causes a gene knock-out in the engineered cell. Selection, modification and use of such organisms in the photobioreactor apparatus and systems that can be optimized for growth at particular operating conditions expected within the photobioreactor apparatus are described in more detail in commonly-owned U.S. Provisional Patent Application Ser. Nos. 60/971,224; 60/987,046; 60/987,058; 60/987,056; 60/987,055; 60/987,054; 60/987,053; 60/987,052; 60/987,051; 60/987,050; 60/987,049, which are incorporated herein by reference.

In certain embodiments, the photoautotrophic organism can be transformed with exogenous DNA, engineered nucleic acids, organisms engineered to down-regulate or knock out expression of an endogenous gene, express heterologous gene, overexpress an endogenous gene related to photosynthesis. In various embodiments, engineered light capturing organisms include: *Arabidopsis thaliana, Panicum virgatum, Miscanthus giganteus,* and *Zea mays* (plants), *Botryococcus braunii, Chlamydomonas reinhardtii* and *Dunaliela salina* (algae), *Synechococcus* sp PCC 7002, *Synechococcus* sp. PCC 7942, *Synechocystis* sp. PCC 6803, and *Thermosynechococcus elongatus* BP-1 (cyanobacteria), *Chlorobium tepidum* (green sulfur bacteria), *Chloroflexus auranticus* (green non-sulfur bacteria), *Chromatium tepidum* and *Chromatium vinosum* (purple sulfur bacteria), *Rhodospirillum rubrum, Rhodobacter capsulatus,* and *Rhodopseudomonas palusris* (purple non-sulfur bacteria).

Still other organisms, e.g., heterotrophs can be engineered to confer photoautotrophic properties. The resultant engineered organism will convert light, water and carbon dioxide into biomass and carbon-based products of interest. Such organisms include, without limitation, *Acetobacter aceti, Acetobacter* sp., *Bacillus subtilis, Bacillus* sp., *Clostridium ljungdahlii, Clostridium thermocellum, Clostridium* sp., *Escherichia coli, Escherichia* sp., *Penicillium chrysogenum, Penicillium* sp., *Pichia pastoris, Pichia* sp., *Saccharomyces cerevisiae, Saccharomyces* sp., *Schizosaccharomyces pombe, Schizosaccharomyces* sp., *Pseudomonas fluorescens, Pseudomonas* sp., *Salmonella typhimurium, Salmonella* sp., *Thermus thermophilus, Thermus* sp., *Zymomonas mobilis* and *Zymomonas* sp.

Separation of Products and Removal of Products from the Gas Phase

The solar biofactory is aimed at enabling highly productive organisms to be maximally productive. A critical element of this is the ability to capture what is being made. In addition to biomass, numerous biofuels, biochemicals, drugs, and other products can be produced. Several of these products, including but not limited to ethanol, butanol, butyric acid, propane, propanol, and methanol, have sufficiently low boiling points that they will likely be present in the gas stream given operations at ~50° C. As such, the gas stream represents a simplified way for these products to be collected. Independent of the presence or absence of a recycle, the gas stream will contain processes effluent gas from its source, waste gas from the organisms (e.g., oxygen), and potentially gaseous product. These components can be separated out by methods well known in the art.

Compounds such as ethanol can be captured by cooling the gas and collecting at the appropriate point for ethanol, similar to as in fractional distillation. Gases such as oxygen can be captured with metals and through pressure swing adsorption operations.

The removal of such compounds can occur independent of which apparatus is used. Any recycle that would occur would be after the removal of desired compounds. The removed compounds can either be sufficiently pure or be subject to additional purification prior to commercial use.

Solar heat results in EtOH enrichment into purge air, which is suited for capture in the photobioreactor, for example in the liquid return manifold 140. Purification of ethanol based on distillation and/or condensation scheme developed in ASPEN and laboratory measurements. Recovery energy consumption is expected to be comparable to best in class conventional EtOH recovery.

Of particular note, separation of biofuels from their production vectors as in traditional plants represents a very significant source of capital expenditure. By incorporating it fundamentally into the process, the solar biofactory can significantly reduce operating expenditures.

Removal of Product from the Liquid Phase

Products not found in the gas phase will be found intermixed in the liquid phase. The product itself may be a solid (e.g., heavy hydrocarbons) or liquid (e.g., mid range hydrocarbons), but can be separated from the liquid media. Since strain development would result in a secreted product, a simple gravity decanting at photobioreactor is contemplated. Crude decant stream is pumped to central plant for solids polishing and dewatering to final product specifications In removing the product of interest from the liquid phase, a certain volume of cell and media mixture is removed, which is then put through a separation process to isolate the desired product. This is performed independent of the product. Different products with different properties are then separated by means well known in the art. Solids can be separated by settling, centrifugation and filtration. Hydrophilic or otherwise water soluble substances are collected through techniques including but not limited to distillation. Hydrophobic substances including but not limited to alkanes, alkenes, alkynes, fatty alcohols, fatty aldehydes, fatty acids, fatty esters, ethyl esters and other hydrophobic or organic materials can be separated through a biphasic system. Vapor-phase extraction of water soluble substances for recovery of organic substances from an aqueous medium is also contemplated.

In certain embodiments, light capturing organisms are grown in a photobioreactor apparatus with a continuous supply of inputs via inlet means and continuous removal of product via an outlet means. Batch, fed-batch, and continuous fermentations are common and well known in the art and examples can be found in Thomas D. Brock in Biotechnology: A Textbook of Industrial Microbiology, Second Edition (1989) Sinauer Associates, Inc., Sunderland, Mass., or Deshpande, Mukund V., Appl. Biochem. Biotechnol (1992), 36:227.

Using embodiments of the solar biofactory, system and methods, the product of interest can be secreted, released, removed or extracted from the cells in the solar biofactory. In one embodiment, the product is excreted, secreted or released from the organism into the media for extraction as described above. In embodiments where the final product is released from an organism, a continuous process can be employed, e.g., fed-batch, and continuous fermentations. In this approach, a photobioreactor apparatus with organisms producing desirable products can be assembled in multiple ways.

In one embodiment, the reactor is operated in bulk continuously, with a portion of media removed and held in a less agitated environment such that an aqueous product will self-separate out with the product removed and the remainder returned to the fermentation chamber. In another embodiment, the reactor is operated in fed-batch.

In embodiments where the product does not separate into an aqueous phase, media is removed and appropriate separation techniques (e.g., chromatography, distillation, etc.) are employed. Separation by distillation may be advantageous in low ambient temperatures.

To process biomass, the optimal biomass density is measured at an optical density ($OD_{730}$) and subjected to process streams resulting from, for example, the primary fractionation or saccharification of lignocellulosic biomass, which can be typically highly complex slurries that are difficult to process and separate. Such slurries often contain substantial levels (10-20% w/w) of insoluble lignocellulosic solids as well as high concentrations of soluble biomass sugars (>10-20%) along with a variety of other soluble components (organic and inorganic acids, aldehydes, phenolics, etc.) that are typically present at lower levels. Known separation process technologies such as solid/liquid (S/L) separations of such slurries, are used for bulk or primary S/L separations, as well as for secondary/polishing S/L separations. Other separation techniques are used to recover products and facilitate bio/catalysis, e.g., reactive separations schemes that will enable in situ combination with bio/catalysis steps, techniques to remove smaller suspended particles or high molecular weight compounds from partially clarified liquors and use of membrane separation systems for separation and recovery of specific components (e.g., specific sugars or organic acids) or classes of components (e.g., mixed sugars or mixed phenolics) from clarified biomass hydrolyzate liquors.

Alternatively, the product is not secreted by the organism. In this embodiment, fed-batch or batch fermentation approach is employed. In such cases, cells are grown under continued exposure to inputs (light, water, and carbon dioxide) as specified above until the reaction chamber is saturated with cells and product. A significant portion to the entirety of the culture is removed, the cells are lysed, and the products are isolated by appropriate separation techniques (e.g., chromatography, distillation, filtration, centrifugation, ultrafiltration, microfiltration, etc. or combinations thereof). The obtained biomass might be subjected to a washing step, the liquid being added to the separated fermentation supernatant.

Desired products such as small molecules drugs and biological can be separated using known separation techniques. Exemplary separation techniques include gel electrophoresis, including but not limited to isoelectric focusing and capillary electrophoresis; dielectrophoresis; sorting, including but not limited to fluorescence-activated sorting techniques; chromatography, including but not limited to HPLC, FPLC, size exclusion (gel filtration) chromatography, affinity chromatography, ion exchange chromatography, hydrophobic interaction chromatography, immunoaffinity chromatography, and reverse phase chromatography; ligand-receptor binding, such as biotin-avidin, biotin-streptavidin, maltose-maltose binding protein (MBP), calcium-calcium binding peptide; aptamer-target binding; zip code hybridization; and the like. Detailed discussion of separation techniques can be found in, among other places, Rapley; Sambrook et al.; Sambrook and Russell; Ausbel et al.; Molecular Probes Handbook; Pierce Applications Handbook; Capillary Electrophoresis: Theory and Practice, P. Grossman and J. Colburn, eds., Academic Press (1992); Wenz and Schroth, PCT International Publication No. WO 01/92579; M. Ladisch, Bioseparations Engineering: Principles, Practice, and Economics, John Wiley & Sons (2001); and Liebler, Introduction to Proteomics, Humana Press (2002).

One exemplary separation process provided for water insoluble products herein is a two phase (bi-phasic) separation process. This process involves fermenting the genetically engineered production hosts under conditions sufficient to produce a fatty acid derivative or other hydrophobic compound, allowing the derivative to collect in an organic phase and separating the organic phase from the aqueous fermentation broth. This method can be practiced in both a batch and continuous fermentation setting.

Bi-phasic separation uses the relative immisciblity of fatty acid derivatives to facilitate separation. Immiscible refers to the relative inability of a compound to dissolve in water and is defined by the compounds partition coefficient. The partition coefficient, P, is defined as the equilibrium concentration of compound in an organic phase (in a bi-phasic system the organic phase is usually the phase formed by the fatty acid derivative during the production process, however, in some examples an organic phase can be provided (such as a layer of octane to facilitate product separation) divided by the concentration at equilibrium in an aqueous phase (i.e. fermentation broth). When describing a two phase system the P is usually discussed in terms of log P. A compound with a log P of 10 would partition 10:1 to the organic phase, while a compound of log P of 0.1 would partition 10:1 to the aqueous phase. One or ordinary skill in the art will appreciate that by choosing a fermentation broth and the organic phase such that the fatty acid derivative being produced has a high log P value, the fatty acid derivative will separate into the organic phase, even at very low concentrations in the fermentation vessel.

There are essentially three types of hydrocarbon products: (1) aromatic hydrocarbon products, which have at least one aromatic ring; (2) saturated hydrocarbon products, which lack double, triple or aromatic bonds; and (3) unsaturated hydrocarbon products, which have one or more double or triple bonds between carbon atoms. A "hydrocarbon product" may be further defined as a chemical compound that consists of C, H, and optionally 0, with a carbon backbone and atoms of hydrogen and oxygen, attached to it. Oxygen may be singly or double bonded to the backbone and may be bound by hydrogen. In the case of ethers and esters, oxygen may be incorporated into the backbone, and linked by two single bonds, to carbon chains. A single carbon atom may be attached to one or more oxygen atoms. Hydrocarbon products may also include the above compounds attached to biological agents including proteins, coenzyme A and acetyl coenzyme A. Hydrocarbon products include, but are not limited to, hydrocarbons, alcohols, aldehydes, carboxylic acids, ethers, esters, carotenoids, and ketones.

Hydrocarbon products also include alkanes, alkenes, alkynes, dienes, isoprenes, alcohols, aldehydes, carboxylic acids, surfactants, wax esters, polymeric chemicals [polyphthalate carbonate (PPC), polyester carbonate (PEC), polyethylene, polypropylene, polystyrene, polyhydroxyalkanoates (PHAs), poly-beta-hydroxybutyrate (PHB), polylactide (PLA), and polycaprolactone (PCL)], monomeric chemicals [propylene glycol, ethylene glycol, and 1,3-propanediol, ethylene, acetic acid, butyric acid, 3-hydroxypropanoic acid (3-HPA), acrylic acid, and malonic acid], and combinations thereof. In some embodiments, the hydrocarbon products are alkanes, alcohols, surfactants, wax esters and combinations thereof. Other hydrocarbon products include fatty acids, acetyl-CoA bound hydrocarbons, acetyl-CoA bound carbohydrates, and polyketide intermediates.

Using the solar biofactory system and methods, light harvesting organisms can be grown to produce hydrocarbon products and intermediates over a large range of sizes. Specific alkanes that can be produced include, for example, ethane, propane, butane, pentane, hexane, heptane, octane, nonane, decane, undecane, dodecane, tridecane, tetradecane, pentadecane, hexadecane, heptadecane, and octadecane. In various embodiments, the hydrocarbon products are octane, decane, dodecane, tetradecane, and hexadecane. Hydrocarbon precursors such as alcohols that can be produced include, for example, ethanol, propanol, butanol, pentanol, hexanol, heptanol, octanol, nonanol, decanol, undecanol, dodecanol, tridecanol, tetradecanol, pentadecanol, hexadecanol, heptadecanol, and octadecanol. In additional embodiments, the alcohol is selected from ethanol, propanol, butanol, pentanol, hexanol, heptanol, octanol, nonanol, and decanol.

Hydrocarbons can additionally be produced as biofuels. A biofuel is any fuel that derives from a biological source—recently living organisms or their metabolic byproducts. A biofuel may be further defined as a fuel derived from a metabolic product of a living organism. In various embodiments, produced biofuels include, but are not limited to, biodiesel, biocrude, ethanol, petroleum, butanol, and propane.

Surfactants are used in a variety of products, including detergents and cleaners, and are also used as auxiliaries for textiles, leather and paper, in chemical processes, in cosmetics and pharmaceuticals, in the food industry and in agriculture. In addition, they may be used to aid in the extraction and isolation of crude oils which are found hard to access environments or as water emulsions. There are four types of surfactants characterized by varying uses. Anionic surfactants have detergent-like activity and are generally used for cleaning applications. Cationic surfactants contain long chain hydrocarbons and are often used to treat proteins and synthetic polymers or are components of fabric softeners and hair conditioners. Amphoteric surfactants also contain long chain hydrocarbons and are typically used in shampoos. Non-ionic surfactants are generally used in cleaning products.

Solid forms of carbon including, for example, coal, graphite, graphene, cement, carbon nanotubes, carbon black, diamonds, and pearls. Pure carbon solids can comprise such materials as coal and diamond.

Pharmaceuticals can be produced including, for example, isoprenoid-based taxol and artemisinin, or oseltamivir.

Detection and Analysis

Generally, the products of interest produced from the solar biofactory can be analyzed by any of the standard analytical methods, such as gas chromatography (GC), mass spectrometry (MS) gas chromatography-mass spectrometry (GCMS), and liquid chromatography-mass spectrometry (LCMS), high performance liquid chromatography (HPLC), capillary electrophoresis, Matrix-Assisted Laser Desorption Ionization time of flight-mass spectrometry (MALDI-TOF MS), nuclear magnetic resonance (NMR), near-infrared (NIR) spectroscopy, viscometry (Knothe, G., R. O. Dunn, and M. O. Bagby. 1997. Biodiesel: The use of vegetable oils and their derivatives as alternative diesel fuels. Am. Chem. Soc. Symp. Series 666: 172-208), titration for determining free fatty acids (Komers, K., F. Skopal, and R. Stloukal. 1997. Determination of the neutralization number for biodiesel fuel production. Fett/Lipid 99(2): 52-54), enzymatic methods (Bailer, J., and K. de Hueber. 1991. Determination of saponifiable glycerol in "bio-diesel." Fresenius J. Anal. Chem. 340(3): 186), physical property-based methods, wet chemical methods etc. can be used to analyze the levels and the identity of the product produced by the organisms used in a solar biofactory.

Production of Fuels & Chemicals

This invention, or a subsequent related version, will be used to produce commercial product (such as ethanol, alkanes, glucose, etc.) from various microbiological production strains. The invention will also generate valuable control code and software that can be used more broadly in other phototrophic production systems targeting a variety of value-added products that can be produced by algae, microalgae and cyanobacteria. The invention is therefore of wide ranging value to any production system that has the objective to utilize sunlight in a process that requires management of the thermal load while limiting the requirement of external heating and cooling utilities to maintain temperature control for viability and optimum performance.

In various aspects, the invention sets forth a photobioreactor capable of culturing light capturing organisms to an $OD_{730}$ of about 14 g/L DCW. Preferably, the PBR is capable of culturing light capturing organisms to an $OD_{730}$ of about at least 2-5 g/L, 5-10 g/L or 10-20 g/L DCW.

In other aspects, the invention sets forth a photobioreactor capable of culturing light capturing organisms to a DCW productivity of 3.5 $g/m^2/hr$.

Preferred embodiments include a photobioreactor comprising a passive thermal regulation system.

References cited herein discuss the general concepts of photobioreactors and associated temperature control using water baths, ponds, water sprays, flue gas based temperature control or internal and external heat exchangers. None suggests passive thermal control as a strategy to regulate the growth conditions of the phototroph such that both daytime and night time conditions are optimized. Passive heating and cooling is used in largely stationary situations such as building using a variety of adaptive features (see for instance "Passive Solar Heating and Cooling" at the website of the Arizona Solar Center http://www.azsolarcenter.com/technology/pas-3.html). Adjustable solar tracking is also used in the concentrating solar thermal industry to track and focus sunlight to a central point to capture heat energy at a suitably high temperature to generate power or split water thermally for hydrogen generation (see for instance website of eSolar at http://www.esolar.com). None of the systems used in the art suggest that it would be possible to regulate the culturing conditions within a reactor using microorganisms by adjusting the orientation on a real-time basis. One reference suggests that adjusting the tilt angle of a flat-plate reactor twice or four times a year can improve productivity by optimizing the light regime in the reactor when compared to utilizing a fixed tilt angle. Compared to a fixed tilt angle throughout the year the productivity was improved by approximately 7% adjusting the tilt angle twice and by almost 15% when adjusting the tilt angle four times (Hu, Q., Faiman, D. and Richmond, A. "Optimal tilt angles of enclosed reactors for growing photoautotrophic microorganisms outdoors" Journal of Fermentation and Bioengineering (1997) 85:230-236). The same reference provides a design drawing that uses a thermostat and cooling water supply pipe and sprinklers to control temperature. The reference actually teaches against the use of passive control. It is a novel feature to integrate a passive thermal control system to control the growth conditions to at least reduce but more preferably eliminate essentially all external cooling and heating utility thus overcoming one of the greatest impediments to effective culturing of photoautotrophs in enclosed reactors.

The following examples are illustrative and are non-limiting to the present teachings.

Example 1

The following illustrates an exemplary photobioreactor, a prototype developed to study fluid and gas mechanics, mass transfer and cell growth characteristics. A Sunlite® SLT multiwall polycarbonate sheet (FarmTek) was cut to a particular dimension. Each partition measured about 10 mm×10 mm. The sheet was capped horizontally at the top and the bottom using acrylic tubes (McMaster). A separate sparge tube was assembled near the bottom cap. At the center of each vertical partition, a hole was punctured. The sparge tube also punctured, was then glued together at the interface between the tube and the photobioreactor chamber until it was sealed.

A heat exchanger was connected to the photobioreactor assembly and a 1/10 hp centrifugal pump was used to circulate the fluid within the photobioreactor. The flowrate was controlled by a half-inch globe valve. The heat exchanger was connected to a circulating heater/chiller unit to keep the temperature constant at 37° C. A peristaltic pump (Cole Palmer) with a 0.2μ filter was used to pump media into the photobioreactor. A pH and D.O. probe (Neponset Controls) were installed on the reactor assembly to monitor OD, pH and temperature. pH was controlled with $CO_2$ and its to the photobioreactor was controlled by use of a solenoid valve and LabVIEW software. Air was supplied from an air compressor. A condenser was also installed on the gas outlet to control evaporation loss from the bioreactor.

The bioreactor configuration also included super high output florescent lighting installed anywhere from 2-8 inches above the bioreactor assembly. The light bank held eight T-5 54 watt bulbs, 48" in length. Six of the bulbs installed were 6500 k cool white and the other two bulbs were 300 k warm white; each with a lumen output of 5,000 per bulb. Mylar® sheet was placed under the assembly. The bioreactor assembly was tilted at a 30 degree angle.

The photobioreactor assembly proposed above has been constructed and tested in actual field conditions. It is proposed to construct a "sand box" that can use different ground covers (optimizing heat absorption, diffuse reflection and heat storage for passive heating at night or during cold periods) and install sufficient photobioreactors within this space such that edge effects will be eliminated. These photobioreactors can then be equipped with simple manually adjustable inclination to confirm that the intended surface coatings and treatments combined with inclination control can indeed be used to effectively control temperature with minimal external heating and cooling.

4'×8' multi-wall PALRAM polycarbonate sheet was purchased online from FarmTek (www.farmtek.com; 1440 Field of Dreams Way, Dyersville, Iowa 52040)

DEGLAS IMPACT 8 mm double-skinned sheet, color clear 0119: 47.25" wide×8' long and DEGLAS IMPACT 16 mm double-skinned sheet, color clear 0119: 47.25" wide×8' long acrylic sheet was purchased from Evonik Cyro Canada, Inc. (www.evonik.com; 180 Attwell Drive, Suite 101, Toronto, ON, M9W 6A9)

Makrolon multi UV 2/10-10.5, Makrolon multi UV 3/16-16, Makrolon multi UV 3x/16-25 sheet samples were received from Sheffield Plastics Inc., a Bayer Material-Science Company (www.sheffieldplastics.com; www.bayer-imsa.com; www.bayersheeteurope.com; 119 Salisbury Road, Sheffield, Mass. 01257)

Assorted sizes of Acrylic tubing was purchased online from McMaster-Carr (www.mcmaster.com; 200 New Canton Way Robbinsville, N.J. 08691-2343)

Pumps, heat exchanger and probes purchased from standard equipment suppliers (i.e. VWR, Cole Parmer, Fisher)

Mylar reflective sheet from International Plastics Inc., 3052 NE Harrison St., Issaquah, Wash. 98029.

Example 2

Impact of Mixing: Air Bubbles v. Liquid Pump

The photobioreactor was kept at a constant temperature of 37° C.

Air Bubbles

| Air bubble Flow | |
|---|---|
| Mixing Power Input (W/m2) | Light-Dark Cycle Time (ms) |
| Tilt Angle (deg) 10 | |
| 1.6 | 220 |
| 2.4 | 200 |
| 3.1 | 180 |
| 3.9 | 160 |
| 4.7 | 150 |
| 5.4 | 140 |
| 6.2 | 140 |
| Tilt Angle (deg) 30 | |
| 2.7 | 200 |
| 4.0 | 180 |
| 5.3 | 160 |
| 6.6 | 140 |
| 7.9 | 130 |
| 9.1 | 120 |
| 10.4 | 110 |

Liquid Pump

| Liquid Pump | |
|---|---|
| Mixing Power Input (W/m2) | Light-Dark Cycle Time (ms) |
| Tilt Angle (deg) 10 | |
| 12 | 1290 |
| 31 | 940 |
| 56 | 780 |
| 86 | 680 |
| 120 | 610 |
| 158 | 560 |
| 200 | 520 |
| Tilt Angle (deg) 30 | |
| 15 | 1300 |
| 36 | 960 |
| 63 | 800 |
| 96 | 700 |
| 133 | 630 |
| 175 | 580 |
| 220 | 540 |

Example 3

Media Study & Optimization

A series of studies were conducted to determine the types and amounts of nutrients required in a medium to allow Synechococcus sp. PCC 7002 to reach a concentration of at least 10 g/L dry cell weight (DCW). The A+ media previously published had not been extensively studied and the amount of cell growth that it could support was unknown. The A+ media contents are provided in the following Table:

desired range and approximate conversion to Dry Cell Weight (DCW in g/L) can be obtained by dividing the OD by 3.0. Growth in the form of OD was then plotted over time and compared to see how each change in variable effected the growth.

| Ingredient | Amount per liter | Units | Comments |
|---|---|---|---|
| NaCl | 18 | g | 1.8% NaCl; compare to seawater at 2.8% NaCl |
| KCl | 0.6 | g | |
| NaNO$_3$ | 1 | g | Nitrogen source |
| 500 g/l MgSO$_4$•7H$_2$O | 10 | mL | Final [Mg2+] = 0.049%; compare to seawater at 0.128%; store nonsterile at 4° C. |
| 50 g/l KH$_2$PO$_4$ | 1 | mL | Store nonsterile at 4° C. |
| 17.76 g/l CaCl$_2$ | 15 | mL | Store nonsterile at 4° C. |
| 3 g/l NaEDTA$_{tetra}$ | 10 | mL | Alternative liquid stocks; store nonsterile at 4° C. |
| 3.89 g/l FeCl$_3$•6H$_2$O (in 0.1 N HCl) | 1 | mL | Store nonsterile at 4° C. |
| 1 M Tris (pH 8.2) | 8.25 | mL | Provides buffering activity; replaces 100 g/l stock; store nonsterile at 4° C. |
| P1 Metals Solution | 1 | mL | Trace metals; store nonsterile at room temperature |
| MilliQ H$_2$O | 950 | mL | |
| 4 mg/l Vitamin B$_{12}$ | 1 | mL | |

Studies were conducted by making modifications to A+ media, inoculating it with *Synechococcus* sp. PCC 7002 and then tracking the optical density against culture age in flasks. The growth caused by the changes in any variable was then compared. DCW was also determined in some cases. This data was used to then build an optimized media that could support growth up to at least 15 g/L DCW.

A+ was used as the initial starting point for the media studies. After an improvement was discovered studies would be conducted on the improved media. Improvements in media were measured by the growth that was supported. Freshly prepared media was used in each study. This helped to avoid a precipitate often seen in the media during storage. The inoculum used for each experiment was made by inoculating a single *Synechococcus* sp. PCC 7002 colony into a bubble tube and growing up for several days. Samples from the bubble tube were then inoculated in 125 mL flasks with 10 mL of each type of media. The starting optical density of each flask and the weight of the flask with the culture in it was then measured. All flasks were placed in Infors shakers at 150 RPM, 37° C. and 2.0% CO$_2$.

Evaporation losses were corrected daily by adding filter sterilized MilliQ water. The amount of water added was determined by the change in weight that occurred each day. After correcting for evaporation and thoroughly mixing by shaking each flask, a 100 μl of the culture was removed. The sample was then diluted and optical density (OD) measurements were taken on a SpectraMax at a wavelength of 730 nm. Dilutions were made to achieve an OD between the range of 0.04-0.40, as this is the range thought to have the best accuracy in measurement. Provided the dilutions are made to the Antifoam Selection Study Four types of Antifoam were added to flasks at a concentration of 200 μl/L. These samples were then grown overnight and growth rates were compared. Microscope pictures were then taken to determine what effect if any the various antifoams had upon a cyanobacterium. The results for the Antifoam Selection Study can be seen in Table 1.

TABLE 1

Effect of Various Antifoams: Optical Density vs. Age

| Sample | Initial OD | OD after 13.5 hours | Growth Rate hr$^{-1}$ | Doubling Time |
|---|---|---|---|---|
| A+ | 0.339 | 1.535 | 0.11 | 6.20 |
| Antifoam B Emulsion | 0.338 | 1.355 | 0.10 | 6.74 |
| Antifoam 204 | 0.342 | 1.545 | 0.11 | 6.21 |
| Suppressor 3965 | 0.333 | 1.695 | 0.12 | 5.75 |
| MCA 222 | 0.337 | 1.735 | 0.12 | 5.71 |

Suppressor 3965 was selected as the optimal antifoam. This was due to its decreased doubling time and that MCA 222 may have looked slightly less healthy under the microscope when compared to A+ and Suppressor 3965.

Table 2 shows the results for the PO$_4$/EDTA test. This study varied the concentration of KH$_2$PO$_4$ in the media and it also investigated the effect of removing EDTA. Optical density vs. culture age was recorded and compared.

TABLE 2

Effect of Varied Concentrations of KH$_2$PO$_4$ and EDTA: Optical Density vs. Age

| Culture Age (hrs) | 1A 50 mG PO$_4$ | 1B 50 mg PO$_4$ | 2A 100 mg PO$_4$ | 2B 100 mg PO$_4$ | 3A 250 mg PO$_4$ | 3B 250 mg PO$_4$ | 4A no EDTA | 4B no EDTA |
|---|---|---|---|---|---|---|---|---|
| 0 | 0.158 | 0.158 | 0.152 | 0.175 | 0.176 | 0.168 | 0.162 | 0.177 |
| 21.5 | 2.65 | 2.55 | 2.5 | 2.75 | 2.52 | 2.94 | 1.15 | 1.2 |
| 44.75 | 6.44 | 6.8 | 6.2 | 6.92 | 6.2 | 7.44 | 1.74 | 1.72 |
| 71 | 10.96 | 10.44 | 10.96 | 11.2 | 10.28 | 11.28 | 1.88 | 1.84 |

TABLE 2-continued

Effect of Varied Concentrations of KH$_2$PO$_4$ and EDTA: Optical Density vs. Age

| Culture Age (hrs) | 1A 50 mG PO$_4$ | 1B 50 mg PO$_4$ | 2A 100 mg PO$_4$ | 2B 100 mg PO$_4$ | 3A 250 mg PO$_4$ | 3B 250 mg PO$_4$ | 4A no EDTA | 4B no EDTA |
|---|---|---|---|---|---|---|---|---|
| 94.75 | 12.8 | 12.6 | 12.84 | 13.04 | 11.6 | 13.88 | 1.72 | 2.04 |
| 117.25 | 13.52 | 13.36 | 13.48 | 13.72 | 12.6 | 13.76 | — | — |

Figure 18:
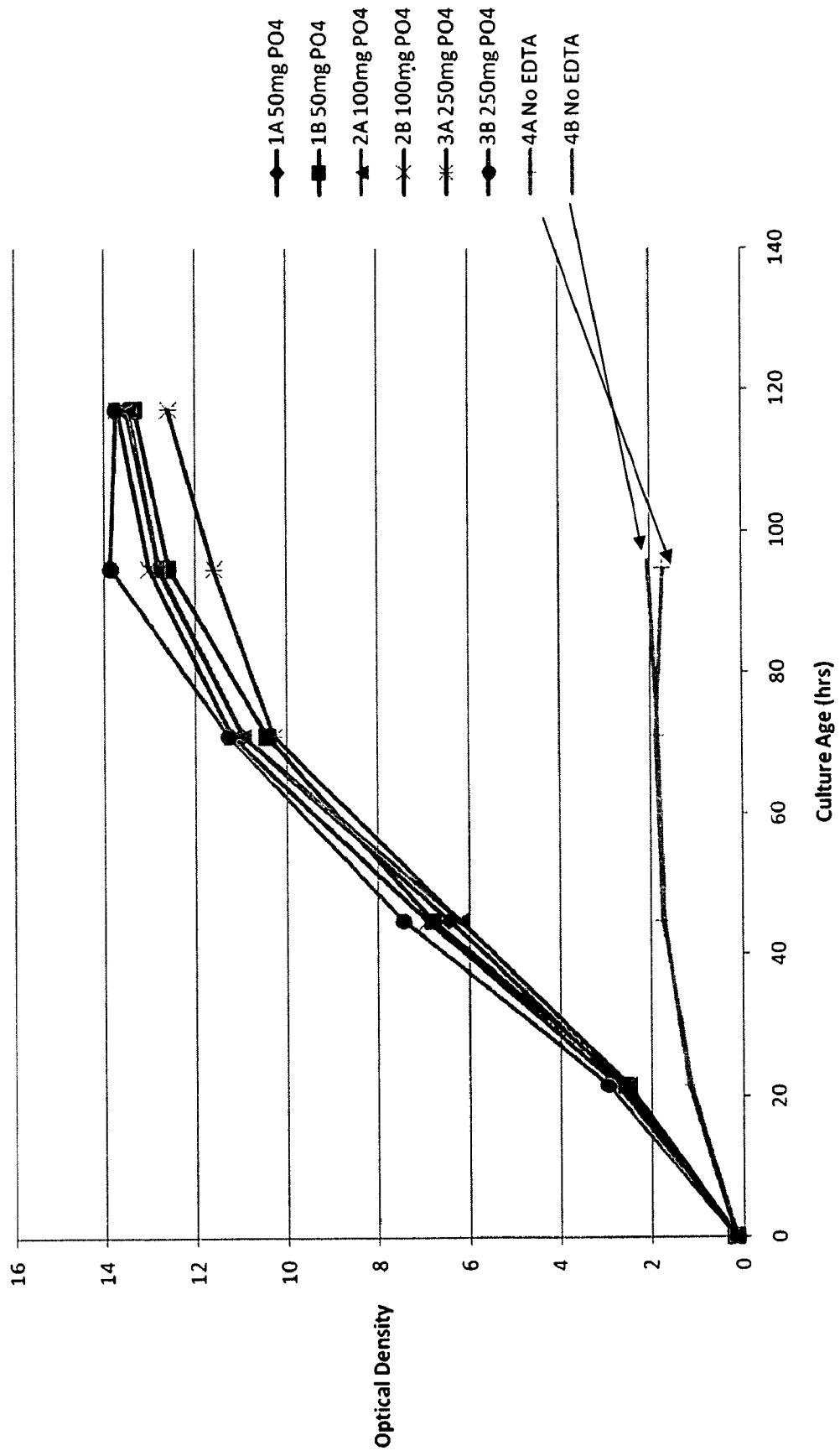
FIG. 18 shows graphically the effect of removing EDTA in the media.

The data shown in table and Table 2 suggest that EDTA may be an essential component of the media and that it should not be removed. Increasing the levels of phosphate did not have a noticeable effect on cell growth. The growth curve shows a nutrient limitation at a culture age of 100 hours. This implied that the cells were running out of another essential nutrient before they were running out of phosphate. See FIG. 18.

Iron Source Test

Cultures were grown with different sources of iron. The sources used were: ferric chloride (A+ iron source), ferric citrate and ferrous sulfate. Table 3 shows the data for the various iron sources.

TABLE 3

Effect of Varied Iron Sources on Cell Growth: Optical Density Vs. Age

| Time (hrs) | FeCl$_3$ | FeCl$_3$ | Ferric Citrate | Ferric Citrate | FeSO$_4$ | FeSO$_4$ |
|---|---|---|---|---|---|---|
| 0 | 0.127 | 0.124 | 0.114 | 0.12 | 0.128 | 0.121 |
| 21.3 | 2 | 1.83 | 2.08 | 2.39 | 2.36 | 2.32 |
| 73.3 | 7.12 | 7.08 | 12.56 | 12.64 | 12.8 | 12.2 |
| 94.05 | 7.92 | 7.8 | 13.28 | 13.68 | 13.88 | 13.8 |
| 115.55 | 9.08 | 9.04 | 15.56 | 15.24 | 15.68 | 14.96 |
| 135.8 | 8.84 | 9.96 | 14.88 | 14.84 | 14.88 | 15.88 |

Figure 19:
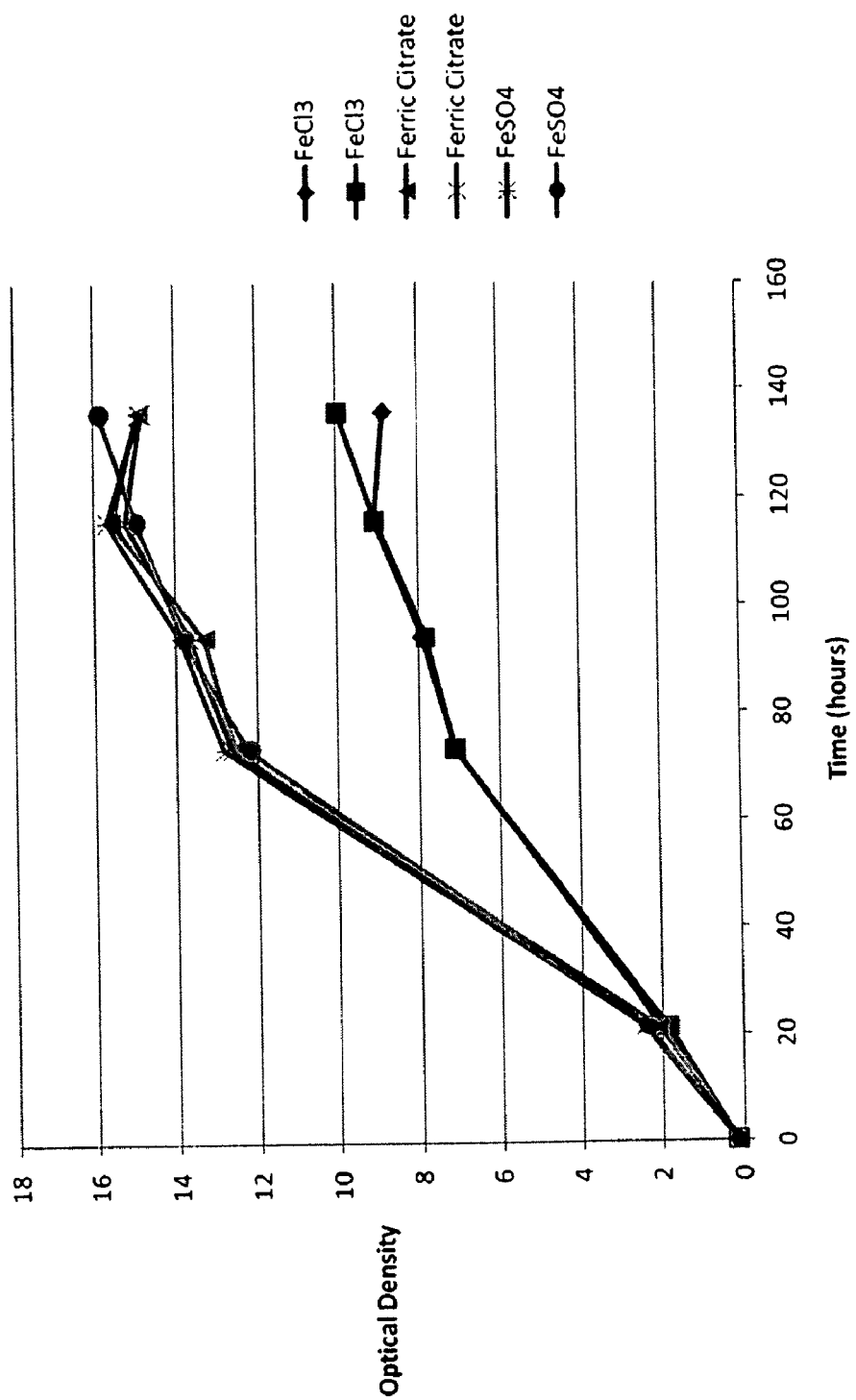
FIG. 19 shows the effect of various iron sources in the media.

A graph of this data can be seen in FIG. 19.

The iron sources ferric citrate and ferrous sulfate both showed a similar positive impact on growth when compared to FeCl$_3$. The decision was made to switch to ferric citrate as an iron source because it outperformed FeCl$_3$ and unlike FeSO$_4$ it contained a chelating agent. This study and the EDTA study clearly shows the benefit of chelators in media.

The media with 2× nitrogen, iron and phosphate (JB 2.0) showed a significant improvement in growth when compared to A+. Comparing just the average of JB 2.0 to A+ average resulted in the data shown in Table 4. (The media protocol for JB 2.0 is shown in Example 4)

TABLE 4

JB2.0 Compared to A+: Optical Density Vs. Age

| Culture Age | A+ | A+ | A+ Avg. | JB 2.0 | JB 2.0 | JB 2.0 Avg. |
|---|---|---|---|---|---|---|
| 0 | 0.127 | 0.126 | 0.1265 | 0.133 | 0.125 | 0.129 |
| 21.5 | 2.36 | 1.96 | 2.16 | 2.24 | 2.22 | 2.23 |
| 70 | 10.28 | 10.6 | 10.44 | 11.56 | 10.56 | 11.06 |
| 92.5 | 12.24 | 12.12 | 12.18 | 15.72 | 13.64 | 14.68 |
| 118.5 | 13.44 | 13.12 | 13.28 | 19.68 | 17.76 | 18.72 |
| 139 | 13.76 | 13.44 | 13.6 | 21.68 | 19.84 | 20.76 |
| 166 | 13.68 | 13.44 | 13.56 | 24.16 | 22.24 | 23.2 |
| 188 | 13.6 | 13.84 | 13.72 | 24.64 | 23.68 | 24.16 |

Figure 20:
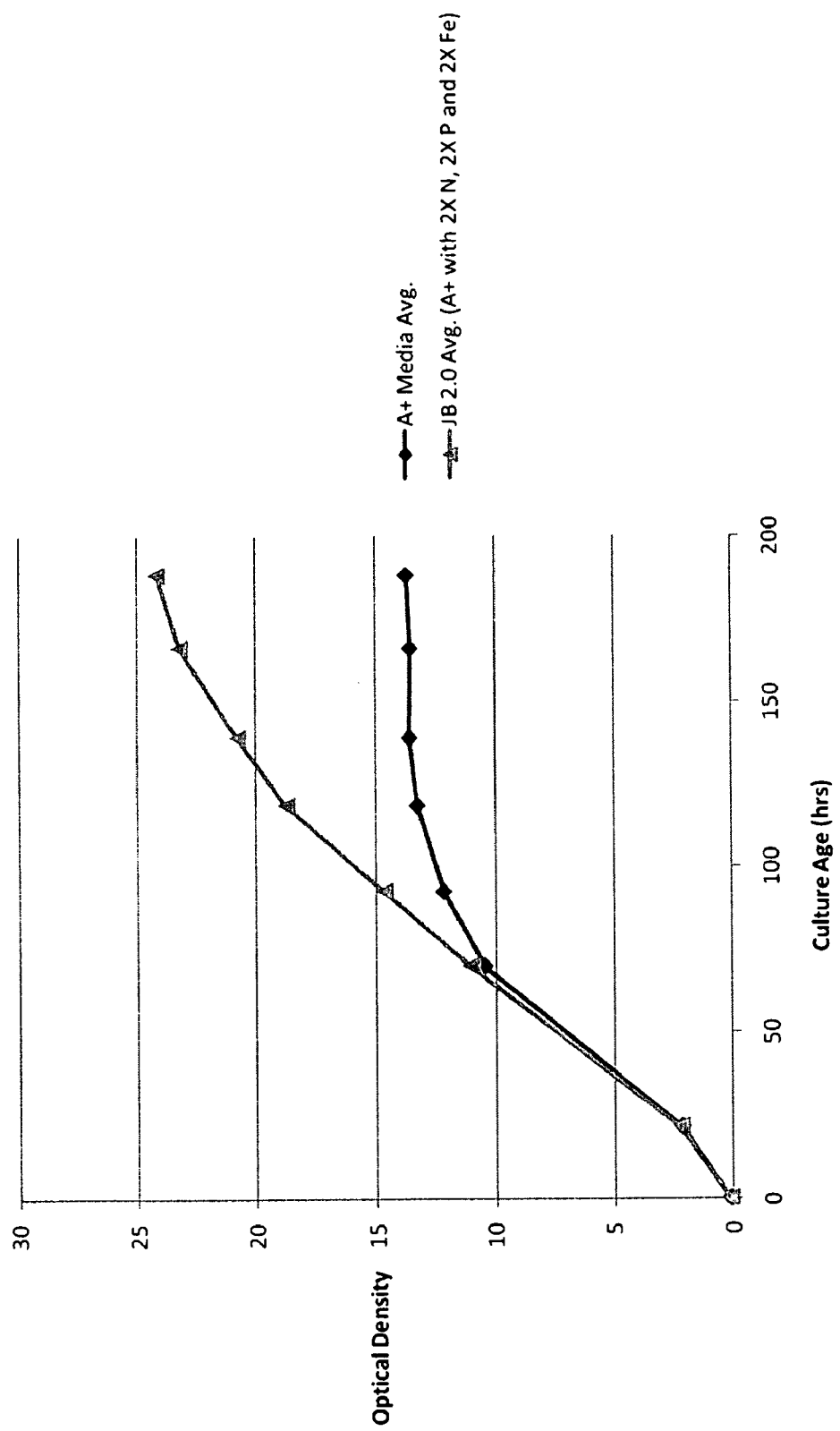
FIG. 20 contrasts the growth effect of an optimized media compared to the A+ media.

A+ had a significant decline in growth rate around hour 100 whereas JB 2.0 continued to grow unhindered until hour 139. This can be attributed to a nutrient limitation that eventually developed in the A+ media that did not occur in the 2× nitrogen, phosphate and iron JB 2.0 media (FIG. 20).

The three variables of nitrogen, phosphate and iron where identified as the key nutrient sources that run out first in the media.

NPFe Dry Cell Weights

| Test | Dry Cell Weight (g/L) |
|---|---|
| 1A 2X NPFe | 7.83 |
| 1B 2X NPFe | 7.61 |
| 2A 4X NPFe | 11.83 |
| 2B 4X NPFe | 12 |
| 3A 6X NPFe | 11.39 |
| 3B 6X NPFe | 12.39 |

Figure 21:
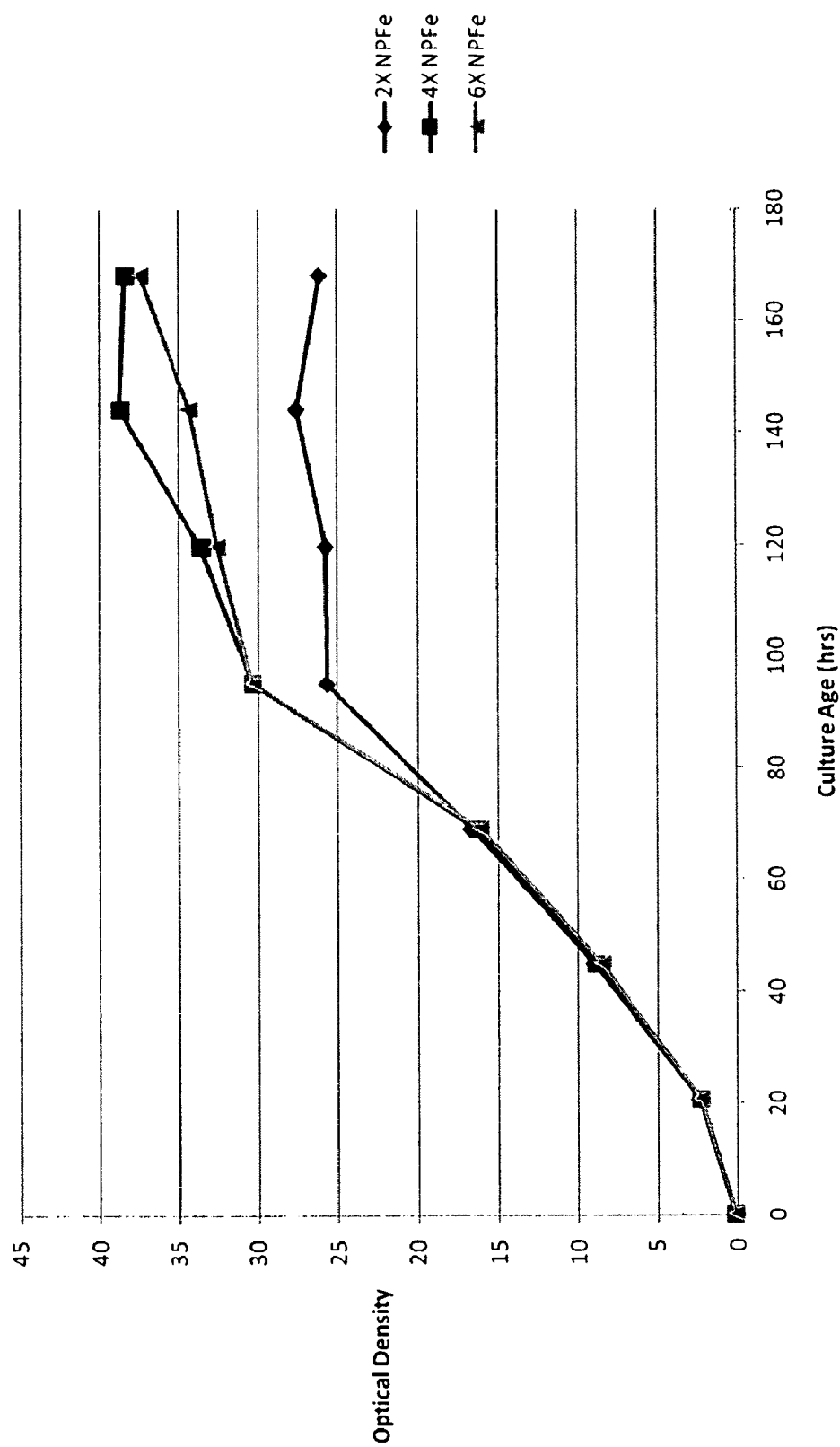
FIG. 21 shows the change in growth of inoculants with increased amount of N, P and Fe.
Figure 22:
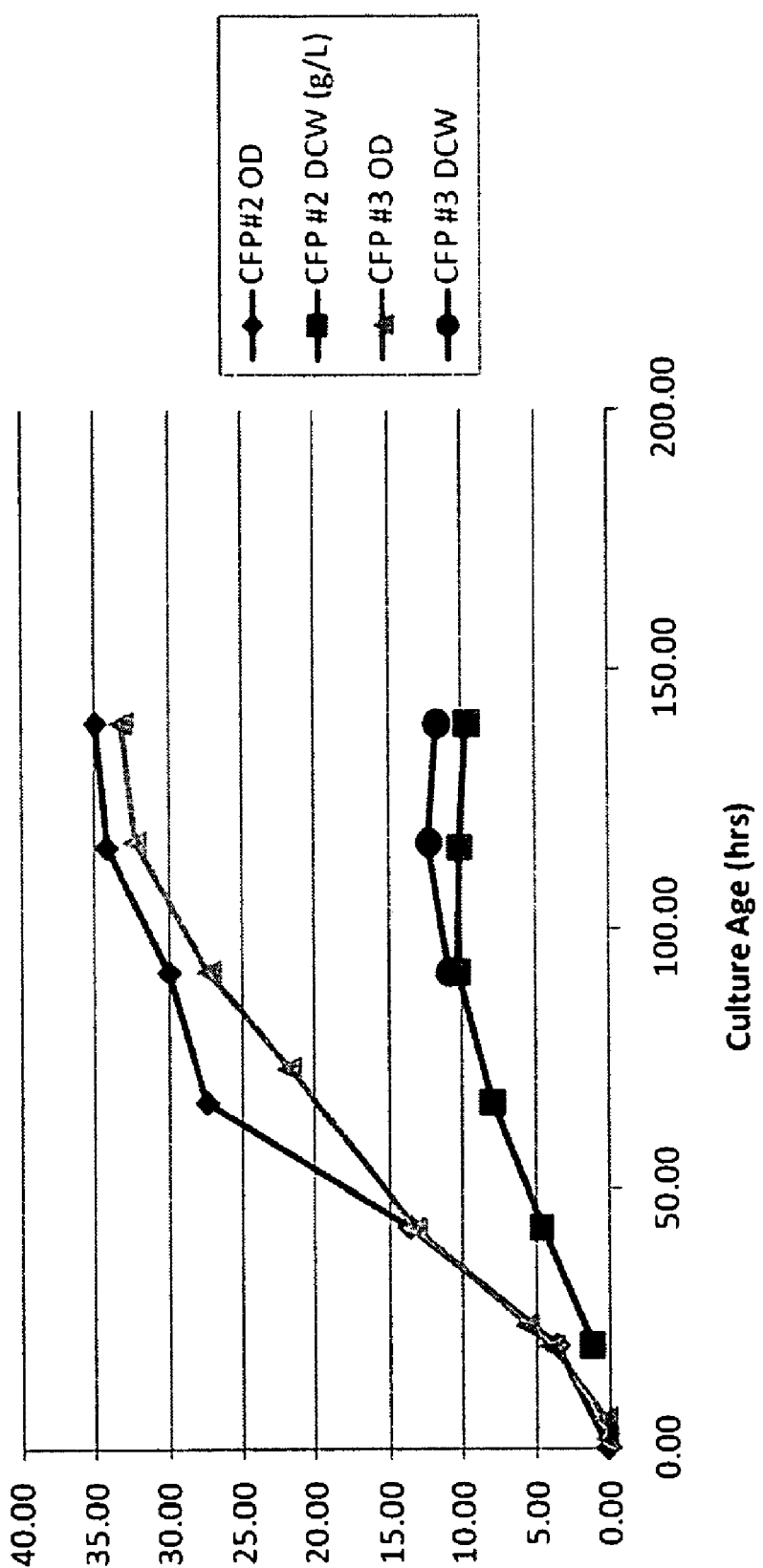
FIG. 22 is graphical representation of *Synechococcus* culture growth to about 10 g/L after inoculation in the photobioreactor apparatus.
Figure 23:
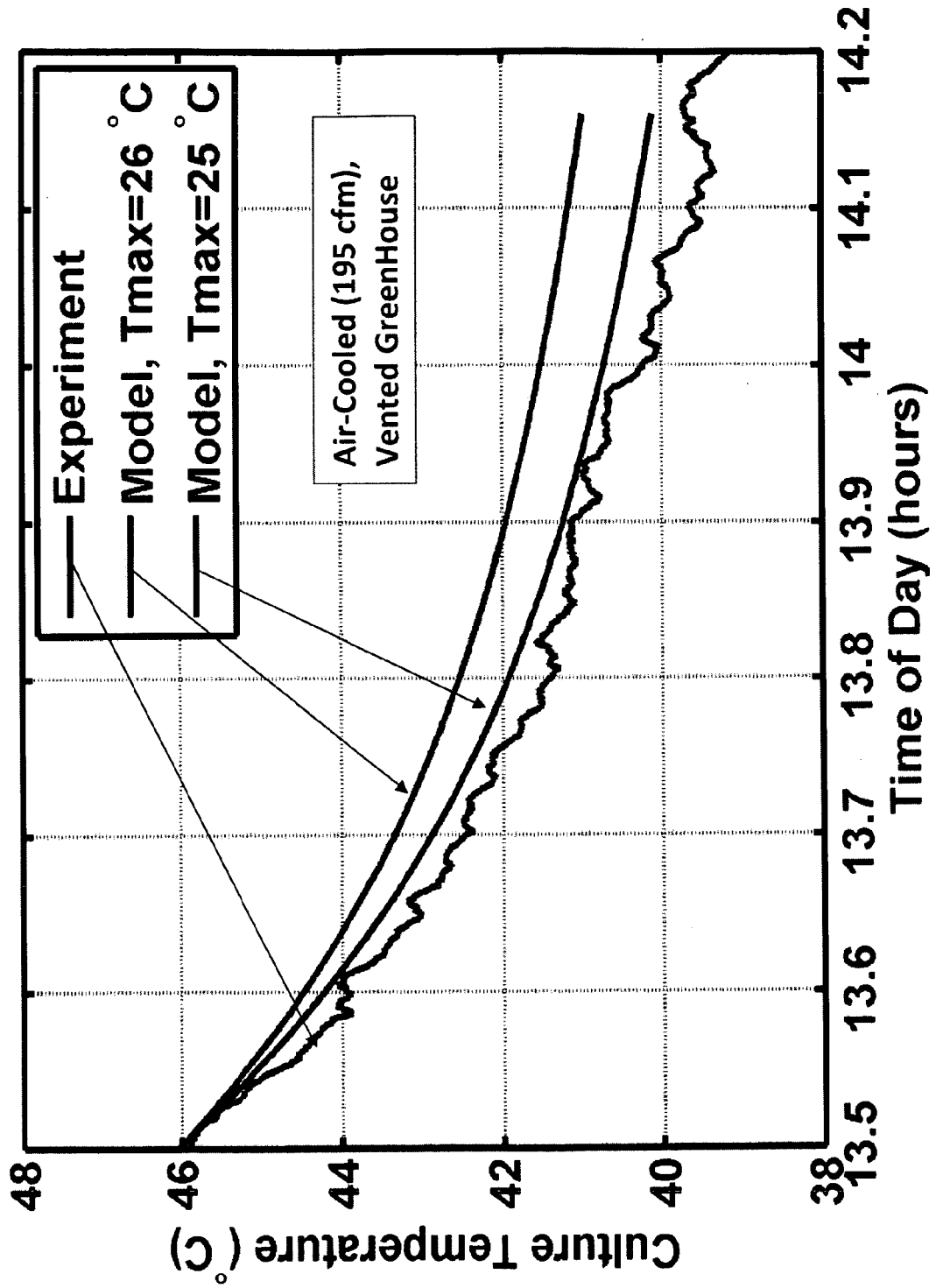
FIG. 23 is a graph of a thermal management progression.

The media with 2× nitrogen, phosphate, and iron grew to about an OD of 25 before it hit nutrient limitation. It became chlorotic at that point and stopped growing. The 4× and the 6× amounts continued on to an OD of 40. This was the basis for the media protocol JB 2.1 which has the concentrations of nitrogen, phosphate and iron at 4× (FIG. 21).

Example 4

Enhanced Media Composition

The following table lists the procedure for creating 1 Liter of culture media.

| Chemical | mg/L added | FW | Molarity | Units | Source |
|---|---|---|---|---|---|
| NaCl | 18000 | 58.44 | 308 | mM | Fisher |
| KCl | 600 | 74.55 | 8.05 | mM | Fisher |
| NaNO$_3$ | 4000 | 84.99 | 47.06 | mM | Sigma Aldrich |
| MgSO$_4$—7H$_2$O | 5000 | 246.47 | 20.29 | mM | Sigma Aldrich |
| KH$_2$PO$_4$ | 200 | 136.09 | 1.47 | mM | Fisher |
| CaCl$_2$ | 266 | 110.99 | 2.40 | mM | Sigma |
| NaEDTA$_{tetra}$ | 30 | 372.24 | 80.59 | uM | Fisher |
| Ferric Citrate | 14.1 | 244.95 | 57.48 | uM | Acros Organics |
| Tris | 1000 | 121.14 | 8.25 | mM | Fisher |
| Vitamin B$_{12}$ (Cyanocobalamin) | 0.004 | 1355.37 | 2.95E−03 | uM | Sigma Aldrich |
| H$_3$BO$_3$ | 34 | 61.83 | 554 | uM | Acros Organics |
| MnCl$_2$—4H$_2$O | 4.3 | 197.91 | 21.83 | uM | Sigma |
| ZnCl | 0.32 | 136.28 | 2.31 | uM | Sigma |
| MoO$_3$ | 0.030 | 143.94 | 0.21 | uM | Sigma Aldrich |
| CuSO$_4$—5H$_2$O | 0.0030 | 249.69 | 0.012 | uM | Sigma Aldrich |
| CoCl$_2$—6H$_2$O | 0.012 | 237.93 | 0.051 | uM | Sigma |

Vitamin $B_{12}$ should be stored in the dark at 4° C. All other liquid stocks may be stored unsterile at room temperature. Weigh out 18.0 grams of NaCl in a plastic weigh boat and pour it into a 2 Liter graduated cylinder. Using a separate plastic weigh boat, weigh out 600 mg of KCl and add it into the 2 L cylinder. Add 4 grams of $NaNO_3$ into the cylinder. Add half of the desired final volume of MilliQ $H_2O$, 500 mL for a 1 Liter batch. Place the cylinder on a stir plate, add a magnetic stirrer and mix well. Let the media mix during the addition of the components below. From a previously made stock solution of 500 g/L $MgSO_4$ $7H_2O$ add 10 mL to the media. From a previously made stock solution of 50 g/L $KH_2PO_4$ add 4 mL to the media. From a filtered stock solution of 17.76 g/L $CaCl_2$ add 15 mL to the media. The need for the filtered $CaCl_2$ is to help prevent precipitation in storage. From a stock solution of 3 g/l $NaEDTA_{tetra}$ add 10 mL to the media. From a stock solution of 3.52 g/l Ferric Citrate (in 0.1 N HCl) add 4 mL to the media. From a stock of 1 M Tris (pH 8.2) add 8.25 mL. Add 1 mL of P1 metals to the media. The components of the P1 metal solution can be seen below. Add 1 mL of 4 mg/L Vitamin $B_{12}$ to the media. After all of the above components have been added and mixed bring the volume with MilliQ $H_2O$ in the cylinder up to the 1 Liter mark. After the addition let the media mix for one minute. Filter sterilize the media using a 0.22 µM pore size filter, into an autoclaved 1 Liter bottle. Sterile technique should be used. Keep the pH of the media within 7.9-8.0. Higher than 8.0 can cause precipitation.

Example 5

Culturing *Synechococcus* sp. PCC 7002 in Enhanced Media Composition

*Synechococcus* sp. PCC 7002 (ATCC) was inoculated in JB 2.1 plus 1 g/L citric acid media in a photobioreactor apparatus under continuous illumination and bubbled with air containing 1% $CO_2$ in the photobioreactor apparatus and monitored for growth.

Reactor details: Airflow ~1 VVM ("40" on rotometer), Air @ 25 psig, CO2@30 psig
CFP #3

| Culture age (hr) | OD | pH | DCW g/L | Δ time | growth rate | dbl time |
|---|---|---|---|---|---|---|
| 0.00 | | | | | | |
| 1.75 | 0.271 | 8.0 | | 1.7 | | |
| 5.50 | 0.433 | 7.8 | | 3.8 | 0.125 | 6 |
| 19.50 | 3.95 | 7.8 | | 14.0 | 0.158 | 4 |
| 23.50 | 5.66 | 7.8 | | 4.0 | 0.090 | 8 |
| 42.50 | 13.30 | 7.8 | | 19.0 | 0.045 | 15 |
| 73.00 | 21.84 | 7.9 | | 30.5 | 0.016 | 43 |
| 91.50 | 27.30 | 7.9 | 10.9 | 18.5 | 0.012 | 57 |
| 116.50 | 32.30 | 7.8 | 12.3 | 25.0 | 0.007 | |
| 139.50 | 33.20 | 7.8 | 11.70 | | | |

CFP #2

| Culture age (hr) | OD | DCW g/L |
|---|---|---|
| 0.00 | 0.20 | |
| 19.75 | 3.58 | 1.2 |
| 42.50 | 13.70 | 4.6 |
| 66.50 | 27.40 | 8.0 |
| 91.50 | 30.00 | 10.3 |
| 115.50 | 34.20 | 10.2 |
| 139.50 | 35.00 | 9.7 |

The result of the experiment produced about 10 g/L (DCW) of Synechococcus.

Example 6

Culturing Genetically Modified *Synechococcus* sp. PCC 7002

Construction of pJB5

A pJB5 base plasmid was designed as an empty expression vector for recombination into *Synechococcus* sp. PCC 7002. Two regions of homology, the Upstream Homology Region (UHR) and the Downstream Homology Region (DHR) were designed to flank the construct. These 500 bp regions of homology correspond to positions 3301-3800 and 3801-4300 (Genbank Accession NC_005025) for the UHR and DHR, respectively. The aadA promoter, gene sequence, and terminator were designed to confer spectinomycin and streptomycin resistance to the integrated construct. For expression, pJB5 was designed with the aph2 kanamycin resistance cassette promoter and ribosome binding site (RBS). Downstream of this promoter and RBS, restriction endonuclease recognition sites are designed and inserted for NdeI and EcoRI, as well as the sites for XhoI, BamHI, SpeI and PacI. Following the EcoRI site, the terminator from the pyruvate decarboxylase gene of *Zymomonas mobilis* (pdc) is included. Convenient XbaI restriction sites flank the UHR and DHR, allowing cleavage of the DNA intended for recombination from the rest of the vector. pJB5 was constructed by DNA2.0 (Menlo Park, Calif.).

The pJB5-gene of interest construct is cloned into *Synechococcus* sp. PCC 7002 using the following protocol. Synechococcus 7002 is grown for 48 hours from colonies in an incubated shaker flask at 30° C. at 1% $CO_2$ to an $OD_{730}$ of 1 in optimized medium described in Frigaard N U et al. (2004) "Gene inactivation in the cyanobacterium *Synechococcus* sp. PCC 7002 and the green sulfur bacterium *Chlorobium tepidum* using in vitro-made DNA constructs and natural transformation" Methods Mol Biol 274:325-340. 500 µL of culture is added to a test-tube with 30 µL of 1-5 µg of DNA prepped from a Qiagen Qiaprep Spin Miniprep Kit (Valencia, Calif.) for each construct. Cells are incubated with sparging of 1% $CO_2$ at approximately 1 vvm (volume gas per volume liquid per minute) for 4 hours. 2004 of cells are plated on optimized medium plates with 1.5% agarose and grown at 30° C. for two days in low light. 10 µg/mL of spectinomycin based on total plate agar volume is added as a concentrated solution underneath the agar on each plate. Resistant colonies are visible in 7-10 days. See WO2009/111513 for further details of microorganism engineering and culturing.

The genetically Modified *Synechococcus* sp. PCC 7002 is inoculated in the enhanced media under continuous illumination and bubbled with air containing 1% $CO_2$ in the photobioreactor apparatus of the invention and monitored for growth.

Below is a table of *Synechococcus* sp. PCC 7002 cultured in a photobioreactor of the invention.

| age | OD | DCW | daily productivity |
|---|---|---|---|
| 0 | 0.199 | 0.333689 | g/m²/hr |
| 19.75 | 3.58 | 6.0030488 | 0.57 |
| 25 | 5.86 | 9.8262195 | 1.46 |
| 42.5 | 13.7 | 22.972561 | 1.50 |
| 66.6 | 22.4 | 37.560976 | 1.21 |
| 91 | 30 | 50.304878 | 1.04 |
| 115 | 34.2 | 57.347561 | 0.59 |

Example 7

Ethanol Productivity Model

To calculate the productivity the following assumptions were made:

Radiation: photosynthetically active radiation (PAR) fraction of total solar radiation 47%, historical average PAR at ground based on NREL 1991-2005 datasets, assumes future radiation characteristics will be consistent with historic values;

Production: production rate is linear with radiation intensity, well-documented photon utilization is 8 photons/$CO_2$ fixed into biomass (Pirt, S J 1983, Biotechnol Bioeng, 25: 1915-1922), 85% of PAR striking the photobioreactor system enters the culture, 85% of PAR photons entering the photobioreactor are available for conversion, 15% lost to photoinhibition & radiation when culture not at operating temperature, Estimate 3 days of culture growth followed by 8 weeks of production; 95% online production, Estimate 5% of photosynthetic energy dedicated to cell maintenance (Pirt S J 1965 Proc Roy Soc 163: 224-231).

Method of calculating ethanol productivity based on ethanol concentration in the culture and the stripping rate:

The ethanol concentration in the bioreactor culture is a function of two quantities:

(a) The production rate ($k_p$): The production rate is the rate of increase of ethanol concentration in the liquid with time i.e.:

$$\frac{d[\text{Ethanol}]}{dt} = k_p$$

(b) The stripping rate (s): Due to the volatility of ethanol, it will be continuously leaving the liquid in the form of vapor. The rate at which it leaves the reactor is a function of the concentration of ethanol in the liquid and a variety of other factors such as temperature, airflow, etc. For our purposes, all other factors are held fixed hence we can think of the rate of ethanol loss being solely dependent on the liquid concentration, i.e:

$$\frac{d[\text{Ethanol}]}{dt} = -s[\text{Ethanol}]$$

Combining the two equations, we can write:

$$\frac{d[\text{Ethanol}]}{dt} = k_p - s[\text{Ethanol}]$$

Note that in the above equation, the production rate $k_p$ is time independent which is clearly false. In reality, it would depend on time via the density of the culture and the light regime. However, as long as we treat the production rate $k_p$ as an average production rate between measurements, the relation is valid.

The equation is a basic first order equation and can be easily solved to obtain:

$$k_p = \frac{s[\text{Ethanol}(t)]e^{ts} - s[\text{Ethanol}(t=0)]}{e^{ts} - 1}$$

Note that this gives a production rate that is in terms of concentration of ethanol per unit time for the incident light intensity at which the experiment was conducted. This has to be multiplied by the reactor volume to obtain the production rate in terms of grams of ethanol per unit time. Units can then be converted to suitable time units such as day instead of hour. For example, in our case, we define the stripping rate in units of h^(−1) and our reactor of volume V covers and area of 0.5 m^2. Therefore our production rate (in grams per square meter per day) is given by 2 $k_p$ V*24 at the incident light intensity at which the experiment was conducted.

While this invention has been particularly shown and described with references to example embodiments thereof, it will be understood by those skilled in the art that various changes in form and details may be made therein without departing from the scope of the invention encompassed by the appended claims.

What is claimed is:

1. A method for producing fuels or chemicals comprising:
   (a) employing a photobioreactor assembly comprising:
      a reactor structure; and
      a greenhouse structure configured to provide a greenhouse environment for the reactor structure, the reactor structure and the greenhouse structure spaced relative to each other to provide temperature control of the photobioreactor, wherein the reactor structure comprises a closed reactor and the greenhouse structure comprises at least two side sheets spaced apart with the reactor disposed therebetween;
   (b) introducing into the reactor of the photobioreactor assembly at least one phototroph;
   (c) culturing the phototroph in the reactor of the photobioreactor assembly whereby the phototroph utilizes light and $CO_2$ to produce the fuels or chemicals.

2. The method of claim 1, further comprising employing an assembly comprising a real time adaptive control system to maintain optimum productivity.

3. The method of claim 1, wherein the passive thermal regulation system regulates temperature of the photobioreactor between about 25° C. to about 60° C.

4. The method of claim 1, wherein the photobioreactor separates the fuels or chemicals continuously.

5. The method of claim 1, wherein the reactor contains a biomass concentration of less than 20 g/L, 10 g/l or 5 g/L.

6. The method of claim 1, wherein the phototroph is an engineered phototroph, the method further comprising culturing the engineered phototroph to an $OD_{730}$ of about 14 g/L dry cell weight.

7. The method of claim 1, wherein the phototroph is an engineered phototroph, the method further comprising culturing the engineered phototroph to an optical cell density of at least 2-5 g/L, 5-10 g/L or 10-20 g/L dry cell weight.

8. The method of claim 1, further comprising removing the fuels or chemicals from the photobioreactor.

9. The method of claim 1, wherein the photobioreactor is adapted to achieve passive thermal control of the enclosed reactor within about 5° C. to about 10° C. of ambient air temperature.

10. The method of claim 1, wherein the phototroph is an engineered phototroph, and the engineered phototroph utilizes light and $CO_2$ to produce the fuels or chemicals at an areal productivity of at least about 0.4 $g/m^2/hr$.

* * * * *